US010400031B2

(12) United States Patent
Smith et al.

(10) Patent No.: US 10,400,031 B2
(45) Date of Patent: Sep. 3, 2019

(54) IDENTIFICATION OF ANTIBODIES SPECIFIC FOR LYSSAVIRUSES AND METHODS OF THEIR USE

(71) Applicant: The Govt. of the U.S.A. as rep. by the Secretary of the Dept. of Health and Human Services, Atlanta, GA (US)

(72) Inventors: Todd G. Smith, Decatur, GA (US); Xianfu Wu, Atlanta, GA (US)

(73) Assignee: The Government of the United States of America as represented by the Secretary of the Department of Health and Human Services, Atlanta, GA (US)

( * ) Notice: Subject to any disclaimer, the term of this patent is extended or adjusted under 35 U.S.C. 154(b) by 68 days.

(21) Appl. No.: 15/725,557

(22) Filed: Oct. 5, 2017

(65) Prior Publication Data

US 2018/0134767 A1 May 17, 2018

Related U.S. Application Data

(62) Division of application No. 14/813,427, filed on Jul. 30, 2015, now Pat. No. 9,809,643, which is a division of application No. 13/879,782, filed as application No. PCT/US2011/056738 on Oct. 18, 2011, now Pat. No. 9,115,187.

(60) Provisional application No. 61/394,651, filed on Oct. 19, 2010.

(51) Int. Cl.
*C07K 16/10* (2006.01)
*G01N 33/569* (2006.01)
*C12Q 1/00* (2006.01)
*A61K 39/00* (2006.01)

(52) U.S. Cl.
CPC ....... *C07K 16/10* (2013.01); *G01N 33/56983* (2013.01); *A61K 2039/505* (2013.01); *C07K 2317/21* (2013.01); *C07K 2317/31* (2013.01); *C07K 2317/33* (2013.01); *C07K 2317/52* (2013.01); *C07K 2317/56* (2013.01); *C07K 2317/565* (2013.01); *C07K 2317/569* (2013.01); *C12N 2760/20145* (2013.01); *C12N 2810/6081* (2013.01); *C12Q 1/00* (2013.01); *G01N 2333/145* (2013.01); *G01N 2500/10* (2013.01)

(58) Field of Classification Search
None
See application file for complete search history.

(56) References Cited

FOREIGN PATENT DOCUMENTS

| | | |
|---|---|---|
| EP | 0402 029 A2 | 12/1990 |
| WO | WO 2006/084006 | 8/2006 |

OTHER PUBLICATIONS

Rudikoff et al., "Single amino acid substitution altering antigen-binding specificity," *Proc Natl Acad Sci USA* 79(6):1979-1983, 1982.

Tamura et al., "Structural Correlates of an Anticarcinoma Antibody: Identification of Specificity-Determining Residues (SDRs) and Development of a Minimally Immunogenic Antibody Variant by Retention of SDRs Only," *J Immunol* 164(3):1432-1441, 2000.

Carmen et al., "Concepts in Antibody Phage Display," *Briefings in Functional Genomics and Proteomics*, vol. 1(2):189-203, 2002.

Champion et al., "The Development of Monoclonal Human Rabies Virus-Neutralizing Antibodies as a Substitute for Pooled Human Immune Globulin in the Prophylactic Treatment of Rabies Virus Exposure," *J. Immunol. Meth.*, vol. 235:81-90, 2000.

Famm et al., "Thermodynamically Stable Aggregation-Resistant Antibody Domains through Directed Evolution," *J. Mol. Biol.*, vol. 376:926-931, 2008.

Goudsmit et al., "Comparison of an Anti-Rabies Human Monoclonal Antibody Combination with Human Polyclonal Anti-Rabies Immune Globulin," *J. Infect. Dis.*, vol. 193:796-801, 2006.

Kramer et al., "The Human Antibody Repertoire Specific for Rabies Virus Glycoprotein as Selected from Immune Libraries," *Eur. J. Immunol.*, vol. 35:2131-2145, 2005.

Lafon et al., "Human Monoclonal Antibodies Specific for the Rabies Virus Glycoprotein and N Protein," *J. Gen. Virol.*, vol. 71:1689-1696, 1990.

Lee et al., "Selection of Human Antibody Fragments by Phage Display," *Nature Protocols*, vol. 2(11):3001-3008, 2007.

Smith et al., "Antibody phage display technologies with special reference to angiogenesis," *FASEB J* 19(3):3331-341, 2005.

Tikunova and Morozova, "Phage Display on the Base of Filamentous Bacteriophages: Application for Recombinant Antibodies Selection," *Acta Naturae* 1(3):20-28, 2009.

Weyer et al., "Cross-Protective and Cross-Reactive Immune Responses to Recombinant Vaccinia Viruses Expressing Full-Length Lyssavirus Glycoprotein Genes," *Epidemiol. Infect.*, vol. 136:670-678, 2008.

Wright et al., "Virus neutralizing activity of African fruit bat (*Eidolon helvum*) sera against emerging lyssaviruses," *Virology*, 408:183-189, 2010.

*Primary Examiner* — Nicole Kinsey White
(74) *Attorney, Agent, or Firm* — Klarquist Sparkman, LLP

(57) ABSTRACT

Described herein is a method of identifying a monoclonal antibody (or antigen-binding fragment thereof) that specifically binds a plurality of *lyssaviruses* for use in post-exposure rabies prophylaxis or in the treatment of clinical rabies. The method includes using a naïve antibody phage display library to screen for phage clones that bind whole recombinant rabies virus or cells expressing glycoprotein from multiple *lyssaviruses* (such as RABV, MOKV and WCBV) and/or specifically bind recombinant glycoprotein from different *lyssaviruses*.

13 Claims, 4 Drawing Sheets

Specification includes a Sequence Listing.

N P M G psi L
ERA backbone
N P M G* psi L
ERA with G333 mutation
N P M G* psi L
Trans unit 1
Trans unit 2
ERA with two introduced transcriptional (trans) units
Insert MOKV and WCBV G genes
N P MOKV G M G* psi WCBV G L
ERA with three glycoprotein genes (ERA-3G)

Virus Neutralization (IU/ml)
0.06
0.05
0.04
0.03
0.02
0.01
0
Groups/Clones
1
2
8
20
21
22
37

IDENTIFICATION OF ANTIBODIES SPECIFIC FOR LYSSAVIRUSES AND METHODS OF THEIR USE

CROSS REFERENCE TO RELATED APPLICATIONS

This is a divisional of U.S. application Ser. No. 14/813,427, filed Jul. 30, 2015, which is a divisional of U.S. application Ser. No. 13/879,782, filed Apr. 16, 2013, issued as U.S. Pat. No. 9,115,187 on Aug. 25, 2015, which is the U.S. National Stage of International Application No. PCT/US2011/056738, filed Oct. 18, 2011, published in English under PCT Article 21(2), which claims the benefit of U.S. Provisional Application No. 61/394,651, filed Oct. 19, 2010. All of the above-listed application are incorporated herein by reference in their entirety.

FIELD

This disclosure concerns methods of identifying *lyssavirus*-specific antibodies and the use of such antibodies in the treatment and prophylaxis of rabies.

BACKGROUND

Rabies is an inevitably fatal but preventable disease. In developing countries rabies remains a significant endemic disease burden. World-wide approximately 55,000 people die of rabies each year (WHO Expert Consultation on Rabies, 2004). Rabies is preventable with proper early post-exposure treatment. Currently, post-exposure prophylaxis includes thorough wound-washing with soap and water followed by administration of vaccine and anti-rabies virus immunoglobulin (RIG) of human or equine origin. RIG administered shortly after exposure at the wound site provides passive immunity which neutralizes rabies virus and prevents its spread until the patient's immune response following vaccination is elicited. Deaths due to post-exposure prophylaxis failure are most commonly attributed to deviations from the recommended regimen such as late initiation of post-exposure prophylaxis or no administration of RIG (Wilde, *Vaccine,* 25:7605-7609, 2007). In developing countries, availability of RIG is extremely low with only 1-2% of post-exposure prophylaxis being performed using RIG (Sudarshan et al., *Int J Infect Dis,* 11:29-35, 2007; WHO Consultation on a Monoclonal Antibody Cocktail for Rabies Post Exposure Treatment, 2002). In the United States, only human derived RIG is administered due to the risk of anaphylactic shock from exposure to equine immunoglobulins, but the concern of blood-born pathogen transmission in human RIG remains.

Human monoclonal antibodies (mAbs) that neutralize rabies virus have long been recognized as an alternative to overcome the limitations of RIG (Dietzschold et al., *J Virol,* 64:3087-3090, 1990). Adequate supplies of cell-cultured human mAbs could be produced in a cost-effective manner (Prosniak et al., *J Infect Dis,* 188:53-56, 2003). In addition, the use of human mAbs reduces the likelihood of an adverse immune response (Weiner, *J Immunother,* 29:1-9, 2006) and has been shown to be as effective as RIG in preventing rabies in animals (de Kruif et al., *Annu Rev Med,* 58:359-368, 2007). When a cocktail of two rabies-neutralizing, human mAbs was given with a rabies vaccine to animals experimentally infected with rabies, dose-dependent survival was observed, and all animals receiving the highest dose survived (Goudsmit et al., *J Infect Dis,* 193:796-801, 2006). The same cocktail was recently shown to be safe to administer to healthy humans in two phase-one clinical trials (Bakker et al., *Vaccine,* 26:5922-5927, 2008). However, selection of human monoclonal antibodies to include in such a cocktail has some limitations. The diversity of mAbs produced depends significantly on the diversity of viral antigens used to immunize human donors.

Rabies virus is a member (genotype 1) of the genus *Lyssavirus*. This genus also includes rabies-like viruses (genotypes 2-7) which can cause rabies disease in humans (Bourhy et al., *Virology,* 194:70-81, 1993; Gould et al., *Virus Res,* 54:165-187 1998). These viruses have a non-segmented, negative-sense, single-stranded RNA genome that encodes five proteins (Sokol et al., *Virology,* 38:651-665, 1969; Sokol et al., *J Virol,* 7:241-249, 1971). In the mature virion, RNA-dependent RNA polymerase, phosphoprotein, and nucleocapsid protein are associated with the genomic RNA while matrix protein and glycoprotein (G protein) surround it (Wiktor et al., *J Immunol,* 110:269-276, 1973). Trimeric G protein "spikes" coat the surface of the virion and as the only surface exposed protein, is responsible for attachment and entry into host cells. This also makes G protein the primary antigen for induction of virus-neutralizing antibodies, and G protein-specific mAbs are included in the cocktails currently being developed for post-exposure prophylaxis (Dietzschold et al., *J Virol,* 64:3087-3090, 1990; Kramer et al., *Eur J Immunol,* 35:2131-2145, 2005; Wunner et al., "Rabies Virus" in Rabies (Second Edition)," pp. 23-68, Academic Press, Oxford, 2007).

SUMMARY

Disclosed herein is a method of identifying an antibody (or antigen-binding fragment thereof) that specifically binds a plurality of *lyssaviruses*. Antibodies identified by the methods provided herein can be used, for example, for post-exposure rabies prophylaxis or in the treatment of clinical rabies.

Provided herein is a method of identifying a monoclonal antibody or antigen-binding fragment thereof that specifically binds at least two different *lyssaviruses*. In some embodiments, the method includes screening a naïve antibody phage display library with at least two different *lyssavirus* glycoproteins, such as by panning the library against a recombinant virus expressing at least two different *lyssavirus* glycoproteins, panning the library against recombinant glycoprotein from at least two different *lyssaviruses*, panning the library against at least two different cell lines expressing different *lyssavirus* glycoproteins, or any combination thereof.

In particular embodiments, the method includes screening a naïve antibody phage display library with (1) a recombinant rabies virus expressing glycoprotein from rabies virus (RABV), Mokola virus (MOKV) and West Caucasian bat virus (WCBV); (2) recombinant glycoprotein from at least two of RABV, MOKV, WCBV, Lagos bat virus (LBV) and Duvenhage virus (DUVV); and/or (3) at least two different cell lines expressing different *lyssavirus* glycoproteins selected from RABV, MOKV, WCBV, LBV and DUVV glycoprotein. The method further includes selecting a phage display clone that specifically binds to at least two different *lyssaviruses*, at least two different *lyssavirus* glycoproteins, or both.

In some embodiments, the phage display library is a naïve human $V_H$ domain library.

Also provided are isolated monoclonal antibodies (or antigen-binding fragments thereof) identified according to the methods disclosed herein and their use in the treatment or prophylaxis of rabies.

Further provided are isolated monoclonal antibodies (or antigen-binding fragments thereof) that specifically bind at least two different *lyssaviruses* or that specifically bind recombinant glycoprotein from at least two different *lyssaviruses*. In some embodiments, the $V_H$ domain of the antibody is encoded by a nucleotide sequence at least 85% identical to any one of SEQ ID NOs: 1-110. Also provided are methods of treating rabies in a subject by administering to the subject a monoclonal antibody disclosed herein.

Expression vectors, such as an Fc IgG expression vector, comprising the nucleotide sequence of any one of SEQ ID NOs: 1-110 are also provided by the present disclosure. In some embodiments, the expression vector further comprises the nucleotide sequence of a variable light ($V_L$) domain from a *lyssavirus*-specific (such as rabies virus-specific) monoclonal antibody. A cell comprising an expression vector disclosed herein is further provided. Also provided are monoclonal antibodies encoded by the expression vectors. A method of treating rabies in a subject by administering to the subject a monoclonal antibody expressed by an expressed vector disclosed herein is also provided.

The foregoing and other objects, features, and advantages of the invention will become more apparent from the following detailed description, which proceeds with reference to the accompanying figures.

SEQUENCE LISTING

Figure 1:
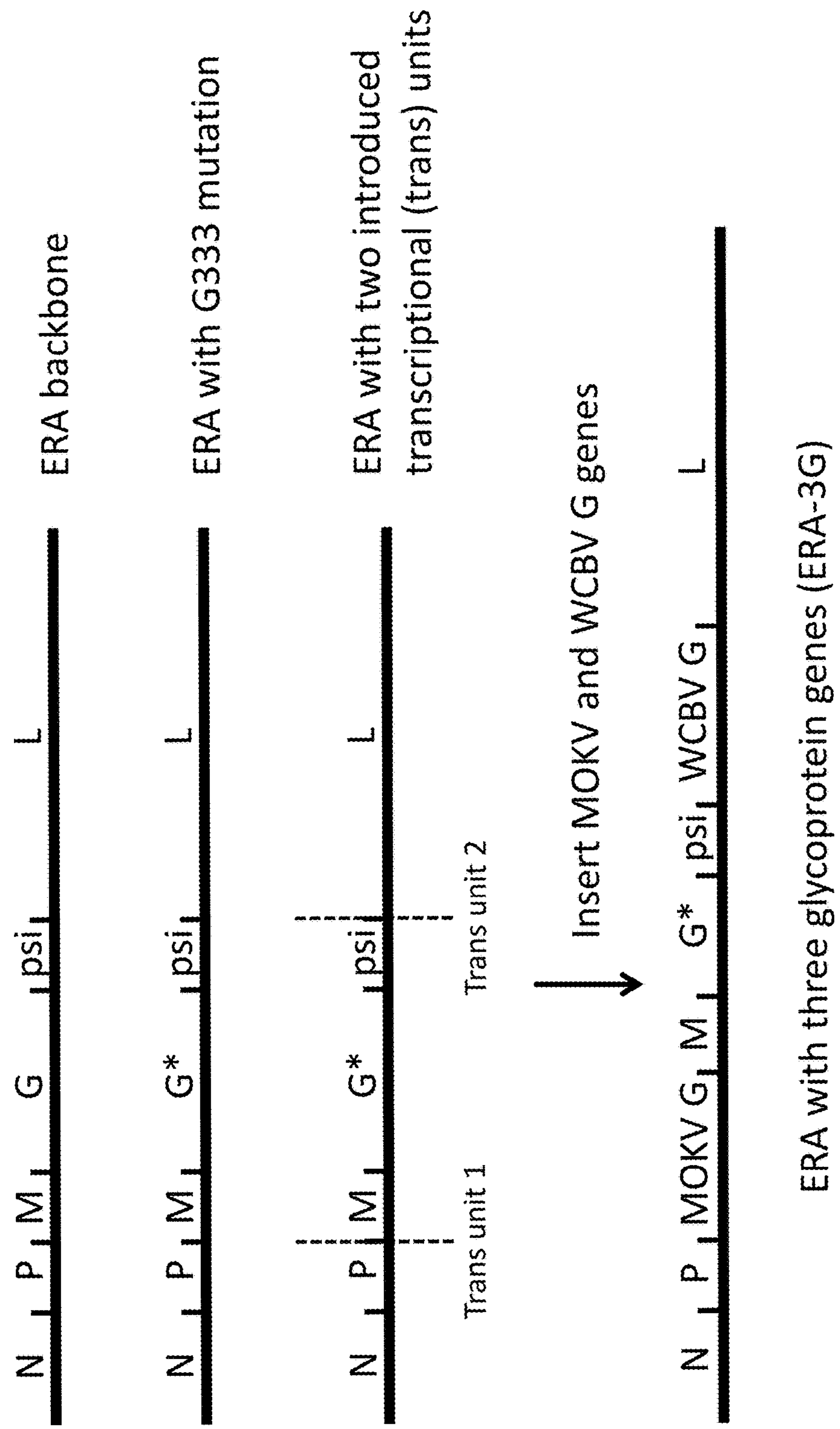
FIG. 1: Construction of ERA-3G. The G333 mutation is introduced into the ERA backbone and two transcriptional (trans) units are added. The transcriptional units are introduced between the P and M genes and between the G and L genes. The MOKV and WCBV G genes are cloned into the transcriptional units to form a recombinant ERA rabies virus with three glycoprotein genes (ERA-3G).

The nucleic acid and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Sep. 6, 2017, 103 KB, which is incorporated by reference herein. In the accompanying sequence listing:

SEQ ID NOs: 1-43 are the nucleotide sequences of human variable heavy ($V_H$) domain phage display clones selected using a recombinant ERA RABV expressing glycoprotein (G) from RABV, MOKV and WCBV.

SEQ ID NOs: 44-110 are the nucleotide sequences of human variable heavy ($V_H$) domain phage display clones identified by sequential selection on cells expressing LBV glycoprotein, cells expressing MOKV glycoprotein, cells expressing WCBV glycoprotein and cells expressing DUVV glycoprotein.

SEQ ID NOs: 111 and 112 are the nucleotide sequences of RT-PCR primers for amplification of the MOKV G gene.

SEQ ID NOs: 113 and 114 are the nucleotide sequences of RT-PCR primers for amplification of the WCBV G gene.

SEQ ID NO: 115 is the nucleotide sequence of MOKV G.

SEQ ID NO: 116 is the nucleotide sequence of WCBV G.

SEQ ID NO: 117 is the nucleotide sequence of a transcription unit for incorporating heterologous ORFs.

SEQ ID NO: 118 is the nucleotide sequence of LBV G.

SEQ ID NO: 119 is the nucleotide sequence of DUVV G.

DETAILED DESCRIPTION

I. Abbreviations

ABLV Australian bat *lyssavirus*
ARAV Aravan virus
BBLV Bokeloh bat *lyssavirus*
CDR complementarity determining region
dAb domain antibody
DUVV Duvenhage virus
EBLV-1 European bat *lyssavirus*-1
EBLV-2 European bat *lyssavirus*-2
ELISA enzyme-linked immunosorbent assay
ERA Evelyn-Rokitnicki-Abelseth
G glycoprotein
IRKV Irkut virus
KHUV Khujand virus
L RNA-dependent RNA polymerase
LBV Lagos bat virus
M matrix protein
mAb monoclonal antibody
MOKV Mokola virus
N nucleoprotein
P phosphoprotein
RABV rabies virus
RIG anti-rabies virus immunoglobulin
RNP ribonucleoprotein
RABV rabies virus RFFIT rapid fluorescent focus inhibition test
SHIBV Shimoni bat virus
$V_H$ variable heavy
$V_L$ variable light
WCBV West Caucasian bat virus II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administer: As used herein, administering a composition, such as an antibody, to a subject means to give, apply or bring the composition into contact with the subject. Administration can be accomplished by any of a number of routes, such as, for example, topical, oral, subcutaneous, intramuscular, intraperitoneal, intravenous, intrathecal and intramuscular.

Animal: Living multi-cellular vertebrate organisms, a category that includes, for example, mammals and birds. The term mammal includes both human and non-human mammals. The term "animal" includes both human and veterinary subjects, for example, humans, non-human primates, dogs, cats, horses, raccoons, bats, rats, mice, foxes, squirrels, opossum, coyotes, wolves and cows.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term "antibody" includes intact immunoglobulins as well as a number of well-characterized fragments. For instance, Fabs, Fvs, and single-chain Fvs (scFvs) that bind to target protein (or epitope within a protein or fusion protein) would also be specific binding agents for that protein (or epitope). These antibody fragments are as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) $(Fab')_2$, the fragment of the antibody obtained by treating whole antibody with the enzyme pepsin without subsequent reduction; (4) $F(ab')_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999).

Each heavy and light chain contains a constant region and a variable region (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs has been defined (see, Kabat et al., *Sequences of Proteins of Immunological Interest*, U.S. Department of Health and Human Services, 1991). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds a specific antigen will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies. As used herein "monoclonal antibodies" further includes antigen-binding fragments, such as Fv, scFv, dsFv or Fab fragments.

A "chimeric antibody" has framework residues from one species, such as human, and CDRs (which generally confer antigen binding) from another species, such as a murine antibody.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. All parts of a human immunoglobulin are substantially identical to corresponding parts of natural human immunoglobulin sequences.

Antibody binding affinity: The strength of binding between a single antibody binding site and a ligand (e.g., an antigen or epitope). The affinity of an antibody binding site X for a ligand Y is represented by the dissociation constant ($K_d$), which is the concentration of Y that is required to occupy half of the binding sites of X present in a solution. A smaller $K_d$ indicates a stronger or higher-affinity interaction between X and Y and a lower concentration of ligand is needed to occupy the sites. In general, antibody binding affinity can be affected by the alteration, modification and/or substitution of one or more amino acids in the epitope recognized by the antibody paratope. Binding affinity can be measured using any technique known in the art, such as end-point titration in an Ag-ELISA assay.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens.

Complementarity determining region (CDR): Amino acid sequences which together define the binding affinity and specificity of the natural Fv region of a native Ig binding site. The light and heavy chains of an Ig each have three CDRs, designated L-CDR1, L-CDR2, L-CDR3 and H-CDR1, H-CDR2, H-CDR3, respectively.

Effector molecule (EM): The portion of a chimeric molecule that is intended to have a desired effect on a cell or system or substance to which the chimeric molecule is targeted. The term effector molecule is interchangeable with effector moiety, therapeutic agent, diagnostic agent, and similar terms.

Therapeutic agents include such compounds as nucleic acids, proteins (including monoclonal antibodies and antigen-binding fragments of monoclonal antibodies), peptides, amino acids or derivatives, glycoproteins, radioisotopes, lipids, carbohydrates, recombinant viruses or toxins. Nucleic acid therapeutic and diagnostic moieties include antisense nucleic acids, derivatized oligonucleotides for covalent cross-linking with single or duplex DNA, and triplex forming oligonucleotides. Diagnostic agents or moieties include radioisotopes and other detectable labels. Detectable labels useful for such purposes are also well known in the art, and include radioactive isotopes such as 32P, $^{125}I$, and $^{131}I$, fluorophores, chemiluminescent agents, and enzymes.

Evelyn-Rokitnicki-Abelseth (ERA): The ERA strain of rabies virus was derived from the Street-Alabama-Dufferin (SAD) strain, first isolated from a rabid dog in Alabama (USA) in 1935. The ERA strain was derived after multiple passages of SAD rabies virus in mouse brains, baby hamster kidney (BHK) cells, and chicken embryos.

Framework region: Amino acid sequences interposed between CDRs (or hypervariable regions). Framework regions include variable light and variable heavy framework regions. Each variable domain comprises four framework regions, often referred to as FR1, FR2, FR3 and FR4. The framework regions serve to hold the CDRs in an appropriate orientation for antigen binding. Framework regions typically form 3-sheet structures.

Fusion partner: Refers to any molecule that is fused (such as covalently linked) to another molecule. In the context of the present disclosure, an immunoconjugate includes an antibody linked to a fusion partner. In some examples, the fusion partner is an effector molecule, a label (such as a detectable label), a heterologous polypeptide or a drug.

Fusion protein: A protein generated by expression of a nucleic acid sequence engineered from nucleic acid sequences encoding at least a portion of two different (heterologous) proteins. To create a fusion protein, the nucleic acid sequences must be in the same reading frame and contain no internal stop codons in that frame.

Immunoconjugate: A covalent linkage of a fusion partner, such as an effector molecule, label, heterologous polypeptide or other moiety, to an antibody or antigen binding fragment thereof. The linkage can be by chemical or recombinant means, for instance. In some cases, the linkage is chemical, wherein a reaction between the antibody moiety and the fusion partner has produced a covalent bond formed between the two molecules to form one molecule. A peptide linker (short peptide sequence) can optionally be included between the antibody and the effector molecule.

Inhibiting or treating a disease: Inhibiting the full development of a disease or condition, for example, in a subject who is at risk for a disease. One specific example of a disease is rabies. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Isolated: An "isolated" or "purified" biological component (such as a nucleic acid, peptide, protein, protein complex, antibody or particle) has been substantially separated, produced apart from, or purified away from other biological components in the cell of the organism in which the component naturally occurs, that is, other chromosomal and extra-chromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell, or other production vessel. Preferably, a preparation is purified such that the biological component represents at least 50%, such as at least 70%, at least 90%, at least 95%, or greater, of the total biological component content of the preparation.

Label: A detectable compound or composition that is conjugated directly or indirectly to another molecule to facilitate detection of that molecule. Specific, non-limiting examples of labels include fluorescent tags, enzymatic linkages, and radioactive isotopes.

*Lyssavirus*: A genus of viruses that is part of the Rhabdoviridae family within the order Mononegavirales (viruses with a single-stranded, negative sense genome). *Lyssaviruses* are the etiological agents of rabies encephalitis in warm-blooded animals and humans. *Lyssavirus* species include rabies virus (RABV; genotype 1), Lagos bat virus (LBV; genotype 2), Mokola virus (MOKV; genotype 3), Duvenhage virus (DUVV; genotype 4), European bat *lyssavirus*-1 (EBLV-1; genotype 5), European bat *lyssavirus*-2 (EBLV-2; genotype 6) Australian bat *lyssavirus* (ABLV; genotype 7) and six additional species isolated from bats: four in central Asia and Russia (Aravan virus—ARAV; Khujand virus—KHUV; Irkut virus—IRKV; and West Caucasian bat virus—WCBV), one in Africa (*Shimoni bat virus*—SHIBV) and one in Europe (*Bokeloh bat lyssavirus*—BBLV) (Kuzmin et al., *Emerg. Infect. Dis.* 14(12): 1887-1889, 2008; Weyer et al., *Epidemiol. Infect.* 136:670-678, 2007; Kuzmin et al., *Virus Res.* 149(2):197-210, 2010; Freuling et al., *Emerg. Infect. Dis.* 17(8):1519-22, 2011; Kuzmin and Rupprecht, "Bat rabies" *In* Rabies, 2$^{nd}$ Edition, New York, Academic Press, 2007, pages 259-307, Jackson and Wunner, eds.).

Neutralizing antibody: An antibody that is capable of protecting a subject (or cells) against infection.

ORF (open reading frame): A series of nucleotide triplets (codons) coding for amino acids without any termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame. If introns are present, the operably linked DNA sequences may not be contiguous.

Phage display: A method for the study of protein-protein, protein-peptide, and protein-DNA interactions that uses bacteriophages to connect proteins with the genetic information that encodes them. Antibody phage display libraries, and methods of generating such libraries, are well known in the art (see, for example, Famm et al., *J. Mol. Biol.* 376:926-931, 2008; Carmen and Jermutus, Brief Funct Genomic Proteomic 1(2):189-203, 2002; and U.S. Pat. Nos. 6,828,422 and 7,195,866). In the context of the present disclosure, an antibody phage display library is a library of any type of antigen-binding antibody fragment displayed on phage. In particular examples, the antibody phage display library is a $V_H$ domain phage display library, or a scFv phage display library. As used herein, a "naïve" antibody (or antibody domain) phage display library refers to a library constructed using subjects that have not been exposed to *lyssavirus*.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules, proteins or antibodies that bind these proteins, viruses or vectors, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues joined together through amide bonds. When the amino acids are alpha-amino acids, either the L-optical isomer or the D-optical isomer can be used, the L-isomers being preferred for many biological uses. The terms "polypeptide" or "protein" as used herein are intended to encompass any amino acid molecule and include modified amino acid molecules. The term "polypeptide" is specifically intended to cover naturally occurring proteins, as well as those which are recombinantly or synthetically produced. Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
|---|---|
| Ala | Ser |
| Arg | Lys |
| Asn | Gln, His |
| Asp | Glu |

-continued

| Original Residue | Conservative Substitutions |
|---|---|
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

Amino acids are typically classified in one or more categories, including polar, hydrophobic, acidic, basic and aromatic, according to their side chains. Examples of polar amino acids include those having side chain functional groups such as hydroxyl, sulfhydryl, and amide, as well as the acidic and basic amino acids. Polar amino acids include, without limitation, asparagine, cysteine, glutamine, histidine, selenocysteine, serine, threonine, tryptophan and tyrosine. Examples of hydrophobic or non-polar amino acids include those residues having nonpolar aliphatic side chains, such as, without limitation, leucine, isoleucine, valine, glycine, alanine, proline, methionine and phenylalanine. Examples of basic amino acid residues include those having a basic side chain, such as an amino or guanidino group. Basic amino acid residues include, without limitation, arginine, homolysine and lysine. Examples of acidic amino acid residues include those having an acidic side chain functional group, such as a carboxy group. Acidic amino acid residues include, without limitation aspartic acid and glutamic acid. Aromatic amino acids include those having an aromatic side chain group. Examples of aromatic amino acids include, without limitation, biphenylalanine, histidine, 2-napthylalananine, pentafluorophenylalanine, phenylalanine, tryptophan and tyrosine. It is noted that some amino acids are classified in more than one group, for example, histidine, tryptophan, and tyrosine are classified as both polar and aromatic amino acids. Additional amino acids that are classified in each of the above groups are known to those of ordinary skill in the art.

Substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Purified: The term “purified” does not require absolute purity; rather, it is intended as a relative term. Thus, for example, a purified peptide, protein, virus, or other active compound is one that is isolated in whole or in part from naturally associated proteins and other contaminants. In certain embodiments, the term “substantially purified” refers to a peptide, protein, virus or other active compound that has been isolated from a cell, cell culture medium, or other crude preparation and subjected to fractionation to remove various components of the initial preparation, such as proteins, cellular debris, and other components.

Rabies: A viral disease that causes acute encephalitis (inflammation of the brain) in warm-blooded animals. Rabies is zoonotic (transmitted by animals), most commonly by a bite from an infected animal but occasionally by other forms of contact. Rabies is almost frequently fatal if post-exposure prophylaxis is not administered prior to the onset of severe symptoms. Rabies is caused by viruses of the *Lyssavirus* genus.

Rabies virus (RABV or RV): A member of the Rhabdoviridae family having a non-segmented RNA genome with negative sense polarity. Rabies virus is the prototype of the *Lyssavirus* genus. The rabies virus Evelyn-Rokitnicki-Abelseth (ERA) strain is a strain derived from the Street-Alabama-Dufferin (SAD) strain, first isolated from a rabid dog in Alabama (USA) in 1935. The ERA strain was derived after multiple passages of SAD RABV in mouse brains, baby hamster kidney (BHK) cells, and chicken embryos. The complete genomic sequence of the ERA strain is disclosed in PCT Publication No. WO 2007/047459.

Recombinant: A recombinant nucleic acid, protein or virus is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques. In some embodiments, recombinant rabies virus is generated using reverse genetics, such as the reverse genetics system described in PCT Publication No. WO 2007/047459. In some examples, the recombinant rabies viruses comprise one or more mutations in a viral virulence factors, such as glycoprotein. In other examples, the recombinant rabies viruses comprise a heterologous gene, such as a sequence encoding a glycoprotein from another *lyssavirus* (such as Mokola virus, West Caucasian bat virus or Lagos bat virus).

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (*Adv. Appl. Math.,* 2:482, 1981); Needleman and Wunsch (*J. Mol. Biol.,* 48:443, 1970); Pearson and Lipman (*Proc. Natl. Acad. Sci.,* 85:2444, 1988); Higgins and Sharp (*Gene,* 73:237-44, 1988); Higgins and Sharp (*CABIOS,* 5:151-53, 1989); Corpet et al. (*Nuc. Acids Res.,* 16:10881-90, 1988); Huang et al. (*Comp. Appls. Biosci.,* 8:155-65, 1992); and Pearson et al. (*Meth. Mol. Biol.,* 24:307-31, 1994). Altschul et al. (*Nature Genet.,* 6:119-29, 1994) presents a detailed consideration of sequence alignment methods and homology calculations.

The alignment tools ALIGN (Myers and Miller, *CABIOS* 4:11-17, 1989) or LFASTA (Pearson and Lipman, 1988) may be used to perform sequence comparisons (Internet Program© 1996, W. R. Pearson and the University of Virginia, “fasta20u63” version 2.0u63, release date December 1996). ALIGN compares entire sequences against one another, while LFASTA compares regions of local similarity. These alignment tools and their respective tutorials are available on the Internet at the NCSA website. Alternatively, for comparisons of amino acid sequences of greater than about 30 amino acids, the "Blast 2 sequences" function can be employed using the default BLOSUM62 matrix set to default parameters, (gap existence cost of 11, and a per residue gap cost of 1). When aligning short peptides (fewer than around 30 amino acids), the alignment should be performed using the "Blast 2 sequences" function, employing the PAM30 matrix set to default parameters (open gap 9, extension gap 1 penalties). The BLAST sequence comparison system is available, for instance, from the NCBI web site; see also Altschul et al., *J. Mol. Biol.,* 215:403-10, 1990; Gish and States, *Nature Genet.,* 3:266-72, 1993; Madden et al., *Meth. Enzymol.,* 266:131-41, 1996; Altschul et al., *Nucleic Acids Res.,* 25:3389-402, 1997; and Zhang and Madden, *Genome Res.,* 7:649-56, 1997.

Orthologs (equivalent to proteins of other species) of proteins are in some instances characterized by possession of greater than 75% sequence identity counted over the full-length alignment with the amino acid sequence of specific protein using ALIGN set to default parameters. Proteins with even greater similarity to a reference sequence will show increasing percentage identities when assessed by this method, such as at least 80%, at least 85%, at least 90%, at least 92%, at least 95%, or at least 98% sequence identity. In addition, sequence identity can be compared over the full length of one or both binding domains of the disclosed fusion proteins.

When significantly less than the entire sequence is being compared for sequence identity, homologous sequences will typically possess at least 80% sequence identity over short windows of 10-20, and may possess sequence identities of at least 85%, at least 90%, at least 95%, or at least 99% depending on their similarity to the reference sequence. Sequence identity over such short windows can be determined using LFASTA; methods are described at the NCSA website. One of skill in the art will appreciate that these sequence identity ranges are provided for guidance only; it is entirely possible that strongly significant homologs could be obtained that fall outside of the ranges provided. Similar homology concepts apply for nucleic acids as are described for protein. An alternative indication that two nucleic acid molecules are closely related is that the two molecules hybridize to each other under stringent conditions.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Subject: Living multi-cellular vertebrate organisms, a category that includes both human and non-human mammals.

Therapeutically effective amount: A quantity of a specified agent sufficient to achieve a desired effect in a subject being treated with that agent. For example, this may be the amount of a *lyssavirus*-specific monoclonal antibody useful for treating rabies. The effective amount of a *lyssavirus*-specific monoclonal antibody useful for treating rabies in a subject will be dependent on, for example, the subject being treated, the manner of administration of the composition, and other factors.

Vector: A nucleic acid molecule that can be introduced into a host cell, thereby producing a transformed host cell. A vector may include nucleic acid sequences that permit it to replicate in a host cell, such as an origin of replication (DNA sequences that participate in initiating DNA synthesis). A vector may also include one or more selectable marker genes and other genetic elements known in the art. In some embodiments herein, the vector is an Fc IgG expression vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Currently available anti-rabies immunoglobulins do not neutralize *lyssaviruses* of other genotypes, such as Lagos bat virus (LBV), Mokola virus (MOKV), and West Caucasian bat virus (WCBV). The use of immunized humans for immune library construction biases libraries towards neutralization of genotype 1 rabies viruses with lower cross-reactivity towards other genotypes. To circumvent this limitation, disclosed herein is the use of a naïve human phage display library to identify and characterize novel monoclonal antibodies (mAbs) that broadly neutralize *lyssaviruses*. As described in Examples 2 and 3 below, this library displays variable heavy ($V_H$) domain antibodies (dAbs) with diversity added to the complementarity determining regions (CDR). Antibodies identified by the methods provided herein can be used, for example, for post-exposure rabies prophylaxis or in the treatment of clinical rabies.

Provided herein is a method of identifying a monoclonal antibody or antigen-binding fragment thereof that specifically binds at least two different *lyssaviruses*. In some embodiments, the method includes screening a naïve antibody phage display library with at least two different *lyssavirus* glycoproteins, such as by screening the library against a recombinant virus expressing at least two different *lyssavirus* glycoproteins, screening the library against recombinant glycoprotein from at least two different *lyssaviruses*, screening the library against cells expressing at least two different *lyssavirus* glycoproteins, or any combination thereof. In some embodiments, the method further includes selecting a phage display clone that specifically binds to at least two different *lyssaviruses*, at least two different *lyssavirus* glycoproteins, or both.

The at least two different *lyssaviruses* can be selected from any known *lyssavirus*, such as, for example, rabies virus (RABV), Mokola virus (MOKV), West Caucasian bat virus (WCBV), Lagos bat virus (LBV), Duvenhage virus (DUVV), European bat *lyssavirus*-1 (EBLV-1), European bat *lyssavirus*-2 (EBLV-2), Australian bat *lyssavirus* (ABLV), Aravan virus (ARAV), Khujand virus (KHUV) and Irkut virus (IRKV). In some embodiments, the antibody or antigen-binding fragment specifically binds at least three, at least four or at least five different *lyssaviruses*, or at least three, at least four or at least five different *lyssavirus* glycoproteins.

In particular embodiments, the method includes screening a naïve antibody phage display library with (1) a recombinant rabies virus expressing glycoprotein from RABV, MOKV and WCBV; (2) at least two different recombinant *lyssavirus* glycoproteins selected from the RABV glycoprotein, the MOKV glycoprotein, the WCBV glycoprotein, the LBV glycoprotein and the DUVV glycoprotein; or (3) at least two different cell lines expressing a *lyssavirus* glycoprotein selected from the RABV glycoprotein, the MOKV glycoprotein, the WCBV glycoprotein, the LBV glycoprotein and the DUVV glycoprotein; and selecting a phage display clone that specifically binds to at least two different *lyssaviruses*, at least two different *lyssavirus* glycoproteins, or both. In some examples, the at least two different *lyssaviruses* are selected from RABV, MOKV, WCBV, LBV and DUVV. In particular non-limiting examples, the antibody or antigen-binding fragment specifically binds whole virus and/or glycoprotein of RABV, MOKV and WCBV; RABV, MOKV, WCBV and LBV; RABV, MOKV, WCBV, LBV and DUVV; or MOKV, WCBV, LBV and DUVV.

In some embodiments, the phage display library is a naïve human $V_H$ domain library. In other embodiments, the phage display library is a naïve human scFv library or a naïve human Fab library. However, other naïve human antibody libraries can be used and an appropriate library can be selected by one of skill in the art.

In some embodiments, the antigen-binding fragment comprises a $V_H$ domain. In other embodiments, the antigen-binding fragment comprises a scFV. In yet other embodiments, the antigen-binding fragment comprises an Fab.

In some embodiments, the method further includes cloning the antigen-binding fragment (for example, a fragment comprising a $V_H$ domain, a scFV or a Fab) into an Fc IgG expression vector to generate an immunoglobulin molecule containing the fragment (such as an Fc IgG1 expression vector, for example pNUT-Cγ1 (Boel, et al., *J. Immunol. Methods*. 239:153-166, 2000)). In some examples, the Fc IgG expression vector further includes nucleic acid sequence encoding a variable light ($V_L$) domain from a rabies virus-specific antibody.

Selecting a phage display clone that specifically binds to a *lyssavirus* (for example, whole virus) or *lyssavirus* glycoprotein can be performed using any assay known in the art for evaluating antigen binding. In some embodiments, the selecting step includes an ELISA to detect specific binding to *lyssavirus* glycoprotein, whole virus, or both.

In some embodiments, the method further includes screening the phage display clone for *lyssavirus* neutralization. Assays for evaluating virus neutralization are well known in the art and include, for example, fluorescent focus assays, including the rapid fluorescent focus inhibition test (RFFIT).

Also provided are isolated monoclonal antibodies, and antigen-binding fragments thereof, identified according to the methods disclosed herein. In some embodiments, the antibody neutralizes infectivity of the *lyssaviruses*.

In some embodiments, the $V_H$ domain of the antibody is encoded by a nucleotide sequence at least 85%, at least 90%, at least 95%, at least 96%, at least 97%, at least 98% or at least 99% identical to any one of SEQ ID NOs: 1-110. In some examples, the $V_H$ domain of the antibody is encoded by a nucleotide sequence comprising any one of SEQ ID NOs: 1-110.

In some embodiments, any in-frame "TAG" (stop codons) in the $V_H$ domain sequence are changed to "GAG" (glutamate codons) to allow expression in eukaryotic cells.

SEQ ID NOs: 1-43 show the nucleotide sequences of 43 different clones of a naïve human $V_H$ domain library that were selected using a recombinant rabies virus expressing glycoprotein from RABV, MOKV and WCBV. These clones bind whole virus and/or bind glycoprotein from RABV, MOKV and WCBV. Each clone includes nucleic acid sequence encoding the $V_H$ complementarity determining regions (CDRs). Identifying CDR sequences of an antibody or antibody fragment, given the nucleotide or amino acid sequence of the antibody or antibody fragment, is within the capabilities of one of skill in the art, such as by using the Kabat method (see, Kabat et al., Sequences of Proteins of Immunological Interest, U.S. Department of Health and Human Services, 1991; the Kabat database is now maintained online) or the International ImMunoGeneTics Information System™ (IMGT, available online). Thus, also provided herein is a monoclonal antibody, or antigen-binding fragment thereof, comprising at least one CDR sequence, such as two CDR sequences or all three CDR sequences, encoded by a portion of any one of SEQ ID NOs: 1-43.

SEQ ID NOs: 44-110 represent the nucleotide sequences of 67 different clones of a naïve human $V_H$ domain library that were selected by sequential panning on cell lines expressing glycoprotein from LBV, MOKV, WCBV and DUVV. CDR1, CDR2 and CDR3 sequences of each $V_H$ domain clone are provided in Table 2. Thus, provided herein is a monoclonal antibody, or antigen-binding fragment thereof, comprising at least one, at least two or all three CDR sequences from any one of SEQ ID NOs: 44-110.

Also provided is an isolated monoclonal antibody, or antigen-binding fragment thereof, that specifically binds at least two different *lyssaviruses*; or that specifically binds recombinant glycoprotein from at least two different *lyssaviruses*. In some embodiments, the $V_H$ domain of the antibody is encoded by a nucleotide sequence at least 85%, at least 90%, at least 95%, at least 96%, at least 97%, at least 98% or at least 99% identical to the nucleotide sequence of any one of SEQ ID NOs: 1-110. In some embodiments, the $V_H$ domain of the antibody is encoded by a nucleotide sequence comprising any one of SEQ ID NOs: 1-110. In some embodiments, the at least two *lyssaviruses* are selected from RABV, MOKV, WCBV, LBV and DUVV. In some examples, the isolated monoclonal antibody specifically binds RABV, MOKV and WCBV; or specifically binds recombinant glycoprotein from RABV, MOKV and WCBV. In other examples, the isolated monoclonal antibody specifically binds RABV, MOKV, WCBV and LBV; or specifically binds recombinant glycoprotein from RABV, MOKV, WCBV and LBV. In other examples, the isolated monoclonal antibody specifically binds RABV, MOKV, WCBV, LBV and DUVV; or specifically binds recombinant glycoprotein from RABV, MOKV, WCBV, LBV and DUVV. In yet other examples, the isolated monoclonal antibody specifically binds MOKV, WCBV, LBV and DUVV; or specifically binds recombinant glycoprotein from MOKV, WCBV, LBV and DUVV. In particular examples, the antibody neutralizes infectivity of the *lyssaviruses*.

In some embodiments, the monoclonal antibody comprises a $V_L$ domain from a rabies virus-specific antibody.

In some embodiments disclosed herein, the antibody is an IgG. In other embodiments, the antibody is an IgM. In some embodiments, the antibody is a human antibody or a humanized antibody. In some embodiments, the antibody is a Fab fragment, a Fab' fragment, a $F(ab)'_2$ fragment, a single chain Fv protein (scFv), or a disulfide stabilized Fv protein (dsFv).

Further provided herein is an isolated immunoconjugate comprising a monoclonal antibody disclosed herein and a fusion partner. In some embodiments, the fusion partner is an effector molecule, a label or a heterologous polypeptide.

Also provided are compositions comprising the monoclonal antibodies or immunoconjugates disclosed herein and a pharmaceutically acceptable carrier.

Compositions comprising more than one type of anti-rabies antibody are also provided herein. In some embodiments, the composition includes (1) a monoclonal antibody that specifically binds at least two *lyssaviruses* as disclosed herein, and (2) a monoclonal antibody specific for RABV or RABV glycoprotein. In some embodiments, the composition further comprises a pharmaceutically acceptable carrier.

Further provided is an isolated nucleic acid molecule encoding any one of the monoclonal antibodies disclosed herein.

Also provided is a method of treating rabies in a subject, comprising administering to the subject a monoclonal antibody or antigen-binding fragment thereof, an immunoconjugate or a composition disclosed herein.

Also provided herein is an expression vector comprising a nucleotide sequence at least 85%, at least 90%, at least 95%, at least 96%, at least 97%, at least 98% or at least 99% identical to the nucleotide sequence of any one of SEQ ID NOs: 1-110. In some embodiments, the expression vector comprises the nucleotide sequence of any one of SEQ ID NOs: 1-110. In some embodiments, the expression vector further comprises the nucleotide sequence of a $V_L$ domain from a *lyssavirus*-specific monoclonal antibody. In particular examples, the $V_L$ domain is from a RABV-specific monoclonal antibody. In some embodiments, the expression vector is an Fc IgG expression vector. A cell comprising an expression vectors disclosed herein is also provided. Further provided is a monoclonal antibody encoded by the Fc IgG expression vector. A monoclonal antibody expressed from such an Fc IgG expression vector can be used for rabies prophylaxis and clinical rabies treatment.

IV. *Lyssavirus*

The genus *Lyssavirus* is a member of the Rhabdoviridae family within the order Mononegavirales (viruses with a single-stranded, negative sense genome). *Lyssaviruses* are the etiological agents of rabies encephalitis in warm-blooded animals and humans (Tordo et al., "*Lyssaviruses*" In Fauquet et al. eds. *Virus taxonomy: the classification and nomenclature of viruses. The 8th Report of the International Committee on Taxonomy of Viruses*. San Diego: Oxford Academic, 2006, pages 623-629; World Health Organization Expert Consultation on Rabies, 5-8 October 2004, first report, World Health Organization Technical report series 931, Geneva: World Health Organization, 2005, pages 15-19). *Lyssavirus* species include rabies virus (RABV; genotype 1), Lagos bat virus (LBV; genotype 2), Mokola virus (MOKV; genotype 3), Duvenhage virus (DUVV; genotype 4), European bat *lyssavirus*-1 (EBLV-1; genotype 5), European bat *lyssavirus*-2 (EBLV-2; genotype 6), Australian bat *lyssavirus* (ABLV; genotype 7) six additional species isolated from bats: four in central Asia and Russia (Aravan virus—ARAV; Khujand virus—KHUV; Irkut virus—IRKV; and West Caucasian bat virus—WCBV), one in Africa (*Shimoni bat virus*—SHIBV) and one in Europe (*Bokeloh bat lyssavirus*—BBLV) (Kuzmin et al., *Emerg. Infect. Dis.* 14(12): 1887-1889, 2008; Weyer et al., *Epidemiol. Infect.* 136:670-678, 2007; Kuzmin et al., *Virus Res.* 149(2):197-210, 2010; Freuling et al., *Emerg. Infect. Dis.* 17(8):1519-22, 2011; Kuzmin and Rupprecht, "Bat rabies" *In Rabies, 2nd* Edition, New York, Academic Press, 2007, pages 259-307, Jackson and Wunner, eds.).

Based on phylogeny, immunogenicity and virulence of *lyssavirus* isolates, two *lyssavirus* phylogroups have been proposed (Badrane et al., *J. Virol.* 75:3268-3276, 2001). The division into phylogroups generally correlates with the pattern of vaccine cross-protection observed for *lyssaviruses* (Badrane et al., *J. Virol.* 75:3268-3276, 2001; Hanlon et al., *Virus Res.* 111:44-54, 2005; Nel et al., *Expert Rev. Vaccines* 4:553-540, 2005). Phylogroup1 includes genotypes 1, 4, 5, 6 and 7, as well as ARAV, KHUV IRKV and BBLV (Kuzmin et al., *Virus Res.* 97:65-79, 2003; Kuzmin et al., *Virus Res.* 111:28-43, 2005; Hanlon et al., *Virus Res.* 111:44-54, 2005; Freuling et al., *Emerg. Infect. Dis.* 17(8):1519-22, 2011). Currently available commercial vaccines and biologicals are considered to be effective against infections of viruses from this phylogroup (Nel et al., *Expert Rev. Vaccines* 4:553-540, 2005). However, these vaccines and biologics for rabies do not offer full protection against infection with viruses outside of *lyssavirus* phylogroup 1 (i.e., genotypes 2, 3 and SHIBV). In addition, WCBV is recognized as the most divergent *lyssavirus* and exhibits limited relatedness to genotype 2 and 3 viruses. Previous studies have demonstrated little or no cross-neutralization of anti-RABV sera with WCBV (Botvinkin et al., *Emerg. Infect. Dis.* 9:1623-1625, 2003; Hanlon et al., *Virus Res.* 111:44-54, 2005).

*Lyssaviruses* are composed of two major structural components, a nucleocapsid or ribonucleoprotein (RNP), and an envelope in the form of a bilayer membrane surrounding the RNP core. The infectious component of all rhabdoviruses is the RNP core, which consists of the negative strand RNA genome encapsidated by nucleoprotein (N) in combination with RNA-dependent RNA-polymerase (L) and phosphoprotein (P). The membrane surrounding the RNP contains two proteins, the trans-membrane glycoprotein (G) and the matrix (M) protein, located at the inner side of the membrane. Thus, the viral genome codes for these five proteins: the three proteins in the RNP (N, L and P), the matrix protein (M), and the glycoprotein (G).

The molecular determinants of pathogenicity of various rabies virus strains have not been fully elucidated. RABV pathogenicity was attributed to multigenic events (Yamada et al., *Microbiol. Immunol.* 50:25-32, 2006). For example, some positions in the RABV genome if mutated, affect viral transcription or replication, reducing virulence. Mutations at serine residue 389 of the phosphorylation site in the N gene (Wu et al., *J. Virol.* 76:4153-4161, 2002) or GDN core sequence of the highly conserved C motif in the L gene (Schnell and Conzelmann, *Virol.* 214:522-530, 1995) dramatically reduced RABV transcription and replication.

The G protein, also referred to as spike protein, is involved in cell attachment and membrane fusion of RABV. The amino acid region at position 330 to 340 (referred to as antigenic site III) of the G protein has been identified as important for virulence of certain strains of RABV. Several studies support the concept that the pathogenicity of fixed RABV strains is determined by the presence of arginine or lysine at amino acid residue 333 of the glycoprotein (Dietzschold et al., *Proc. Natl. Acad. Sci. USA* 80: 70-74, 1983; Tuffereau et al., *Virology* 172: 206-212, 1989).

This phenomenon seems to apply at least to fixed rabies viruses such as CVS, ERA, PV, SAD-B19 and HEP-Flury strains (Anilionis et al., *Nature* 294:275-278, 1981; Morimoto et al., *Virology* 173:465-477, 1989). For example, rabies vaccine viruses possessing an amino acid differing from Arg at position 333 of the glycoprotein are described, for instance, in PCT Publication No. WO 00/32755 (describing RABV mutants in which all three nucleotides in the G protein $Arg_{333}$ codon are altered compared to the parent virus, such that the Arg at position 333 is substituted with another amino acid); European Patent No. 350398 (describing an avirulent RABV mutant SAG1 derived from the Bern SAD strain of RABV, in which the Arg at position 333 of the glycoprotein has been substituted to Ser); and European patent application 583998 (describing an attenuated RABV mutant, SAG2, in which the Arg at position 333 in the G protein has been substituted by Glu).

Other strains, such as the RC-HL strain, possess an arginine residue at position 333 of the G, but do not cause lethal infection in adult mice (Ito et al., *Microl. Immunol.* 38:479-482, 1994; Ito et al., *J. Virol.* 75:9121-9128, 2001). As such, the entire G may contribute to the virulence of RABV, although the determinants or regions have not been fully elucidated.

The G gene encodes the only protein that induces viral neutralizing antibody. At least three states of RABV glycoprotein are known: the native state (N) being responsible for receptor binding; an active hydrophobic state (A) necessary in the initial step in membrane fusion process (Gaudin, J. *Cell Biol.* 150:601-612, 2000), and a fusion inactive conformation (I). Correct folding and maturation of the G protein play important roles for immune recognition. The three potential glycosylated positions in ERA G extracellular domain occur at $Asn^{37}$, $Asn^{247}$ and $Asn^{319}$residues (Wojczyk et al., *Glycobiology.* 8: 121-130, 1998). Nonglycosylation of G not only affects conformation, but also inhibits presentation of the protein at the cell surface.

V. Antibody Compositions and Therapeutic Methods

Standard treatment for post-exposure rabies prophylaxis includes thorough wound-washing with soap and water followed by administration of vaccine and anti-rabies virus immunoglobulin (RIG) of human or equine origin. RIG administered shortly after exposure at the wound site provides passive immunity which neutralizes rabies virus and prevents its spread until the patient's immune response following vaccination is elicited. Deaths due to post-exposure prophylaxis failure are most commonly attributed to deviations from the recommended regimen such as late initiation of post-exposure prophylaxis or no administration of RIG (Wilde, *Vaccine,* 25:7605-7609, 2007). Provided herein are human monoclonal antibodies that specifically bind at least two different *lyssaviruses*. Thus, the disclosed antibodies are useful for the treatment of clinical rabies and/or for post-exposure rabies prophylaxis.

Compositions are provided that include a monoclonal antibody, or antigen-binding fragment thereof, that specifically binds at least two different *lyssaviruses* (such as whole virus or *lyssavirus* glycoprotein, or both). Compositions comprising immunoconjugates or immunotoxins are also provided. The compositions can be prepared in unit dosage forms for administration to a subject. The amount and timing of administration are at the discretion of the treating physician to achieve the desired purposes. For example, the compositions can be administered to a subject exhibiting clinical signs of rabies, or can be administered to a subject that has been exposed to or bitten by a rabid animal (or an animal suspected of being rabid). The antibody can be formulated for systemic or local (such as at a wound site) administration.

The compositions for administration can include a solution of the antibody (or antigen-binding fragment thereof) that specifically binds *lyssavirus* dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

Doses of *lyssavirus* mAb generally range from about 1 to about 50 IU/kg, such as about 5 to about 40 IU/kg, or about 5 to about 20 IU/kg. In particular examples, the dose is about 5 IU/kg, about 10 IU/kg or about 20 IU/kg. However, the dose of *lyssavirus* mAb will vary depending upon the antibody (or antibody cocktail) selected and the particular subject to be treated. An appropriate does can be determined by a medical practitioner.

Actual methods for preparing administrable compositions will be known or apparent to those skilled in the art and are described in more detail in such publications as *Remington's Pharmaceutical Science,* 19th ed., Mack Publishing Company, Easton, Pa. (1995).

Antibodies may be provided in lyophilized form and rehydrated with sterile water before administration, although they are also provided in sterile solutions of known concentration. Antibodies can be administered by slow infusion, or by intravenous push or bolus. Antibody compositions can also be administered topically.

The antibody that specifically binds *lyssavirus* can be administered to prevent the development of rabies disease and/or slow the spread of *lyssavirus* from a wound site to distant sites in the body. In these applications, a therapeutically effective amount of an antibody is administered to a subject in an amount sufficient to inhibit virus replication or spread, or to inhibit a sign or a symptom of rabies. Suitable subjects may include those diagnosed with rabies, or subjects recently exposed to (such as bitten by) animal infected with a *lyssavirus*, or suspected of being infected with a *lyssavirus*.

A therapeutically effective amount of a *lyssavirus*-specific antibody will depend upon the severity of the disease and the general state of the patient's health. A therapeutically effective amount of the antibody is that which provides either subjective relief of a symptom(s) or an objectively identifiable improvement as noted by the clinician or other qualified observer. These compositions can be administered in conjunction with other therapeutic agents (such as a rabies vaccine), either simultaneously or sequentially.

Single or multiple administrations of the compositions are administered depending on the dosage and frequency as required and tolerated by the patient. In any event, the composition should provide a sufficient quantity of at least one of the antibodies disclosed herein to effectively treat the patient. The dosage can be administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

The following examples are provided to illustrate certain particular features and/or embodiments. These examples should not be construed to limit the disclosure to the particular features or embodiments described.

EXAMPLES

Example 1: Construction and Characterization of Recombinant *Rabies Virus* with Three Glycoprotein Genes This example describes the generation and characterization of a recombinant ERA strain rabies virus encoding three different glycoprotein genes. The recombinant virus, referred to as ERA-3G, comprises rabies virus (RABV) glycoprotein, Mokola virus (MOKV) glycoprotein and West Caucasian bat virus (WCBV) glycoprotein. The cloning strategy for ERA-3G is shown in FIG. 1. The rabies virus reverse genetics system used to generate this virus in described in detail in PCT Publication No. WO 2007/047459. ERA-3G includes the attenuating mutation in the RABV glycoprotein gene that results in an arginine to glutamic acid change at amino acid residue 333 of the protein.

The G genes from MOKV and WCBV were cloned into the ERA backbone (see SEQ ID NO: 7 of PCT Publication No. WO 2007/047459) by RT-PCR using viral genomic RNA from virus-infected cells as template. The following primers were used for amplification of the glycoprotein genes:

```
MokolaG5-
                                        (SEQ ID NO: 111)
CGACTGCAGATGAATATACCTTGCTTTGTTGTGATTC

MokolaG3-
                                        (SEQ ID NO: 112)
CGTGGTACCTCATGTACCTGGAAGCCCTTTATAGGACTC

WCBVG5-
                                        (SEQ ID NO: 113)
CATCTGCTAGCAATGGCTTCCTACTTTGCGTTG

WCBVG3-
                                        (SEQ ID NO: 114)
TTCAATGGTACCTTATTGGGCAGTTTGTCCCTT
```

The amplified G genes for MOKV (SEQ ID NO: 115) and WCBV (SEQ ID NO: 116) were confirmed by sequencing. Two extra transcription units were synthesized (each with the sequence of SEQ ID NO: 117) and introduced into the gene junctions between the phosphoprotein (P) and the matrix protein (M), and the G and the RNA dependent RNA polymerase (L) (FIG. 1). The MOKV G was cloned into the gene junction between the P and M, and WCBV G into the gene junction between the G and L in the ERA genome backbone.

Recombinant virus was recovered by transfection of the above described construct into BSR cells using the method described in PCT Publication No. WO 2007/047459.

Example 2: Identification of Domain Antibodies Specific for *Lyssaviruses*

Current anti-rabies immune globulins do not neutralize all *lyssaviruses*. The use of immunized humans for immune library construction biases libraries towards neutralization of RABV genotype 1 with lower cross-reactivity towards other *Lyssavirus* genotypes. One method to circumvent this limitation is selecting monoclonal antibodies (mAbs) from naïve immune libraries, which theoretically contain binders to any antigen.

This example describes the use of a naïve, human-heavy domain, phage display library (Famm et al., *J. Mol. Biol.* 376:926-931, 2008) to identify and characterize novel anti-*Lyssavirus* mAbs. The phage display library ($3\times10^9$ clones) is based on human $V_H$ framework with diversity introduced into CDR1, CDR2 and CDR3 by PCR mutagenesis. The library was panned using a recombinant ERA RABV expressing three different G proteins (see Example 1)—the G proteins from rabies virus (RABV), Mokola virus (MOKV) and West Caucasian Bat virus (WCBV)—following established methods (Kramer et al., Eur. *J. Immunol.* 35:2131-2145, 2005; Lee et al., *Nat. Protoc.* 2:3001-3008, 2007).

Library Panning

For the first two times the library was panned, either purified G protein or whole virus was used to select binders for three rounds and then switched antigens for three more rounds so that binders selected for G protein were then panned against whole virus and vice versa. After the last round of selection, 552 individual clones were picked (276 from each panning scheme) and potential high affinity domain antibodies (dAb) were identified by ELISA.

ELISA

The ELISA procedure was standardized using the soluble dAb fragments from these clones and the same antigens used to pan the library. Approximately 5-10% of selected clones bind to the original antigen and 2-3% bind to the secondary antigen (Table 1).

TABLE 1

Results of Panning Phage Display Library

| Scheme | Screened | Binding* whole virus | Binding* G protein |
|---|---|---|---|
| Whole virus→G Protein | 276 | 30 (10.9%) | 4 (1.4%) |
| G Protein→Whole virus | 276 | 8 (2.9%) | 13 (4.7%) |
| Total | 552 | 38 (6.9%) | 17 (3.1%) |

Figure 2:
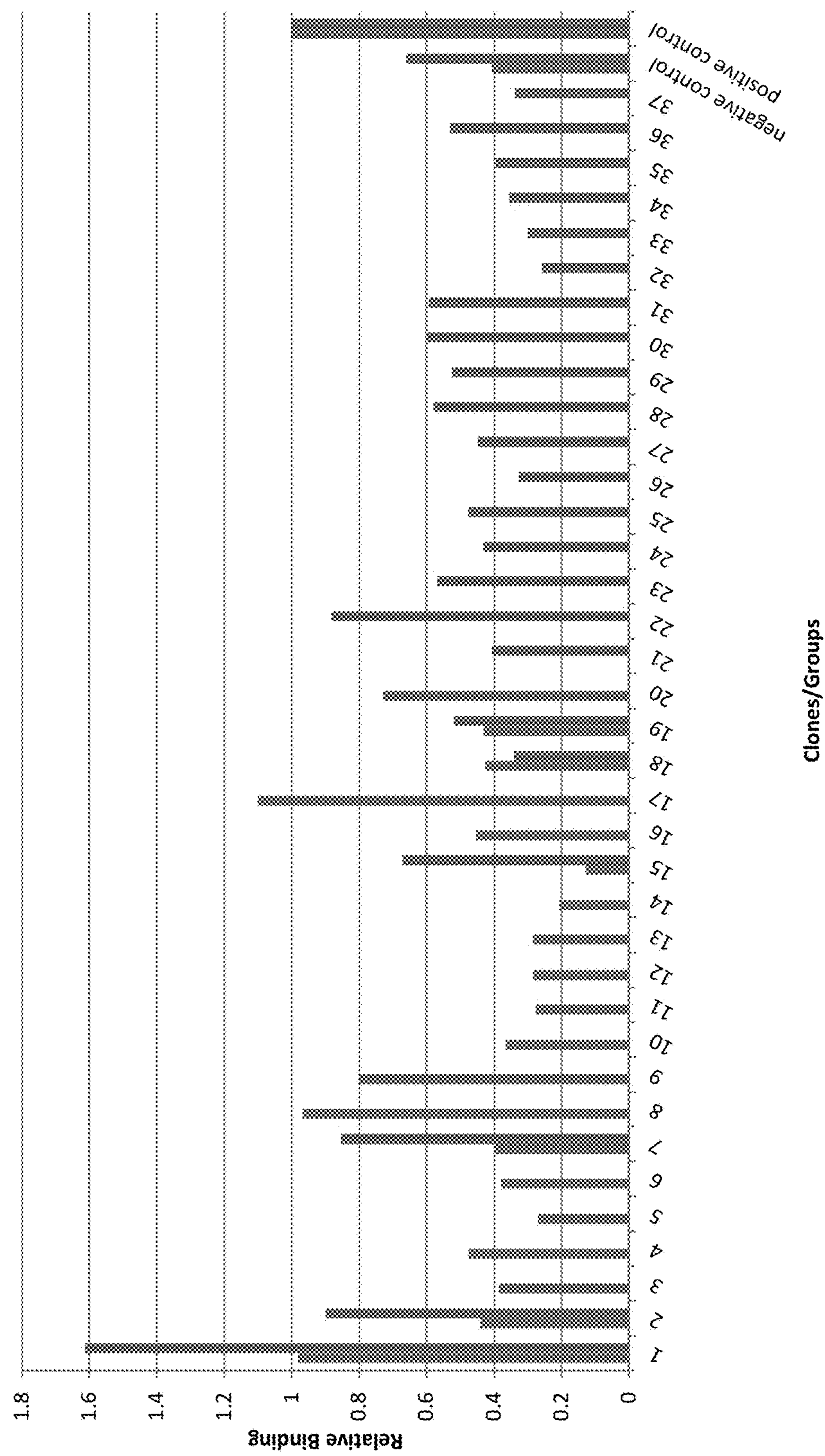
FIG. 2: Results of whole virus ELISA. Relative binding of selected human variable heavy ($V_H$) domain phage display clones to recombinant ERA RABV expressing glycoprotein (G) from RABV, MOKV and WCBV. The left bar for each clone shown indicates clones selected using the whole recombinant virus ERA RABV expressing glycoprotein (G) from RABV, MOKV and WCBV. The right bar for each clone shown indicates clones selected using glycoproteins purified from the recombinant ERA RABV expressing glycoprotein (G) from RABV, MOKV and WCBV. Using a standard ELISA method, raw absorbance (420 nm-650 nm) was fixed relative to a known clone binding to its cognate antigen (positive control).
Figure 3:
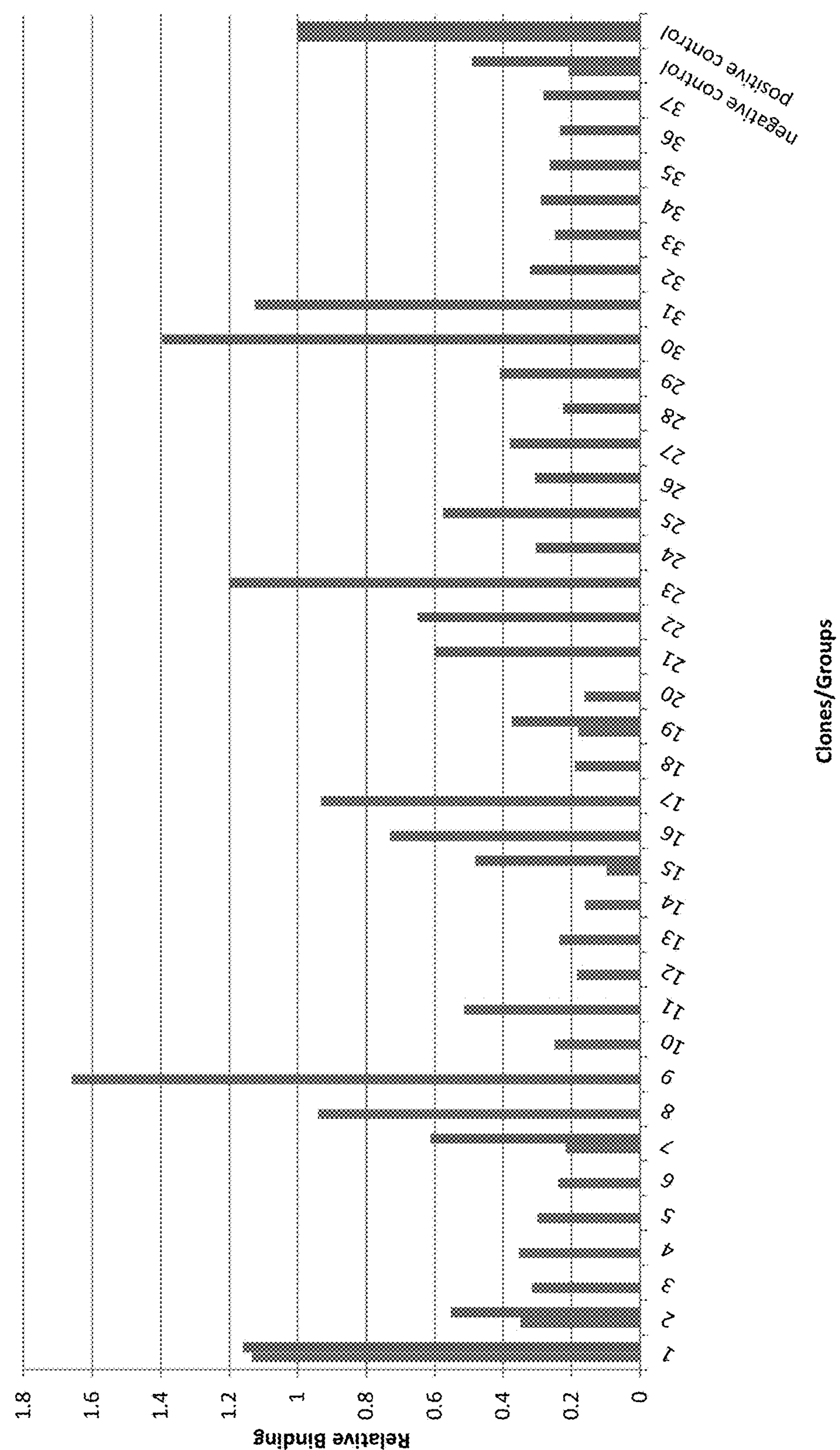
FIG. 3: Results of glycoprotein ELISA. Relative binding of selected human variable heavy ($V_H$) domain phage display clones to glycoproteins purified from recombinant ERA RABV expressing glycoprotein (G) from RABV, MOKV and WCBV. Left bars for each clone indicate clones selected using the whole recombinant virus ERA RABV expressing glycoprotein (G) from RABV, MOKV and WCBV. Right bars for each clone indicate clones selected using glycoproteins purified from the recombinant ERA RABV expressing glycoprotein (G) from RABV, MOKV and WCBV. Using a standard ELISA method, raw absorbance (420 nm-650 nm) was fixed relative to a known clone binding to its cognate antigen (positive control).
Figure 4:
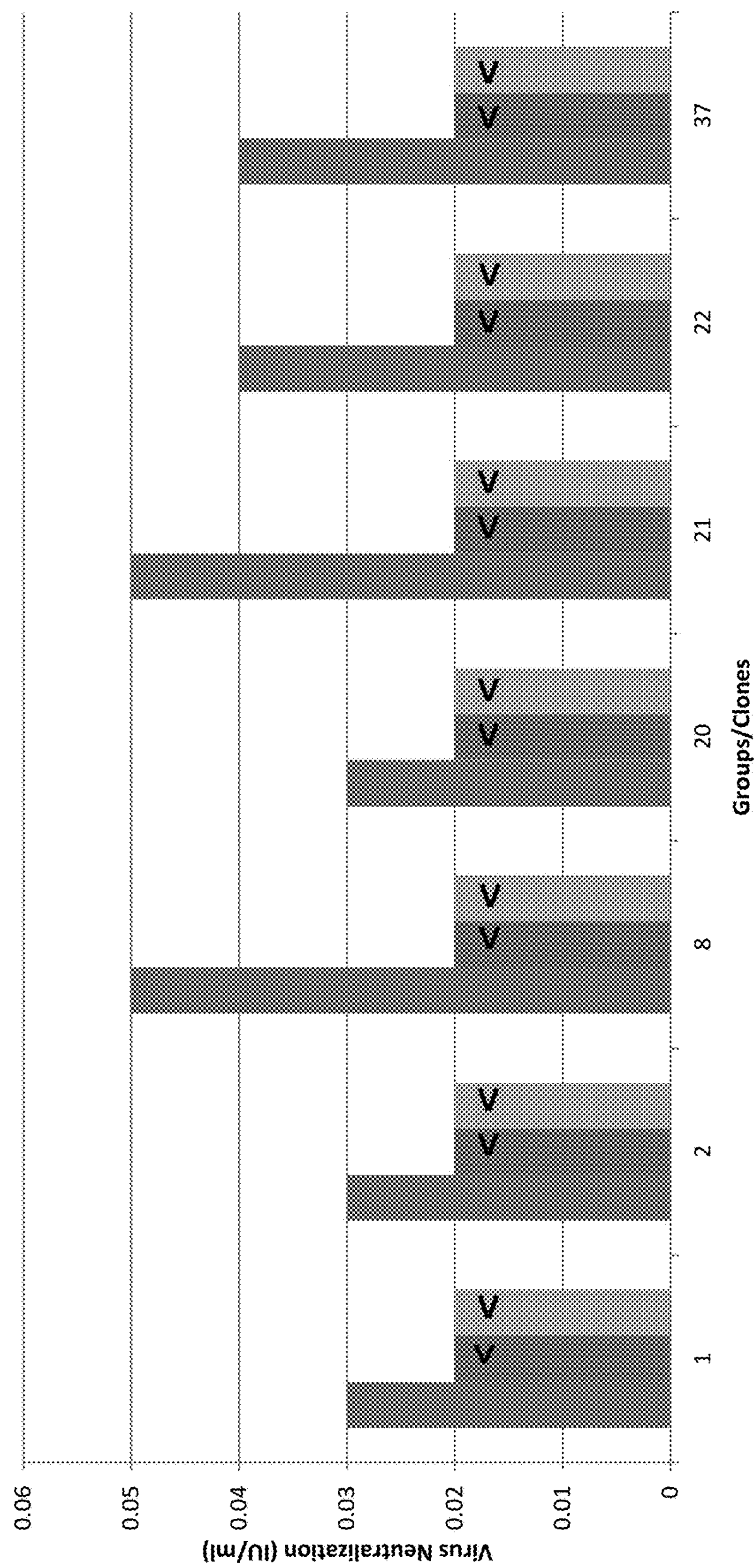
FIG. 4: Results of rapid fluorescent focus inhibition test (RFFIT). Rabies virus ERA3G was incubated with standard dilutions of soluble domain antibodies from selected clones for 20 hours. Virus neutralization was assessed using direct immunofluorescent staining. Results of three biological replicates are shown with titers less than 0.02 IU/ml indicated by the symbol (<).

*Number of clones with mean ELISA binding ≥ positive control from three biological replicates Relative binding (as assessed by ELISA) of each of the clones to whole virus and glycoprotein is shown in FIG. 2 and FIG. 3, respectively. Representative clones from groups 1 and 17 appear to bind to whole virus, whereas clones from groups 1, 9, 23, 30 and 31 appear to bind glycoprotein. A modified rapid fluorescent focus inhibition test (RFFIT) was used to screen dAbs for virus neutralization. The results are shown in FIG. 4. Observed weak neutralization may be due to poor expression of soluble antibodies due to in-frame stop codons.

Sequencing of Clones

Sixty-nine percent of the clones selected for binding to whole virus and 37% of the clones selected for binding to glycoprotein were successfully sequenced. The sequences of each clone are provided in the Sequence Listing as SEQ ID NOs: 1-43 as follows:

| Clone | SEQ ID NO: |
|---|---|
| H01_plate2_group1 | 1 |
| B05_plate4_group2 | 2 |
| B08_plate4_group3 | 3 |
| C10_plate4_group4 | 4 |
| G05_plate2_group5 | 5 |
| G04_plate2_group6 | 6 |
| C02_plate4_group7 | 7 |
| A06_plate4_group8 | 8 |
| H12_plate1_group9 | 9 |
| F09_palte4_group10 | 10 |
| H09_plate4_group11 | 11 |
| G04_plate4_group12 | 12 |
| F05_plate4_group13 | 13 |
| E01_plate2_group14 | 14 |
| E07_plate2_group15 | 15 |
| F03_plate1_group16 | 16 |
| E02_plate2_group17 | 17 |
| A05_plate1_group18 | 18 |
| C08_plate1_group19 | 19 |
| B02_plate1_group20 | 20 |
| G09_plate11_group1 | 21 |
| H07_plate14_group2 | 22 |
| E04_plate11_group7 | 23 |
| H08_plate13_group15 | 24 |
| F12_plate13_group18 | 25 |
| B03_plate14_group19 | 26 |
| H05_plate13_group21 | 27 |
| G06_plate14_group22 | 28 |
| F05_plate11_group23 | 29 |
| D11_plate11_group24 | 30 |
| H01_plate13_group25 | 31 |
| C10_plate11_group26 | 32 |
| D11_plate14_group27 | 33 |
| B08_plate11_group28 | 34 |
| H08_plate14_group29 | 35 |
| H06_plate14_group30 | 36 |
| H07_plate11_group31 | 37 |
| E12_plate14_group32 | 38 |
| A11_plate11_group33 | 39 |
| B04_plate13_group34 | 40 |
| A08_plate11_group35 | 41 |
| B05_plate13_group36 | 42 |
| E04_plate14_group37 | 43 |

Example 3: *Lyssavirus* Domain Antibodies Selected by Sequential Panning of Glycoprotein Expressing Cells This example describes the identification of $V_H$ domain antibodies specific for *lyssavirus* glycoprotein by sequential panning of a naïve, human $V_H$ domain phage display library (Famm et al., *J. Mol. Biol.* 376:926-931, 2008) on cell lines expressing glycoprotein (G) from several different *lyssaviruses.*

Flp-In-BHK cells (Invitrogen) were transfected with a pEF5/FRT/V5 plasmid (Invitrogen) encoding glycoprotein from LBV (SEQ ID NO: 118), MOKV (SEQ ID NO: 115), WCBV (SEQ ID NO: 116), or DUVV (SEQ ID NO: 119). The library was panned sequentially on cells that express LBV G protein, followed by MOKV G protein, followed by WCBV G protein and finally DUVV G protein. Selection on cells was carried out using the method described by Lee et al. (*Nature Protocols* 2(11):3001-3008, 2007).

Using this method, 67 unique nucleotide sequences were identified (Table 2). Each $V_H$ sequence has at least one change in amino acid sequence when translated. In-frame "TAG" (stop codons) will be changed to "GAG" (glutamate codons) to allow expression in eukaryotic cell line. $V_H$ sequences will be cloned into the pEF5/FRT/V5 plasmid to transfect Flp-In-BHK cells for expression of antibodies.

TABLE 2

Unique $V_H$ clones identified by sequential panning of cells

| $V_H$ Clone Name | SEQ ID NO: | CDR1 nucleotide positions[1] | CDR2 nucleotide positions[1] | CDR2 nucleotide positions[1] |
|---|---|---|---|---|
| plate11_G09_group1 | 44 | 76-111 | 148-193 | 295-336 |
| plate14_H07_group2 | 45 | 76-111 | 148-193 | 295-336 |
| plate4_B08_group3 | 46 | 76-111 | 148-193 | 295-330 |
| plate4_C10_group4 | 47 | 76-111 | 148-193 | 295-333 |
| plate2_G05_group5 | 48 | 76-111 | 148-193 | 295-351 |
| plate2_G04_group6 | 49 | 76-111 | 148-193 | 295-339 |
| plate4_C02_group7 | 50 | 76-111 | 148-193 | 295-339 |
| plate4_A06_group8 | 51 | 76-111 | 148-193 | 295-351 |
| plate1_H12_group9 | 52 | 76-111 | 148-193 | 295-339 |
| palte4_F09_group10 | 53 | 76-111 | 148-193 | 295-336 |
| plate4_H09_group11 | 54 | 76-111 | 148-193 | 295-333 |
| plate4_G04_group12 | 55 | 76-111 | 148-193 | 295-342 |
| plate4_F05_group13 | 56 | 76-111 | 148-193 | 295-354 |
| plate2_E01_group14 | 57 | 76-111 | 148-193 | 295-360 |
| plate13_H08_group15 | 58 | 76-111 | 148-193 | 295-348 |
| plate4_B05_group16 | 59 | 76-111 | 148-193 | 295-336 |
| plate2_E02_group17 | 60 | 76-111 | 148-193 | 295-336 |
| plate1_A05_group18 | 61 | 76-111 | 148-193 | 295-336 |
| plate14_B03_group19 | 62 | 76-111 | 148-193 | 295-333 |
| plate1_B02_group20 | 63 | 76-111 | 148-193 | 295-351 |
| plate13_F12_group21 | 64 | 76-111 | 148-193 | 295-336 |
| plate14_G06_group22 | 65 | 76-111 | 148-193 | 295-351 |
| plate11_F05_group23 | 66 | 76-111 | 148-193 | 295-339 |
| plate11_D11_group24 | 67 | 76-111 | 148-193 | 295-330 |
| plate13_H01_group25 | 68 | 76-111 | 148-193 | 295-339 |
| plate11_C10_group26 | 69 | 76-111 | 148-193 | 295-336 |
| plate14_D11_group27 | 70 | 76-111 | 148-193 | 295-330 |
| plate11_B08_group28 | 71 | 76-111 | 148-193 | 295-330 |
| plate14_H08_group29 | 72 | 76-111 | 148-193 | 295-330 |
| plate14_H06_group30 | 73 | 76-111 | 148-193 | 295-345 |
| plate11_H07_group31 | 74 | 76-111 | 148-193 | 295-333 |
| plate14_E12_group32 | 75 | 76-111 | 148-193 | 295-336 |
| plate11_A11_group33 | 76 | 76-111 | 148-193 | 295-333 |
| plate13_B04_group34 | 77 | 76-111 | 148-193 | 295-339 |
| plate11_A08_group35 | 78 | 76-111 | 148-193 | 295-345 |
| plate13_B05_group36 | 79 | 76-111 | 148-193 | 295-333 |
| plate14_E04_group37 | 80 | 76-111 | 148-193 | 295-333 |
| plate5_B02_group38 | 81 | 76-111 | 148-193 | 295-339 |
| plate5_A08_group39 | 82 | 76-111 | 148-193 | 295-330 |
| plate5_G03_group40 | 83 | 76-111 | 148-193 | 295-339 |
| plate5_D02_group41 | 84 | 76-111 | 148-193 | 295-339 |
| plate5_B11_group42 | 85 | 76-111 | 148-193 | 295-339 |
| plate5_A05_group43 | 86 | 76-111 | 148-193 | 295-330 |
| plate5_G09_group44 | 87 | 76-111 | 148-193 | 295-339 |
| plate5_C01_group45 | 88 | 76-111 | 148-193 | 295-339 |
| plate5_D01_group46 | 89 | 76-111 | 148-193 | 295-339 |
| plate5_C10_group47 | 90 | 76-111 | 148-193 | 295-339 |
| plate5_D10_group48 | 91 | 76-111 | 148-193 | 295-339 |
| plate5_D03_group49 | 92 | 76-111 | 148-193 | 295-339 |
| plate5_C03_group50 | 93 | 76-111 | 148-193 | 295-339 |
| plate5_G10_group51 | 94 | 76-111 | 148-193 | 295-339 |
| plate5_H06_group52 | 95 | 76-111 | 148-193 | 295-330 |
| plate5_A06_group53 | 96 | 76-111 | 148-193 | 295-330 |
| plate52_E08_group54 | 97 | 10-45 | 82-127 | 229-264 |
| plate52_C06_group55 | 98 | 44-79 | 115-160 | 262-306 |
| plate52_E01_group56 | 99 | 76-111 | 148-193 | 295-330 |
| plate52_C08_group57 | 100 | 34-69 | 106-151 | 253-288 |
| plate52_B09_group58 | 101 | 12-47 | 84-129 | 231-266 |
| plate53_A03_group59 | 102 | 76-111 | 148-193 | 295-336 |
| plate53_C12_group60 | 103 | 76-111 | 148-193 | 295-330 |
| plate53_B08_group61 | 104 | 76-111 | 148-193 | 295-351 |
| plate54_A03_group62 | 105 | 73-105 | 142-187 | 289-324 |
| plate54_E11_group63 | 106 | 65-97 | 134-179 | 281-316 |
| plate54_D09_group64 | 107 | 65-97 | 134-179 | 281-316 |
| plate54_C01_group65 | 108 | 65-97 | 134-179 | 281-316 |
| plate54_G05_group66 | 109 | 60-92 | 129-174 | 276-311 |
| plate54_C12_group67 | 110 | 77-112 | 149-194 | 296-358 |

[1] Each CDR sequence is identified by the nucleotide positions of the provided SEQ ID NO.

Example 4: Rabies Prophylaxis Using *Lyssavirus* mAbs

A subject diagnosed with rabies or at risk of developing rabies (such as a subject bitten by a potentially rabid animal) is subjected to rabies post-exposure prophylaxis, which includes administration of a rabies vaccine, such as Imovax™ or RabAvert™, according to the recommended dosing schedule. Subjects who have not previously been vaccinated against rabies will further be treated with one or more of the *lyssavirus* mAbs disclosed herein.

*Lyssavirus* mAb is administered intramuscularly to the subject at a site distant to the site of vaccine administration. If the subject diagnosed with rabies, or at risk of developing rabies, has a bite wound, *lyssavirus* mAb can optionally be administered directly into the wound and to the area directly adjacent to the wound.

Doses of *lyssavirus* mAb generally range from 1 to 50 IU/kg. In particular examples, the dose is about 5 or about 20 IU/kg. However, the dose of *lyssavirus* mAb will vary depending upon the antibody (or antibody cocktail) selected and the particular subject to be treated. An appropriate does can be determined by a medical practitioner.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. An isolated monoclonal antibody, or antigen-binding fragment thereof, that specifically binds at least two different *lyssaviruses* or that specifically binds glycoprotein from at least two different *lyssaviruses*, wherein the antibody or antigen-binding fragment thereof comprises a variable heavy ($V_H$) domain complementarity determining region 1 (CDR1), CDR2 and CDR3, and wherein the CDR1, CDR2 and CDR3 are encoded by the CDR1, CDR2 and CDR3 nucleotide sequences of any one of SEQ ID NOs: 45-110.

2. The isolated monoclonal antibody of claim 1, wherein the at least two different *lyssaviruses* are selected from rabies virus (RABV), Mokola virus (MOKV), West Caucasian bat virus (WCBV), Lagos bat virus (LBV) and Duvenhage virus (DUVV).

3. The isolated monoclonal antibody of claim 1, comprising a $V_L$ domain from a rabies virus-specific antibody.

4. The isolated monoclonal antibody of claim 1, wherein the antibody is an IgG.

5. The isolated monoclonal antibody of claim 1, wherein the antibody is a human antibody or a humanized antibody.

6. The isolated monoclonal antibody of claim 1, wherein the antigen-binding fragment is a Fab fragment, a Fab' fragment, a F(ab)'$_2$ fragment, a single chain Fv protein (scFv), or a disulfide stabilized Fv protein (dsFv).

7. The isolated monoclonal antibody of claim 1, wherein the VH domain of the antibody or antigen-binding fragment is encoded by a nucleotide sequence at least 95%, at least 96%, at least 97%, at least 98% or at least 99% identical to any one of SEQ ID NOs: 102-110, and wherein the VH domain CDR1, CDR2 and CDR3 are encoded by the CDR1, CDR2 and CDR3 nucleotide sequences of the corresponding sequence from SEQ ID NOs:102-110.

8. The isolated monoclonal antibody of claim 7, wherein the $V_H$ domain of the antibody or antigen-binding fragment is encoded by a nucleotide sequence comprising any one of SEQ ID NOs: 102-110.

9. An isolated immunoconjugate comprising the monoclonal antibody of claim 1 and a fusion partner.

10. The isolated immunoconjugate of claim 9, wherein the fusion partner is an effector molecule, a label or a heterologous polypeptide.

11. A composition comprising the monoclonal antibody or antigen-binding fragment of claim 1 and a pharmaceutically acceptable carrier.

12. A composition comprising the monoclonal antibody or antigen-binding fragment of claim 1 and a monoclonal antibody specific for RABV or RABV glycoprotein.

13. A method of treating rabies in a subject, comprising administering to the subject the monoclonal antibody or antigen-binding fragment of claim 1, thereby treating rabies in the subject.

* * * * *

SEQUENCE LISTING

```
<160> NUMBER OF SEQ ID NOS: 119

<210> SEQ ID NO 1
<211> LENGTH: 822
<212> TYPE: DNA
<213> ORGANISM: Artificial Sequence
<220> FEATURE:
<223> OTHER INFORMATION: Recombinant polynucleotide

<400> SEQUENCE: 1

taaacaactt tcaacagtct atgtttgccc cctttccaag tcggttcatc tctatgtctg     60

tataatgtgc ggccgaattc agatcctctt ctgagatgag tttttgttct gcggccgcgc    120

tcgagacggt gaccagggtt ccctgacccc aaaacttgaa cttgttcgga aacgacaacc    180

gcctctaact cgcgcaataa tataccgcgg tgtcctcggc acgcaggctg ttcatttgca    240

gatacagcgt gttcttggaa ttgtcacggg agatggtgaa ccggcccttc acggagtctg    300

cgtagtatgt gctaccgcta cgcatcccaa tgcttgatac ccactctaga cccttccctg    360

gagcctggcg gacccaggcc atattctaat ggctaatctt aactccggag gctgcacagg    420

agagacgaag ggaccccca ggctgtacca agcctccccc agactccaac agctgcacct    480

gggccatggc cggctgggcc gcatagaaag gtaccactaa aggaattgcg aataataatt    540

ttttcattat gactgtctcc ttgaaataga atttgcatgc aagcttggcg taatcatggt    600

catagctgtt tcctgtgtga aattgttatc cgctcacaat tccacacaac atacgagccg    660

gaagcataaa gtgtaaagcc tgggggtgcc taatgagtga gctaactcac attaatttgc    720

gtttgcgctc actgcccgct tttccagtcc gggaaacctg tcgtgcccag ctgcattaat    780

gaatcggcca accgcgcggg gagaggcggt ttgcgtattg gg                       822


<210> SEQ ID NO 2
<211> LENGTH: 663
<212> TYPE: DNA
<213> ORGANISM: Artificial Sequence
<220> FEATURE:
<223> OTHER INFORMATION: Recombinant polynucleotide

<400> SEQUENCE: 2

cagtcggttc atctctatgt ctgtttaatg tgcggccgaa ttcagatcct cttctgagat     60

gagtttttgt tctgcggccg cgctcgagac ggtgaccagg gttccctgac cccaaaactg    120

gacggtcgtc ggacgcatat actaccgacc tctcgcgcaa tgatataccg cggtgtcctc    180

ggcacgcagg ctgttcattt gcagatacag cgtgttcttg gaattgtcac gggagatggt    240

gaaccggccc ttcacggagt ctgcgtagta tgtgctaccg tcacggccac gaatgcttga    300
```

```
tacccactct agacccttcc ctggagcctg gcggacccag cccatattct tatgggtaag    360

cctaactccg gaggctgcac aggagagacg cagggacccc ccaggctgta ccaagccttc    420

cccagactcc aacagctgca cctgggccat ggccggctgg gccgcataga aaggtaccac    480

taaaggaatt gcgaataata atttttttcat tatgactgtc tccttgaaat agaatttgca    540

tgcaagcttg gcgtattcat ggtcatagct gtttcctgtg tgaaattgtt atccgctcac    600

aattccacac aacatacgag ccggaagcat aaagtgtaaa gcctgtggtg cctaatgagt    660

gag                                                                  663


<210> SEQ ID NO 3
<211> LENGTH: 649
<212> TYPE: DNA
<213> ORGANISM: Artificial Sequence
<220> FEATURE:
<223> OTHER INFORMATION: Recombinant polynucleotide

<400> SEQUENCE: 3

acagtctatg cggcccccctt tccagtcggt tcatctctat gtctgtataa tgtgcggccg     60

aattcagatc ctcttctgag atgagttttt gttctgcggc cgcgctcgag acggtgacca    120

gggttccctg accccaatag cggaagttgg cggtacgcct cctcctaccc gcgcaataat    180

ataccgcggt gtcctcggca cgcaggctgt tcatttgcag atacagcgtg ttcttggaat    240

tgtcacggga gatggtgaac cggcccttca cggagtctgc gtattatgtg ctaccgcttc    300

gcgtacgaat ggttgatacc cactctagac ccttccctgg agcctggcgg acccaggcca    360

tatcctaata gataatgtta actccggagg ctgcacagga gagacgcagg gacccccccag    420

gctgtaccaa gcctccccca gactccaaca gctgcacctg ggccatggcc ggctgggccg    480

catagaaagg taccactaaa ggaattgcga ataataattt tttcattatg actgtctcct    540

tgaaatagaa tttgcatgca agcttggcgt aatcatggtc atagctgttt cctgtgtgaa    600

attgttatct cgctcacaat tccacacaac atacgagccg gaagcataa               649


<210> SEQ ID NO 4
<211> LENGTH: 780
<212> TYPE: DNA
<213> ORGANISM: Artificial Sequence
<220> FEATURE:
<223> OTHER INFORMATION: Recombinant polynucleotide

<400> SEQUENCE: 4

aaacaacttt caacagtcta tgcggccccc tttccaagtc ggttcatctc tatgtctgta     60

taatgtgcgg ccgaattcag atcctcttct gagatgagtt tttgttctgc ggccgcgctc    120

gagacggtga ccagggttcc ctgaccccaa tacttcatgt tcgccggccg cctaaccctc    180

gttgtcgcgc aataatatac cgcggtgtcc tcggcacgca ggctgttcat ttgcagatac    240

agcgtgttct tggaattgtc acgggagatg gtgaaccggc ccttcacgga gtctgcgtag    300

tatgtgctac cgttttgcat cagaatgctt gatacccact ctagaccctt ccctggagcc    360

tggcggaccc aggccataga ctaatagcta atcttaactc cggaggctgc acaggagaga    420

cgcagggacc ccccaggctg taccaagcct cccccagact ccaacagctg cacctgggcc    480

atggccggct gggccgcata gaaaggtacc actaaaggaa ttgcgaataa taattttttc    540

attatgactg tctccttgaa atagaatttg catgcaagct tggcgtaaat catggtcata    600

gctgtttcct gtgtgaaaat tgttatccgc tcacaattcc acacaacata cgagcccgga    660
```

```
agcataaagt gtaaagcctg gggtgcctaa tgagtgagct aaccccacat ttaattgctt    720

tgcgctcact gccccctttc cattcgggaa acctgtcgtg ccagctgcat taatgaaatc    780


<210> SEQ ID NO 5
<211> LENGTH: 799
<212> TYPE: DNA
<213> ORGANISM: Artificial Sequence
<220> FEATURE:
<223> OTHER INFORMATION: Recombinant polynucleotide

<400> SEQUENCE: 5

taaacaactt tcaacagtct atgcggcccc ctttccaagt cggttcatct ctatgtctgt     60

ataatgtgcg gccgaattca gatcctcttc tgagatgagt ttttgttctg cggccgcgct    120

cgagacggtg accagggttc cctgacccca atacctgatc ggcttcgcag tcagaccagc    180

ccaccacata ctcctaggaa ctgtcgcgca ataatatacc gcggtgtcct cggcacgcag    240

gctgttcatt tgcagataca gcgtgttctt ggaattgtca cgggagatgg tgaaccggcc    300

cttcacggag tctgcgtagt atgtgctacc gcctcgcata ttaatgcttg atacccactc    360

tagacccttc cctggagcct ggcggaccca gcccatagcc taagagttaa acctatatcc    420

ggaggctgca caggagagac gcagggaccc cccaggctgt accaagcctc ccccagactc    480

caacagctgc acctgggcca tggccggctg ggccgcatag aaaggtacca ctaaaggaat    540

tgcgaataat aatttttttca ttatgactgt ctccttgaaa tagaatttgc atgcaagctt    600

ggcgtaatca tggtcatagc tgtttcctgt gtgaaattgt tatccgctca caattcccca    660

caacatacga gcccggaagc ataaagtgta aagccctggg gtgcctaatg agtgagctaa    720

ctcacattta attgcgttgc gctcactgcc cgcttttcca gtcgggaaac cctgtcgtgc    780

cagcttgcat taatgaatc                                                 799


<210> SEQ ID NO 6
<211> LENGTH: 838
<212> TYPE: DNA
<213> ORGANISM: Artificial Sequence
<220> FEATURE:
<223> OTHER INFORMATION: Recombinant polynucleotide

<400> SEQUENCE: 6

tgaatttttt ctgttatgag gtttccgcta aacaactttc aacagtctat gcggccccct     60

ttccaagtcg gttcatctct atgtctgtat aatgtgcggc cgaattcaga tcctcttctg    120

agatgagttt ttgttctgcg gccgcgctcg agacggtgac cagggttccc tgaccccaat    180

accggagcgg cgacacaagc caccgcttac cacgcctacc cgcgcaataa tataccgcgg    240

tgtcctcggc acgcaggctg ttcatttgca gatacagcgt gttcttggaa ttgtcacggg    300

agatggtgaa ccggcccttc acggagtctg cgtagtatgt gctaccgctt tgcgtcataa    360

tgcttgatac ccactctaga cccttccctg gagcctggcg gacccagccc atatactaat    420

tggtaaactt aactccggag gctgcacagg agagacgcag ggaccccccca ggctgtacca    480

agcctccccc agactccaac agctgcacct gggccatggc cggctgggcc gcatagaaag    540

gtaccactaa aggaattgcg aataataatt ttttcattat gactgtctcc ttgaaataga    600

atttgcatgc cagcttggcg taatcatggt catagctgtt ccctgtgtga aatttgttat    660

ccgctcacaa ttccacacaa catacgagcc ggaagcataa aagtgtaaag cctggggtgc    720

ctaatgagtg agctaactca cattaattgc gttgcgctca ctgcccgctt tccagtcggg    780

aaacctgtcg cgccagcctg catttaatga atcggccaac gcgcggggag aggcggtt     838
```

<210> SEQ ID NO 7
<211> LENGTH: 673
<212> TYPE: DNA
<213> ORGANISM: Artificial Sequence
<220> FEATURE:
<223> OTHER INFORMATION: Recombinant polynucleotide

<400> SEQUENCE: 7

```
agtcggttca tctctatgtc tgtataatgt gcggccgaat tcagatcctc ttctgagatg     60

agtttttgtt ctgcggccgc gctcgagacg gtgaccaggg ttccctgacc ccaaaacttg    120

atgtacttcg tacgaaaagg cgcccgacgc gcactcgcgc aataatatac cgcggtgtcc    180

tcggcacgca ggctgttcat ttgcagatac agcgtgttct tggaattgtc acgggagatg    240

gtgaaccggc ccttcacgga gtctgcgtag tatgtgctac cgcttcggct attaatgcct    300

gatacccact ctagaccctt ccctggagcc tggcggaccc agctcataaa ctaatggtta    360

aacctaactc cggaggctgc acaggagaga cgcagggacc ccccaggctg taccaagcct    420

cccccagact ccaacagctg cacctgggcc atggccggct gggccgcata gaaaggtacc    480

actaaaggaa ttgcgaataa taatttttttc attatgactg tctccttgaa atagaatttg    540

catgcaagct tggcgtaatc atggtcatag ctgtttcctg tgtgaaattg ttatccgctc    600

acaattccac acaacatacg agccggaagc ataaagtgta aagcctgggg tgcctaatga    660

gtgagctaac ttc                                                        673
```

<210> SEQ ID NO 8
<211> LENGTH: 649
<212> TYPE: DNA
<213> ORGANISM: Artificial Sequence
<220> FEATURE:
<223> OTHER INFORMATION: Recombinant polynucleotide

<400> SEQUENCE: 8

```
gccgaattca gatcctcttc tgagatgagt ttttgttctg cggccgcgct cgagacggtg     60

accagggttc cctgacccca aaaccccatc ttgtggggca cagaccaagg cctacccctc    120

aaacgccgag gtgccgcgca ataatatacc gcggtgtcct cggcacgcag gctgttcatt    180

tgcagataca gcgtgttctt ggaattgtca cgggagatgg tgaaccggcc cttcacggag    240

tctgcgtagt atgtgctacc gtctgtggta ttaatgcctg atacccactc tagacccttc    300

cctggagcct ggcggaccca gctcatagcc taattgctaa acctatctcc ggaggctgca    360

caggagagac gcagggaccc cccaggctgt accaagcctc ccccagactc caacagctgc    420

acctgggcca tggccggctg ggccgcatag aaaggtacta ctaaaggaat tgcgaataat    480

aatttttttca ttatgactgt ctccttgaaa tagaatttgc atgcaagctt ggcgtaatta    540

tggtcatagc tgttttccct gtgtgaaatt gttatccgct cacaattcca cacaacatac    600

gagctcggaa gcataaagtg tataagcctg ggtgcctaat gagtgagct                 649
```

<210> SEQ ID NO 9
<211> LENGTH: 866
<212> TYPE: DNA
<213> ORGANISM: Artificial Sequence
<220> FEATURE:
<223> OTHER INFORMATION: Recombinant polynucleotide

<400> SEQUENCE: 9

```
aaatgaattt tctgtatgag gttttgctaa acaactttca acagtctatg cggcccctt      60
```

```
tccagtcggt tcatctctat gtctgtataa tgtgcggccg aattcagatc ctcttctgag    120

atgagttttt gttctgcggc cgcgctcgag acggtgacca gggttccctg accccaagac    180

gtcaagggct tcggccactt cctcccccca tgccatctcg cgcaataata taccgcggtg    240

tcctcggcac gcaggctgtt catttgcaga tacagcgtgt tcttggaatt gtcacgggag    300

atggtgaacc ggcccttcac ggagtctgcg tagtatgtgc taccgttagt catagcaatg    360

gttgataccc actctagacc cttccctgga gcctggcgga cccagcccat atactaatgg    420

ctaaacctaa atccggaggc tgcacaggag agacgcaggg accccccagg ctgtaccaag    480

cctcccccag actccaacag ctgcacctgg gccatggccg gctgggccgc atagaaaggt    540

accactaaag gaattgcgaa taataatttt ttcattatga ctgtctcctt gaaatagaat    600

ttgcatgcaa gcttggcgta aatcatggtc atagctgttt cctgtgtgaa attgttatcc    660

gctcacaatt ccacacaaca tacgagccgg aagcataaag tgtaaagcct ggggtgccta    720

atgagtgagc taactcacat taattgcgtt gcgctcactg cccgctttcc gtcgggaaac    780

ctgtcgtgcc agctgcatta atgaatcggc ccaacgcgcg gggagaggcg ggtttgcgta    840

ttgggcgctc ttccgctttc ctcgct                                         866
```

<210> SEQ ID NO 10
<211> LENGTH: 878
<212> TYPE: DNA
<213> ORGANISM: Artificial Sequence
<220> FEATURE:
<223> OTHER INFORMATION: Recombinant polynucleotide

<400> SEQUENCE: 10

```
gaattttctg tatgaggttt tgctaaacaa ctttcaacag tctatgcggc cccctttcca     60

gtcggttcat ctctatgtct gtataatgtg cggccgaatt cagatcctct tctgagatga    120

gtttttgttc tgcggccgcg ctcgagacgg tgaccagggt tccctgaccc caaaaccgca    180

tgtagtgcga agcaccaagc ctacgccgtc tcgcgcaata atataccgcg gtgtcctcgg    240

cacgcaggct gttcatttgc agatacagcg tgttcttgga attgtcacgg gagatggtga    300

accggccctt cacggagtct gcgtagtatg tgctaccgtt agtggcacca atggttgata    360

cccactctag acccttccct ggagcctggc ggacccaggc catagtctaa tcgttaaacc    420

tatatccgga ggctgcacag gagagacgca gggacccccc aggctgtacc aagcctcccc    480

cagactccaa cagctgcacc tgggccatgg ccggctgggc cgcatagaaa ggtaccacta    540

aaggaatttg cgaataataa tttttcatt atgactgtct ccttgaaata gaatttgcat    600

gcaagcttgg cgtaatcatg gtcatagctg tttcctgtgt gaaattgtta tccgctcaca    660

attccacaca acatacgagc cggaagcata aagtgtaaag cctggggtgc ctaatgagtg    720

agctaactca cattaattgc gttgcgctca ctgcccgctt tccagtcggg aaacctgtcg    780

tgccagctgc attaatgaat cggccaacgc gcggggagag gcggtttgcg tattgggcgc    840

tcttccgctt cctcgctcac tgactcgctg cgctccgg                            878
```

<210> SEQ ID NO 11
<211> LENGTH: 905
<212> TYPE: DNA
<213> ORGANISM: Artificial Sequence
<220> FEATURE:
<223> OTHER INFORMATION: Recombinant polynucleotide

<400> SEQUENCE: 11

```
gttagtaaat gaattttctg tatgaggttt tgctaaacaa ctttcacagt ctatgcggcc     60
```

```
ccctttccaa gtcggttcat ctctatgtct gtataatgtg cggccgaatt cagatcctct    120

tctgagatga gtttttgttc tgcggccgcg ctcgagacgg tgaccagggt tccctgaccc    180

caagagtaga agttggtcgg ccgctgcctc gcctatctcg cgcaataata taccgcggtg    240

tcctcggcac gcaggctgtt catttgcaga tacagcgtgt tcttggaatt gtcacgggag    300

atggtgaacc ggcccttcac ggagtctgcg tagtatgtgc taccgtcacg gttcctaatg    360

gttgataccc actctagacc cttccctgga gcctggcgga cccagctcat atagtgagag    420

ttaaacttat atccggaggc tgcacaggag agacgcaggg acccccccagg ctgtaccaag   480

cctcccccag actccaacag ctgcacctgg gccatggccg gctgggccgc ctagaaaggt    540

accactaaag gaattgcgaa taataatttt tttcattatg actgtctcct tgaaatagaa    600

tttgcatgca agcttggcgt aatcatggtc atagctgttt cctgtgtgaa attgttatcc    660

gctcacaatt tccacacaac atacgagccg gaaagcataa agtgtaaagc ctggggtgc     720

ctaatgagtg agctaactca cattaattgc gttgcgctca ctgcccgctt ttccagtcgg    780

ggaaacctgt cgtgccagct gcattaatga atcggcccaa cgcgcgggga gaggcggttt    840

tgcgtattgg gcgctcttcc gcttccctcg cctcactgac ttcgctgcgc tcgggtcgtt    900

cggct                                                                905
```

<210> SEQ ID NO 12
<211> LENGTH: 673
<212> TYPE: DNA
<213> ORGANISM: Artificial Sequence
<220> FEATURE:
<223> OTHER INFORMATION: Recombinant polynucleotide

<400> SEQUENCE: 12

```
aaatgaattt tctgtatgag gtttccgcta aacaactttc aacagtctat gcggccccct     60

ttccaagtcg gttcatctct atgtctgtat aatgtgcggc cgaattcaga tcctcttctg    120

agatgagttt ttgttctgcg gccgcgctcg agacggtgac cagggttccc tgaccccaag    180

actcgaccta gttgggagtc gccaacctcc acctattaac tctcgcgcaa taatataccg    240

cggtgtcctc ggcacgcagg ctgttcattt gcagatacag cgtgttcttg gaattgtcac    300

gggagatggt gaaccggccc ttcacggagt ctgcgtagta tgtgctaccg tcacgggtct    360

taatggttga tacccactct agacccttcc ctggagcctg gcggacccag cccatatact    420

tagggataac cctaaatcct gaggctgcac aggagagacg cagggacccc ccaggctgta    480

ccaagcctcc cccagactcc aacagctgca cctgggccat ggccggctgg gccgcataga    540

aaggtaccac taaaggaatt gcgaataata atttttttca ttatgactgt ctccttgaaa    600

tagaattttg catgcaagct tggcgtaatc atggtcatag ctgtttcctg tgtgaaattg    660

ttatcccgct cac                                                       673
```

<210> SEQ ID NO 13
<211> LENGTH: 957
<212> TYPE: DNA
<213> ORGANISM: Artificial Sequence
<220> FEATURE:
<223> OTHER INFORMATION: Recombinant polynucleotide

<400> SEQUENCE: 13

```
agttagtaaa tgaattttct gtatgaggtt ttgctaaaca actttcaaca gtctatgcgg     60

ccccctttca agtcggttca tctctatgtc tgtataatgt gcggccgaat tcagatcctc    120
```

-continued

```
ttctgagatg agtttttgtt ctgcggccgc gctcgagacg gtgaccaggg ttccctgacc    180

ccaaaagcgc atgtgcggct tcctcatcat acccggaaac ctccccatcc ccttctttct    240

cgcgcaataa tataccgcgg tgtcctcggc acgcaggctg ttcatttgca gatacagcgt    300

gttcttggaa ttgtcacggg agatggtgaa ccggcccttc acggagtctg cgtagtatgt    360

gctaccgctt ggggcacgaa tggctgatac ccactctaga cccttccctg gagcctggcg    420

gacccagctc atatcctaat tgttaagcat aaatccggag gctgcacagg agagacgcag    480

ggaccccca ggctgtacca agcctccccc agactccaac agctgcacct gggccatggc    540

cggctgggcc gcatagaaag gtaccactaa aggaattgcg aataataatt ttttcattat    600

gactgtctcc ttgaaataga atttgcatgc aagcttggcg taatcatggt catagctgtt    660

tcctgtgtga aattgttatc cgctcacaat tccacacaac atacgagccg gaagcataaa    720

gtgtaaagcc tggggtgcct aatgagtgag ctaactcaca ttaattgcgt tgcgctcact    780

gcccgctttc cagtcgggaa acctgtcgtg ccagctgcat taatgaatcg gccaacgcgc    840

ggggagaggc ggtttgcgta ttgggcgctc ttccgcttcc tcgctcactg actccgctgc    900

gctcggtcgt tcggctgcgg cgagcggtat cagctcactc aaaggcggta atacggt       957
```

```
<210> SEQ ID NO 14
<211> LENGTH: 374
<212> TYPE: DNA
<213> ORGANISM: Artificial Sequence
<220> FEATURE:
<223> OTHER INFORMATION: Recombinant polynucleotide

<400> SEQUENCE: 14

aacagtctat gcggccccct ttccaagccc ggttcatctc tatgtctgta taatgtgcgg     60

ccgaattcag atcctcttct gagatgagtt tttgttctgc ggccgcgctc gagacggtga    120

ccagggttcc ctgaccccaa tacctcatcg acttgtgctg ctaatccccc ccccgatacc    180

gacaacgcct cctcccacaa ctcgcgcaat aatataccgc ggtgtcctcg gcccgcaggc    240

tgttcatttg cagatacagc gtgttcttgg aattgtcacg ggagatggtg aaccggccct    300

tcacggagtc tgcgtagtat gtgctaccgt tacggttccg aatgcttgat acccactcta    360

gacccttccc tgga                                                       374
```

```
<210> SEQ ID NO 15
<211> LENGTH: 731
<212> TYPE: DNA
<213> ORGANISM: Artificial Sequence
<220> FEATURE:
<223> OTHER INFORMATION: Recombinant polynucleotide

<400> SEQUENCE: 15

cggttcatct ctatgtctgt ataatgtgcg gccgaattca gatcctcttc tgagatgagt     60

ttttgttctg cggccgcgct cgagacggtg accagggttc cctgacccca aaaccgcaag    120

ttctcggccc gcaccacatt accccgccac gccatcggtc tcgcgcaata atataccgcg    180

gtgtcctcgg cacgcaggct gttcatttgc agatacagcg tgtgcttgga attgtcacgg    240

gagatggtga accggccctt cacggagtct gcgtagtatg tgctaccgtt attcatctta    300

atggttgata cccactctag acccttccct ggagcctggc ggacccagct catatactaa    360

gcgctaaact taaatccgga ggctgcacag gagagacgca gggaccccc aggctgtacc    420

aagcctcccc cagactccaa cagctgcacc tgggccatgg ccggctgggc cgcatagaaa    480

ggtaccacta aaggaattgc gaataataat tttttcatta tgactgtctc cttgaaatag    540
```

aattttgcat gcaagcttgg cgtaatcatg gtcatagctg ttttcctgtg tgaaattgtt 600
atccgctcac aattccacac aacatacgag ccggaagcat aaagtgtaaa gccctggggt 660
gcctaaatga gtgagctaac tcacattaat tgcgttgcgc tcactgcccg ctttccagtc 720
gggaaacctg t 731

<210> SEQ ID NO 16
<211> LENGTH: 439
<212> TYPE: DNA
<213> ORGANISM: Artificial Sequence
<220> FEATURE:
<223> OTHER INFORMATION: Recombinant polynucleotide

<400> SEQUENCE: 16
gttagtaaat gaattttctg tatgaggttt tgctaaacaa ctttcacagt ctatgcggcc 60
ccctttccag tcggttcatc tctatgtctg tataatgtgc ggccgaattc agatcctctt 120
ctgagatgag tttttgttct gcggccgcgc tcgagacggt gaccagggtt ccctgacccc 180
aaaacttgaa cttgtccggc aacgacaacc gcctctaact cgcgcaataa tataccgcgg 240
cgtcctcggc acgcatgctg ttcatataca gatacatcgt gttcttggaa ttgtcacggg 300
agatggggaa ccggcccttc acggagtctg cgtagtatgt gctaccgcta cgcatcccaa 360
tgcttgatac ccaatctaga cccttccctg gagcctggcg gacccaggcc atattctaat 420
ggctaatctt aactgctga 439

<210> SEQ ID NO 17
<211> LENGTH: 716
<212> TYPE: DNA
<213> ORGANISM: Artificial Sequence
<220> FEATURE:
<223> OTHER INFORMATION: Recombinant polynucleotide

<400> SEQUENCE: 17
acagtctatg cggccccctt tccaagtcgg ttcatctcta tgtctgtata atgtgcggcc 60
gaattcagat cctcttctga gatgagtttt tgttctgcgg ccgcgctcga gacggtgacc 120
agggttccct gaccccaaaa ctggaccgtg gtcggacaca aataccaccg acctctcgcg 180
caatgatata ccgcggtgtc ctcggcacgc aggctgttca tttgcagata cagcgtgttc 240
ttggaattgt cacgggagat ggtgaaccgg cccttcacgg agtctgcgta gtatgtgcta 300
ccgctacgga taccaatgct tgatacccac tctagaccct tccctggagc ctggcggacc 360
cagcccatat tctaatggct aagcttaact ccggaggctg cacaggagag acgcagggac 420
cccccaggct gtaccaagcc tcccccagac tccaacagct gcacctgggc catggccggc 480
tgggccgcat agaaaggtac cactaaagga attgcgaata ataatttttt cattatgact 540
gtctccttga aatagaattt gcatgcaagc ttggcgtaat catggtcata gctgtttcct 600
gtgtgaaatt gttatccgct cacaattcca cacaaacata cgagccggaa gcataaagtg 660
taaagccctg gggtgcctaa tgagtgagct aactcacatt aattgcgttg cgctca 716

<210> SEQ ID NO 18
<211> LENGTH: 802
<212> TYPE: DNA
<213> ORGANISM: Artificial Sequence
<220> FEATURE:
<223> OTHER INFORMATION: Recombinant polynucleotide

<400> SEQUENCE: 18

```
tctgtatgag gttttgctaa acaactttca acagtctatg cggcccccctt tccaagtcgg     60

ttcatctcta tgtctgtata atgtgcggcc gaattcagat cctcttctga gatgagtttt    120

tgttctgcgg ccgcgctcga gacggtgacc agggttccct gaccccaaaa cttgaacttg    180

ttcggaaacg acaaccgcct ctaactcgcg caataatata ccgcggtgtc ctcggcacgc    240

aggctgttca tttgcagata cagcgtgttc ttggaattgt cacgggagat ggtgaaccgg    300

cccttcacgg agtctgcgta gtatgtgcta ccgctacgca tcccaatgct tgatacccac    360

tctagaccct tccctggagc ctggcggacc caggccatat tctaacggct aatcttaact    420

ccggaggctg cacaggagag acgaagggac cccccaggct gtaccaagcc tcccccagac    480

tccaacagct gcacctgggc catggccggc tgggccgcat agaaaggtac cactaaagga    540

attgcgaata ataatttttt cattatgact gtctccttga aatagaattt gcatgcaagc    600

ttggcgtaat catggtcata gctgtttcct gtgtgaaatt gttatccgct cacaattcca    660

cacaacatac gagcccggaa gcataaagcg taaagccctg gggtgccct aaatgagcga    720

gctaactcac attaatcgcg ttggcgctca ctgcccgctt tccagtcggc aaaacctgcg    780

tgccagctgc attaatgaat cg                                              802
```

```
<210> SEQ ID NO 19
<211> LENGTH: 643
<212> TYPE: DNA
<213> ORGANISM: Artificial Sequence
<220> FEATURE:
<223> OTHER INFORMATION: Recombinant polynucleotide

<400> SEQUENCE: 19

aacaaccttt caacagtcta tgcggccccc tttccaagtc ggttcatctc tatgtctgta     60

taatgtgcgg ccgaattcag atcctcttct gagatgagtt tttgttctgc ggccgcgctc    120

gagacggtga ccagggttcc ctgaccccaa gacttgaagg cgtggtgcct accccaacgc    180

cgatcaacac cactcgcgca ataatatacc gcggtgtcct cggcacgcag gctgttcatt    240

tgcagataca gcgtgttctt ggaattgtca cgggagatgg tgaaccggcc cttcacggag    300

tctgcgtagt atgtgctacc gttacgcgtc gcaatgcttg atacccactc tagacccttc    360

cctggagcct ggcggaccca gctcatagtc ttagggttaa gcctaactca ggaggctgca    420

caggaaagac gcagggaccc cccaggctgt accaagcctc ccccagactc caacagctgc    480

acctgggcca tggccggctg ggccgcatag aaaggcacaa ctaaaggaat tgcgaataat    540

aatttttttca ttatgactgt ctccttgaaa tagaatttgc atgccagctt ggcgtaacca    600

tggtcatagc tgttttcctg tgtgaaattg ttatccgctc aca                      643
```

```
<210> SEQ ID NO 20
<211> LENGTH: 841
<212> TYPE: DNA
<213> ORGANISM: Artificial Sequence
<220> FEATURE:
<223> OTHER INFORMATION: Recombinant polynucleotide

<400> SEQUENCE: 20

gttagtaaat gaattttctg tatgaggttt cgctaaacaa ctttcacagt ctatgcggcc     60

ccctttccaa gtcggttcat ctctatgtct gtataatgtg cggccgaatt cagatcctct    120

tctgagatga gtttttgttc tgcggccgcg ctcgagacgg tgaccagggt tccctgaccc    180

caagaccaca aggaggacgt ctgaccctcc tcactattcc gccgcccctt ccgtctcgcg    240

caataatata ccgcggtgtc ctcggcacgc aggctgttca tttgcagata cagcgtgttc    300
```

```
ttggaattgt cacgggagat ggtgaaccgg cccttcacgg agtctgcgta gtatgtgcta    360
ccgtcacgct tacgaatggt tgatacccac tctagaccct tccctggagc ctggcggacc    420
cagcccatat actaatagtt aaagctatat ccggaggctg cacaggagag acgcagggac    480
cccccaggct gtaccaagcc tcccccagac tccaacagct gcacctgggc catggccggc    540
tgggccgcat agaaaggtac cactaaagga attgcgaata ataatttttt cattatgact    600
gtctccttga aatagaattt gcatgcaagc ttggcgtaat catggtcata gctgtttcct    660
gtgtgaaatt gttatccgct cacaattcca cacaacatac gagccggaag cataaagtgt    720
aaagcctggg gtgcctactg agtgagctaa ctcacattaa ttgcgttgcg ctcactgccc    780
gctttccagt cgggaaacct gtcgtgccag ctgcattaat gaatcggcca acgcgcgggg    840
a                                                                     841
```

<210> SEQ ID NO 21
<211> LENGTH: 608
<212> TYPE: DNA
<213> ORGANISM: Artificial Sequence
<220> FEATURE:
<223> OTHER INFORMATION: Recombinant polynucleotide

<400> SEQUENCE: 21

```
aacaactttc aacagtctat gcggccccct ttcaagtcgg ttcatctcta tgtctgtata     60
atgtgcggcc gaattcagat cctcttctga gatgagtttt tgttctgcgg ccgcgctcga    120
gacggtgacc agggttccct gaccccaaaa cttgaacttg ttcggaaacg acaaccgcct    180
ctaactcgcg caataatata ccgcggtgtc ctcggcacgc aggctgttca tttgcagata    240
cagcgtgttc ttggaattgt cacgggagat ggtgaaccgg cccttcacgg agtctgcgta    300
gtatgtgcta ccgctacgca tcccaatgct tgatacccac tctagaccct tccctggagc    360
ctggcggacc caggccatat tctaatggct aatcttaact ccggaggctg cacaggagag    420
acgaagggac cccccaggct gtaccaagcc tcccccagac tccaacagct gcacctgggc    480
catggccggc tgggccgcat agaaaggtac cactaaagga attgcgaata ataatttttt    540
cattatgact gtctccttga aatagaattt gcatgcaagc ttggccgtaa tcatggtcat    600
agctgttt                                                             608
```

<210> SEQ ID NO 22
<211> LENGTH: 747
<212> TYPE: DNA
<213> ORGANISM: Artificial Sequence
<220> FEATURE:
<223> OTHER INFORMATION: Recombinant polynucleotide

<400> SEQUENCE: 22

```
tagtaaatga attttctgta tgaggttttg ctaaacaact ttcaacagtc tatgcggccc     60
cctttccagt cggttcatct ctatgtctgt ataatgtgcg gccgaattca gatcctcttc    120
tgagatgagt ttttgttctg cggccgcgct cgagacggtg accagggttc cctgacccca    180
aaactggacg gtcgtcggac gcatatacta ccgacctctc gcgcaatgat ataccgcggt    240
gtcctcggca cgcaggctgt tcatttgcag atacagcgtg ttcttggaat tgtcacggga    300
gatggtgaac cggcccttca cggagtctgc gtagtatgtg ctaccgtcac ggccacgaat    360
gcttgatacc cactctagac ccttccctgg agcctggcgg acccagccca tattcttatg    420
ggtaagccta actccggagg ctgcacagga gagacgcagg gaccccccag gctgtaccaa    480
```

```
gcctccccca gactccaaca gctgcacctg ggccatggcc ggctggtccg catagaaagg    540

taccactaaa ggaattgcga ataataattt tttcattatg actgtctcct tgaaatagaa    600

tttgcatgcc ggcttggcgt aatcatggtc atagctgttt cctgtgtgaa attgttatcc    660

gctcacaatt ccacacaaca tactagccgg aagcataaag tgtaaagcct ggggtgccta    720

atgagtgagc taactcacat taattgc                                        747
```

<210> SEQ ID NO 23
<211> LENGTH: 696
<212> TYPE: DNA
<213> ORGANISM: Artificial Sequence
<220> FEATURE:
<223> OTHER INFORMATION: Recombinant polynucleotide

<400> SEQUENCE: 23

```
aacagtctat gcggccccct ttccagtcgg ttcatctcta tgtctgtata atgtgcggcc     60

gaattcagat cctcttctga gatgagtttt tgttctgcgg ccgcgctcga gacggtgacc    120

agggttccct gaccccaaaa cttgatgtac ttcgtacgaa aaggccccg acgcccactc    180

gcgcaataat ataccgcggt gtcctcggca cgcaggctgt tcatttgcag atacagcgtg    240

ttcttggaat tgtcacggga gatggtgaac cggcccttca cggagtctgc gtagtatgtg    300

ctaccgcttc ggctattaat gcctgatacc cactctagac ccttccctgg agcctggcgg    360

acccagctca taaactaatg gttaaaccta actccggagg ctgcacagga gagacgcagg    420

gaccccccag gctgtaccaa gcctccccca gactccaaca gctgcacctg ggccatggcc    480

ggctgggccg catagaaagg taccactaaa ggaattgcga ataataattt tttcattatg    540

actgtctcct tgaaatagaa tttgcatgca agcttggccg taatcatggt catagctgtt    600

tcctgtgtga aattgttatc ccgctcacaa ttccacacaa catacgagcc gggaagcata    660

aagtgtaaag cctgggggtg cctaatgagt gagcta                              696
```

<210> SEQ ID NO 24
<211> LENGTH: 920
<212> TYPE: DNA
<213> ORGANISM: Artificial Sequence
<220> FEATURE:
<223> OTHER INFORMATION: Recombinant polynucleotide

<400> SEQUENCE: 24

```
ttagtaaatg aattttctgt atgaggtttt gctaaacaac tttcaacagt ctatgcggcc     60

ccctttccag tcggttcatc tctatgtctg tataatgtgc ggccgaattc agatcctctt    120

ctgagatgag tttttgttct gcggccgcgc tcgagacggt gaccagggtt ccctgacccc    180

aaaaccgcaa gttctcggcc cgcaccacat taccccgcca cgccatcggt ctcgcgcaat    240

aatataccgc ggtgtcctcg gcacgcaggc tgttcatttg cagatacagc gtgtgcttgg    300

aattgtcacg ggagatggtg aaccggccct tcacggagtc tgcgtagtat gtgctaccgt    360

tattcatctt aatggttgat acccactcta gacccttccc tggagcctgg cggacccagc    420

tcatatacta agcgctaaac ttaaatccgg aggctgcaca ggagagacgc agggaccccc    480

caggctgtac caagcctccc ccagactcca acagctgcac ctgggccatg gccggctggg    540

ccgcatagaa aggtaccact aaaggaattg cgaataataa tttttttcatt atgactgtct    600

ccttgaaata gaatttgcat gcaagcttgg cgtaatcatg gtcatagctg tttcctgtgt    660

gaaattgtta tccgctcaca attccacaca acatacgagc cggaagcata aagtgtaaag    720

cctggggtgc ctaatgagtg agctaactca cattaattgc gttgcgctca cgcccgcttt    780
```

```
ccagtcggga aacctgtcgt gccagctgca ttaatgaatc ggccaacgcg cggggagagg    840

cggtttgcgt attgggcgct cttccgcttc ctcgctcact gactcgctgc gctcggtcgt    900

tcggctgctg cgagcggtat                                                920
```

<210> SEQ ID NO 25
<211> LENGTH: 884
<212> TYPE: DNA
<213> ORGANISM: Artificial Sequence
<220> FEATURE:
<223> OTHER INFORMATION: Recombinant polynucleotide

<400> SEQUENCE: 25

```
ttagtaaatg aattttctgt atgaggtttt gctaaacaac tttcaacagt ctatgcggcc     60

ccctttcaag tcggttcatc tctatgtctg tataatgtgc ggccgaattc agatcctctt    120

ctgagatgag tttttgttct gcggccgcgc tcgagacggt gaccagggtt ccctgacccc    180

aaaacttgaa cttgttcgga aactacaacc gcctctaact cgcgcaataa tataccgcgg    240

tgtcctcggc acgcaggctg ttcatttgca gatacagcgt gttcttggaa ttgtcacggg    300

agatggtgaa ccggcccttc acggagtctg cgtagtatgt gctaccgcta cgcatcccaa    360

tgcttgatac ccactctaga cccttccctg gagcctggcg gacccaggcc atattctaat    420

ggctaatctt aactccggag gctgcacagg agagacgaag ggaccccca ggctgtacca     480

agcctccccc agactccaac agctgcacct gggccatggc cggctgggcc gcatagaaag    540

gtaccactaa aggaattgcg aataataatt ttttcattat gactgtctcc ttgaaataga    600

atttgcatgc aagcttggcg taatcatggt catagctgtt tcctgtgtga aattgttatc    660

cgctcacaat tccacacaac atacgagccg gaagcataaa gtgtaaagcc tggggtgcct    720

aatgagtgag ctaactcaca ttaattgcgt tgcgctcact gcccgctttc cagtcgggaa    780

acctgtcgtg ccagctgcat taatgaatcg gccaacgcgc ggggagaggc ggcttgcgta    840

ttgggcgctc ttccgcttcc tcgctcactg actcgctgcg ctcg                     884
```

<210> SEQ ID NO 26
<211> LENGTH: 835
<212> TYPE: DNA
<213> ORGANISM: Artificial Sequence
<220> FEATURE:
<223> OTHER INFORMATION: Recombinant polynucleotide

<400> SEQUENCE: 26

```
tagtaaatga attttctgta tgaggttttg ctaaacaact ttcaacagtc tatgcggccc     60

cctttccaag tcggttcatc tctatgtctg tataatgtgc ggccgaattc agatcctctt    120

ctgagatgag tttttgttct gcggccgcgc tcgagacggt gaccagggtt ccctgacccc    180

aataccggaa cgtgttgtta acccaagccc gctttgtcgc gcaataatat accgcggtgt    240

cctcggcacg caggctgttc atttgcagat acagcgtgtt cttggaattg tcacgggaga    300

tggtgaaccg gcccttcacg gagtctgcgt agtatgtgct accgtttttg ttctgaatgg    360

ttgataccca ctctagaccc ttccctggag cctggcggac ccagctcata gccttatagc    420

taaccctaac tccggaggct gcacaggaga gacgcaggga ccccccaggc tgtaccaagc    480

ctcccccaga ctccaacagc tgcacctggg ccatggccgg ctaggccgca tagaaaggta    540

ccactaaagg aattgcgaat aataattttt tcattatgac tgtctccttg aaatagaatt    600

tgcatgcaag cttggcgtaa tcatggtcat agctgtttcc tgtgtgaaat tgttatccgc    660
```

```
tcacaattcc acacaacata cgagccggaa gcataaagtg taaagcctgg ggtgcctaat    720

gagtgagcta actcacattt aattgcgttg cgctcactgc ccgctttcca gtcgggaaac    780

ctgtcgtgcc agctgcatta atgaatcggc caacgcgcgg ggagaggcgg tttgc         835


<210> SEQ ID NO 27
<211> LENGTH: 978
<212> TYPE: DNA
<213> ORGANISM: Artificial Sequence
<220> FEATURE:
<223> OTHER INFORMATION: Recombinant polynucleotide

<400> SEQUENCE: 27

tagtaaatga attttctgta tgaggttttg ctaaacaact ttcacagtct atgcggcccc     60

ctttccagtc ggttcatctc tatgtctgta taatgtgcgg ccgaattcag atcctcttct    120

gagatgagtt tttgttctgc ggccgcgctc gagacggtga ccagggttcc ctgaccccaa    180

gaccacaagg aggacgtctg accctcctca ctattccgcc gccccttccg tctcgcgcaa    240

taatataccg cggtgtcctc ggcacgcagg ctgttcattt gcagatacag cgtgttcttg    300

gaattgtcac gggagatggt gaaccggccc ttcacggagt ctgcgtagta tgtgctaccg    360

tcacgcttac gaatggttga tacccactct agacccttcc ctggagcctg gcggacccag    420

cccatatact aatagttaaa gctatatccg gaggctgcac aggagagacg cagggacccc    480

ccaggctgta ccaagcctcc cccagactcc aacagctgca cctgggccat ggccggctgg    540

gccgcataga aaggtaccac taaaggaatt gcgaataata atttttttcat tatgactgtc    600

tccttgaaat agaatttgca tgcaagcttg gcgtaatcat ggtcatagct gtttcctgtg    660

tgaaattgtt atccgctcac aattccacac aacatacgag ccggaagcat aaagtgtaaa    720

gcctggggtg cctaatgagt gagctaactc acattaattg cgttgcgctc actgcccgct    780

ttccagtcgg gaaacctgtc gtgccagctg cattaatgaa tcggccaacg cgcgggggag    840

aggcggtttg cgtattgggc gctcttccgc ttccttcgct cactgactcg ctgcgctcgg    900

tcgttcggct gcgggcgagc ggtatcagct cactcaaagg cggtaatacg gttatccaca    960

gaatcagggg ataacgca                                                  978


<210> SEQ ID NO 28
<211> LENGTH: 841
<212> TYPE: DNA
<213> ORGANISM: Artificial Sequence
<220> FEATURE:
<223> OTHER INFORMATION: Recombinant polynucleotide

<400> SEQUENCE: 28

aaatgaattt tctgtatgag gtttccgcta aacaactttc aacagtctat gcggcccccct     60

ttccaagtcg gttcatctct atgtctgtat aatgtgcggc cgaattcaga tcctcttctg    120

agatgagttt ttgttctgcg gccgcgctcg agacggtgac cagggttccc tgaccccaag    180

accgcaactc ggacttaata ttattcaact cattccgatg acgaacccta ctcgcgcaat    240

aatataccgc ggtgtcctcg gcacgcaggc tgttcatttg cagatacagc gtgttcttgg    300

aattgtcacg ggagatggtg aaccggccct tcacggagtc tgcgtagtat gtgctaccgt    360

catggctacg aatgcttgat acccactcta gacccttccc tggagcctgg cggacccagg    420

ccatattcta agagataacc ttaaatccgg aggctgcaca ggagagacgc agggaccccc    480

caggctgtac caagcctccc ccagactcca acagctgcac ctgggccatg gccggctggg    540

ccgcatagaa aggtaccact aaaggaattg cgaataataa tttttcatt atgactgtct    600
```

ccttgaaata gaatttgcat gcaagcttgg cgtaatcatg gtcatagctg tttcctgtgt 660
gaaattgtta tcccgctcac aatttccaca caacgtacga gccggaagca taaagtgtaa 720
agcctggggt gcctaatgag tgagctaact cacattaatt gcgtttgcgc tcactgcccg 780
atttccagtc gggaaacctg tcgtgccagc tgcattaatg aatcggccaa cgcgcgggga 840
g 841

<210> SEQ ID NO 29
<211> LENGTH: 568
<212> TYPE: DNA
<213> ORGANISM: Artificial Sequence
<220> FEATURE:
<223> OTHER INFORMATION: Recombinant polynucleotide

<400> SEQUENCE: 29
taaacaactt tcaacagtct atgcggcccc ctttcccgtc ggtttatctc tatgtctgta 60
taatgtgcgg ccgaattcag atcctcttct gagatgagtt tttgttctgc ggccgcgctc 120
gagacggtga ccagggttcc ctgaccccaa aagtacatgg tggggttctt cacccacggc 180
caccgccttc tcgcgcaata atataccgcg gtgtcctcgg cacgcaggct gttcatttgc 240
agatacagcg tgttcttgga attgtcacgg gagatggtga accggccctt cacggagtct 300
gcgtagtatg tgctaccgtt tttcgtctga atggttgata cccactctag acccttccct 360
ggagcctggc ggacccaggc cataaactaa ttggtaaact taactccgga ggctgcacag 420
gagagacgca gggacccccc aggctgtacc aagcctcccc cagactccaa cagctgcacc 480
tgggccatgg ccggctgggc cgcatagaaa ggtaccacta aaggaattgc gaataataat 540
ttttttcatt atgactgtct ccttgaaa 568

<210> SEQ ID NO 30
<211> LENGTH: 860
<212> TYPE: DNA
<213> ORGANISM: Artificial Sequence
<220> FEATURE:
<223> OTHER INFORMATION: Recombinant polynucleotide

<400> SEQUENCE: 30
gttagtaaat gaattttctg tatgaggttt tcgctaaaca actttcaaca gtctatgcgg 60
ccccctttcc aagtcggttc atctctatgt ctgtataatg tgcggccgaa ttcagatcct 120
cttctgagat gagtttttgt tctgcggccg cgctcgagac ggtgaccagg gttccctgac 180
cccaatacga cagcttctcc gtacgcccct tacgtctcgc gcaataatat accgcggtgt 240
cctcggcacg caggctgttc atttgcagat acagcgtgtt cttggaattg tcacgggaga 300
tggtgaaccg gcccttcacg gagtctgcgt agtatgtgct accgtctttc ccctaaatgg 360
ctgataccca ctctagaccc ttccctggag cctggcggac ccaggccata ttgttatagc 420
taaacgtaaa tccggaggct gcacaggaga gacgcaggga ccccccaggc tgtaccaagc 480
ctcccccaga ctccaacagc tgcacctggg caatggccgg ctgggccgca tagaaaggta 540
ccactaaagg aattgcgaat aataattttt tcattatgac tgtctccttg aaatagaatt 600
tgcatgcaag cttggcgtaa tcatggtcat agctgtttcc tgtgtgaaat tgttatccgc 660
tcacaattcc acacaacata cgagccggac agcataaagt gtaaaagccc tggggtgcct 720
aacgagtgag ctaactcaca ttaattgcgt tgcgctcact gccccgcttt ccagtcgggg 780
aaacccgtcg tgcccagctg cattaatgaa tcggcccaac gcgcggggag aggccggttt 840
gcgtattgcg ccgctcttcc 860

<210> SEQ ID NO 31
<211> LENGTH: 774
<212> TYPE: DNA
<213> ORGANISM: Artificial Sequence
<220> FEATURE:
<223> OTHER INFORMATION: Recombinant polynucleotide

<400> SEQUENCE: 31
ttagtaaatg aattttctgt atgaggtttt gctaaacaac tttcaacagt ctatgcggcc 60
ccctttcaag tcggttcatc tctatgtctg tataatgtgc ggccgaattc agatcctctt 120
ctgagatgag tttttgttct gcggccgcgc tcgagacggt gaccagggtt ccctgacccc 180
aagacctcat cttggcggtc ccatgcaaac ccaaacgccc tctcgcgcaa taatataccg 240
cggtgtcctc ggcacgcagg ctgttcattt gcagatacag cgtgttcttg gaattgtcac 300
gggagatggt gaaccggccc ttcacggagt ctgcgtagta tgtgctaccg tctgtcgcac 360
caatggctga tacccactct agacccttcc ctggagcctg gcggacccag cccatagcct 420
aagggttaaa cttaactccg gaggctgcac aggagagacg cagggacccc ccaggctgta 480
ccaagcctcc cccagactcc aacagctgca cctgggccat ggccggctgg gccgcataga 540
aaggtaccac taaaggaatt gcgaataata attttttcat tatgactgtc tccttgaaat 600
agaatttgca tgcaagcttg gcgtaatcat ggtcatagct gtttcctgtg tgaaattgtt 660
atccgctcac aattccacac aacatacgag ccggaagcat aaagtgtaaa gcgctggggt 720
gcctaatgag tgagctaact cacattaatt gcgttgcgct cactgcgccg cttt 774

<210> SEQ ID NO 32
<211> LENGTH: 757
<212> TYPE: DNA
<213> ORGANISM: Artificial Sequence
<220> FEATURE:
<223> OTHER INFORMATION: Recombinant polynucleotide

<400> SEQUENCE: 32
taaacaactt tcaacagtct atgcggcccc ctttccagtc ggttcatctc tatgtctgta 60
taatgtgcgg ccgaattcag atcctcttct gagatgagtt tttgttctgc ggccgcgctc 120
gagacggtga ccagggttcc ctgaccccaa gaccgcacct aggcgggctt cctacgcccc 180
aaccgtgtcg cgcaataata taccgcggtg tcctcggcac gcaggctgtt catttgcaga 240
tacagcgtgt tcttggaatt gtcacgggag atggtgaacc ggcccttcac ggagtctgcg 300
tagtatgtgc taccgtttct gccaagaatg gttgataccc actctagacc cttccctgga 360
gcctggcgga cccaggtcat aacctaattg gtaacgttaa ctccggaggc tgcacaggag 420
agacgcaggg accccccagg ctgtaccaag cctcccccag actccaacag ctgcacctgg 480
gccatggccg gctgggccgc atagaaaggt accactaaag gaattgcgaa taataatttt 540
ttcattatga ctgtctcctt gaaatagaat ttgcatgcaa gcttggcgta atcatggtca 600
tagctgtttc ctgtgtgaaa ttgttatccg ctcacaattc cacacaacat acgagccgga 660
agcataaagt gtaaaagcct ggggtgccta atgagtgagc taactcacat taattgcgtt 720
tgcgctcact gcccgctttc cagtcgggga aacctgt 757

<210> SEQ ID NO 33
<211> LENGTH: 805
<212> TYPE: DNA
<213> ORGANISM: Artificial Sequence
<220> FEATURE:
<223> OTHER INFORMATION: Recombinant polynucleotide

<400> SEQUENCE: 33

```
ctaaacaact ttcaacagtc tatgcggccc cctttccaag tcggttcatc tctatgtctg     60

tataatgtgc ggccgaattc agatcctctt ctgagatgag tttttgttct gcggccgcgc    120

tcgagacggt gaccggggtt ccctgacccc aatagcggaa gttggcggta cgcctcctcc    180

tacccgcgca ataatatacc gcggtgtcct cggcacgcag gctgttcatt tgcagataca    240

gcgtgttctt ggaattgtca cgggagatgg tgaaccggcc cttcacggag tctgcgtagt    300

atgtgctacc gcttccgata gcaatggttg atacccactc tagacccttc cctggagcct    360

ggcggaccca gcccatatcc taagtgttaa acctatatcc ggaggctgca caggagagac    420

gcagggaccc cccaggctgt accaagcctc ccccagactc caacagctgc acctgggcca    480

tggccggctg ggccgcatag aaaggtacca ctaaaggaat tgcgaataat aatttttttca    540

ttatgactgt ctccttgaaa tagaatttgc atgcaagctt ggcgtaatca tggtcatagc    600

tgtttcctgt gtaaaattgt tatccgctca caattccaca caacatacga gccggaagca    660

taaagtgtaa agcctggggt gcctaatgag tgagctaact cacattaatt tgcgttgcgc    720

tcactgtccg ctttccagtc ggaaacctgt cgtgccagct gcattaatga atcggccaac    780

gcgcggggag aggcggtttg cgtat                                          805
```

<210> SEQ ID NO 34
<211> LENGTH: 862
<212> TYPE: DNA
<213> ORGANISM: Artificial Sequence
<220> FEATURE:
<223> OTHER INFORMATION: Recombinant polynucleotide

<400> SEQUENCE: 34

```
tagtaaatga attttctgta tgaggttttg ctaaacaact ttcaacagtc tatgcggccc     60

cctttccaag tcggttcatt tctatgtctg tataatgtgc ggccgaattc agatcctctt    120

ctgagatgag tttttgttct gcggccgcgc tcgagacggt gaccagggtt ccctgacccc    180

aatagcgcaa ctgctgggtt ctaagacgac gtgtcgcgca ataatatacc gcggtgtcct    240

cggcacgcag gctgttcatt tgcagataca gcgtgttctt ggaattgtca cgggagatgg    300

tgaaccggcc cttcacggag tctgcgtagt atgtgctacc gtctcgctta acaatggttg    360

atacccactc tagacccttc cctggagcct ggcggaccca gcccataatc taagtgttaa    420

cgctatctcc ggaggctgca caggagagac gcagggaccc cccaggctgt accaagcctc    480

ccccagactc caacagctgc acctgggcca tggccggctg ggccgcatag aaaggtacca    540

ctaaaggaat tgcgaataat aatttttttca ttatgactgt ctccttgaaa tagaatttgc    600

atgcaagctt ggcgtaatca tggtcatagc tgtttcctgt gtgaaattgt tatccgctca    660

caattccaca caacatacga gccggaagca taaagtgtaa agcctggggt gcctaatgag    720

tgagctaact cacattaatt gcgttgcgct cactgccccg ctttccagtc gggaaacctg    780

tcgtgccagc tgcattaatg aaatcggccc aacgcgcggg gagagggcgg tttgcgtatt    840

gggcgctctt ccgcttcctc gc                                             862
```

<210> SEQ ID NO 35
<211> LENGTH: 658
<212> TYPE: DNA
<213> ORGANISM: Artificial Sequence
<220> FEATURE:

<223> OTHER INFORMATION: Recombinant polynucleotide

<400> SEQUENCE: 35
ccggttcatc tctatgtctg tataatgtgc ggccgaattc agatcctctt ctgagatgag 60
tttttgttct gcggccgcgc tcgagacggt gaccagggtt ccctgacccc aagactgcac 120
cttctaggga cgacgcccag tactcgcgca ataatatacc gcggtgtcct cggcacgcag 180
gctgttcatt tgcagataca gcgtgttctt ggaattgtca cgggagatgg tgaaccggcc 240
cttcacggag tctgcgtagt atgtgctacc gctatggtta gcaatggttg atacccactc 300
tagacccttc cctggagcct ggcggaccca gctcataacc taattgctaa cgttaactcc 360
ggaggctgca caggagagac gcagggaccc cccaggctgt accaagcctc ccccagactc 420
caacagctgc acctgggcca tggccggctg ggccgcatag aaaggtacca cctaaaggaa 480
ttgcgaataa taatttttc attatgactg cctccttgaa atacaatttg catgcaagct 540
tggcgtactc atggccatag ctgttttcct gtgtgaaatt gttatccgct cacaattcca 600
cacaacatac gagccggacg cataaagtgt aaagcctggg gtgccctaat gagtgagc 658

<210> SEQ ID NO 36
<211> LENGTH: 788
<212> TYPE: DNA
<213> ORGANISM: Artificial Sequence
<220> FEATURE:
<223> OTHER INFORMATION: Recombinant polynucleotide

<400> SEQUENCE: 36
ctaaacaact ttcaacagtc tatgcggccc cctttccagt cggttcatct ctatgtctgt 60
ataatgtgcg gccgaattca gatcctcttc tgagatgagt ttttgttctg cggccgcgct 120
cgagacggtg accagggttc cctgacccca agactggatc gactgcgtca cctaacgctt 180
attcccctcc cgatttcccg cgcaataata taccgcggtg tcctcggcac gcaggctgtt 240
catttgcaga tacagcgtgt tcttggaatt gtcacgggag atggtgaacc ggcccttcac 300
ggagtctgcg tagtatgtgc taccgtctct gttcaaaatg gttgataccc actctagacc 360
cttccctgga gcctggcgga cccaggtcat aacctaagcg ctaatgttaa ctccggaggc 420
tgcacaggag agacgcaggg acccccccagg ctgtaccaag cctcccccag actccaacag 480
ctgcacctgg gccatggccg gctgggccgc atagaaaggt accactaaag gaattgcgaa 540
taataatttt ttcattatga ctgtctcctt gaaatagaat ttgcatgcaa gcttggcgta 600
atcatggtca tgctgtttcc tgtgtgaaat tgttatccgc tcacaattcc acacaacata 660
cgagccggaa gcataaagtg taaagcctgg ggtgcctaat gagtgagcta actcacatta 720
attgcgttgc gctcactgcc cgctttccag tcgggaaaac ctgtcgtgcc agctgcatta 780
atgaatcg 788

<210> SEQ ID NO 37
<211> LENGTH: 788
<212> TYPE: DNA
<213> ORGANISM: Artificial Sequence
<220> FEATURE:
<223> OTHER INFORMATION: Recombinant polynucleotide

<400> SEQUENCE: 37
tagtaaatga attttctgta tgaggttttg ctaaacaact ttcacagtct atgcggcccc 60
ctttccaagt cggttcatct ctatgtctgt ataatgtgcg gccgaattca gatcctcttc 120
tgagatgagt ttttgttctg cggccgcgct cgagacggtg accagggttc cctgacccca 180

```
agactgcacc ggcgtcgtcc tcttccgcga cgttctcgcg caataatata ccgcggtgtc    240

ctcggcacgc aggctgttca tttgcagata cagcgtgttc ttggaattgt cacgggagat    300

ggtgaaccgg cccttcacgg agtctgcgta gtatgtgcta ccgctattgg tctaaatgcc    360

tgatacccac tctagaccct tccctggagc ctggcggacc cagctcatat acttagggat    420

aaggctatct ccggaggctg cacaggagag acgcagggac cccccaggct gtaccaagcc    480

tcccccagac tccaacagct gcacctgggc catggccggc tgggccgcat agaaaggtac    540

cactaaagga attgcgaata ataatttttt cattatgact gtctccttga aatagaattt    600

gcatgcaagc ttggcgtaat catggtcata gctgtttcct gtgtgaaatt gttatccgct    660

cacaattcca cacaacatac gagccggaaa gcataaagtg taaagcctgg ggtgcctaat    720

gagtgagcta actcacatta attgcgttgc gctcactgcc cgctttccag tcgggaaacc    780

tgtcgtgc                                                              788
```

```
<210> SEQ ID NO 38
<211> LENGTH: 865
<212> TYPE: DNA
<213> ORGANISM: Artificial Sequence
<220> FEATURE:
<223> OTHER INFORMATION: Recombinant polynucleotide

<400> SEQUENCE: 38

gttagtaaat gaattttctg tatgaggttc ccgctaaaca actttcaaca gtctatgcgg     60

ccccctttcc aagtcggttc atctctatgt ctgtataatg tgcggccgaa ttcagatcct    120

cttctgagat gagtttttgt tctgcggccg cgctcgagac ggtgaccagg gttccctgac    180

cccaagactg catgggcttg gtcgtactac gcttcttccc tctcgcgcaa taatataccg    240

cggtgtcctc ggcacgcagg ctgttcattt gcagatacag cgtgttcttg gaattgtcac    300

gggagatggt gaaccggccc ttcacggagt ctgcgtagta tgtgctaccg cttctgctct    360

aaatggttga tacccactct agacccttcc ctggagcctg gcggacccag ctcatatact    420

tatggataaa cgtaaatccg gaggctgcac aggagagacg cagggacccc ccaggctgta    480

ccaagcctcc cccagactcc aacagctgca cctgggccat ggccggctgg gccgcataga    540

aaggtaccac taaaggaatt gcgaataata attttttcat tatgactgtc tccttgaaat    600

agaatttgca tgcaagcttg gcgtaatcat ggtcatagct gtttcctgtg tgaaattgtt    660

atccgctcac caattccaca caacatacga gcccggaagc ataaagtgta aagcctgggg    720

gtgcctaatg agtgagctaa ctcacattaa ttgcgttgcg ctcactgccc gctttccagt    780

cggaaacctg tcgtgccagc tgcattaatg aatcggccaa gcgcggggag aggcggtttg    840

cgtattgggc gctcttccgc ttcct                                           865
```

```
<210> SEQ ID NO 39
<211> LENGTH: 743
<212> TYPE: DNA
<213> ORGANISM: Artificial Sequence
<220> FEATURE:
<223> OTHER INFORMATION: Recombinant polynucleotide

<400> SEQUENCE: 39

acagtctatg cggccccctt tccaagtcgg ttcatctcta tgtctgtata atgtgcggcc     60

gaattcagat cctcttctga gatgagtttt tgttctgcgg ccgcgctcga gacggtgacc    120

agggttccct gaccccaata cgggaccgtc ttgtaatcac tattccgctt tcccgcgcaa    180
```

```
taatataccg cggtgtcctc ggcacgcagg ctgttcattt gcagatacag cgtgttcttg    240

gaattgtcac gggagatggt gaaccggccc ttcacggagt ctgcgtagta tgtgctaccg    300

tctttgccca taatggttga tacccactct agacccttcc ctggagcctg gcggacccag    360

gtcataatct aatagttaac cgtatatccg gaggctgcac aggagagacg cagggacccc    420

ccaggctgta ccaagcctcc cccagactcc aacagctgca cctgggccat ggccggctgg    480

gccgcataga aaggtaccac taaaggaatt gcgaataata attttttcat tatgactgtc    540

tccttgaaat agaatttgca tgcaagcttg gcgtaatcat ggtcatagct gtttcctgtg    600

tgaaatttgt tatccgctca caattccaca caacataacg agccggaagc ataaagtgta    660

aagcctgggg tgcctaatga gtgagctaac tcacattaa tttgcgttgc gcttcactgc     720

cccgctttcc agtccgggaa acc                                            743
```

<210> SEQ ID NO 40
<211> LENGTH: 787
<212> TYPE: DNA
<213> ORGANISM: Artificial Sequence
<220> FEATURE:
<223> OTHER INFORMATION: Recombinant polynucleotide

<400> SEQUENCE: 40

```
aatgaatttt ctgtatgagg ttttgctaaa caactttcaa cagtctatgc ggcccccttt     60

ccagtcggtt catctctatg tctgtataat gtgcggccga attcagatcc tcttctgaga    120

tgagtttttg ttctgcggcc gcgctcgaga cggtgaccag ggttccctga ccccaaaact    180

tcaaggggtg cgtcaaatca cccctcgacc tccttcccgc gcaataatat accgcggtgt    240

cctcggcacg caggctgttc atttgcagat acagcgtgtt cttggaattg tcacgggaga    300

tggtgaaccg gcccttcacg gagtctgcgt agtatgtgct accgtcatgg ccaccaatgg    360

ttgataccca ctctagaccc ttccctggag cctggcggac ccagctcata ttctaatggt    420

taaccataaa tccggaggct gcacaggaga gacgcaggga ccccccaggc tgtaccaagc    480

ctcccccaga ctccaacagc tgcacctggg ccatggccgg ctgggccgca tagaaaggta    540

ccactaaagg aattgcgaat aataattttt tcattatgac tgtctccttg aaatagaatt    600

tgcatgcaag cttggcgtaa tcatggtcat agctgtttcc tgtgtgaaat tgttatccgc    660

tcacaattcc acaccaacat acgagccgga agcataaagt gtaaagcctg gggtgcctaa    720

aatgagtgag ctaactcaca ttaattgcgt tgcgctcact gccgctttcc agtcgggaaa    780

cctgtcg                                                              787
```

<210> SEQ ID NO 41
<211> LENGTH: 765
<212> TYPE: DNA
<213> ORGANISM: Artificial Sequence
<220> FEATURE:
<223> OTHER INFORMATION: Recombinant polynucleotide

<400> SEQUENCE: 41

```
gctaaacaac tttcaacagt ctatgcggcc ccctttccag tcggttcatc tctatgtctg     60

tataatgtgc ggccgaattc agatcctctt ctgagatgag tttttgttct gcggccgcgc    120

tcgagacggt gaccagggtt ccctgacccc aagacctcac cttcgtctgc ctagcccccct   180

ccaacaacct cctaagtgtc gcgcaataat ataccgcggt gtcctcggca cgcaggctgt    240

tcatttgcag atacagcgtg ttcttggaat tgtcacggga gatggtgaac cggcccttca    300

cggagtctgc gtagtatgtg ctaccgtctg ggttcctaat tgttgatacc cactctagac    360
```

```
ccttccctgg agcctggcgg acccaggcca tagtctaatt gctaaaccta tatccggagg    420

ctgcacagga gagacgcagg gaccccccag gctgtaccaa gcctccccca gactccaaca    480

gctgcacctg ggccatggcc ggctgggccg catagaaagg taccactaaa ggaattgcga    540

ataataattt tttcattatg actgtctcct tgaaatagaa tttgcatgca agcttggcgt    600

aatcatggtc atagctgttt cctgtgtgaa attgttatcc gctcacaatt ccacacaaca    660

tacgagccgg aagcataaag tgtaagcctg gggtgcctaa tgagtgagct aactcacatt    720

aattgcgttg cgctcactgc ccgctttcca gtcgggaaac ctgt                     765
```

```
<210> SEQ ID NO 42
<211> LENGTH: 984
<212> TYPE: DNA
<213> ORGANISM: Artificial Sequence
<220> FEATURE:
<223> OTHER INFORMATION: Recombinant polynucleotide

<400> SEQUENCE: 42

tagtaaatga attttctgta tgaggttttg ctaaacaact ttcaacagtc tatgcggccc     60

cctttccagt cggttcatct ctatgtctgt ataatgtgcg gccgaattca gatcctcttc    120

tgagatgagt ttttgttctg cggccgcgct cgagacggtg accagggttc cctgacccca    180

atacctcacc ttctggttcc aaagcgccct acctgtcgcg caataatata ccgcggtgtc    240

ctcggcacgc aggctgttca tttgcagata cagcgtgttc ttggaattgt cacgggagat    300

ggtgaaccgg cccttcacgg agtctgcgta gtatgtgcta ccgttaccgg tctgaatgct    360

tgatacccac tctagaccct tccctggagc ctggcggacc cagcccatat tcttagggct    420

aaccctatct ccggaggctg cacaggagag acgcagggac cccccaggct gtaccaagcc    480

tcccccagac tccaacagct gcacctgggc catggccggc tgggccgcat agaaaggtac    540

cactaaagga attgcgaata ataatttttt cattatgact gtctccttga aatagaattt    600

gcatgcaagc ttggcgtaat catggtcata gctgtttcct gtgtgaaatt gttatccgct    660

cacaattcca cacaacatac gagccggaag cataaagtgt aaagcctggg gtgcctaatg    720

agtgagctaa ctcacattaa ttgcgttgcg ctcactgccc gctttccagt cgggaacctg    780

ttcgtgccag ctgcattaat gaaatcggcc aacgcgcggg ggagaggcgg tttgcgtatt    840

gggcgctctt ccgcttcctc gctcactgac tcgctgcgct cggacgttcg gctgcggcga    900

gcggtaccag ctcactcaaa ggcggtaata cggttatcca cagaatcagg ggataacgca    960

gcgaaagaac atgtgagcaa aagg                                           984
```

```
<210> SEQ ID NO 43
<211> LENGTH: 850
<212> TYPE: DNA
<213> ORGANISM: Artificial Sequence
<220> FEATURE:
<223> OTHER INFORMATION: Recombinant polynucleotide

<400> SEQUENCE: 43

aatgaatttt ctgtatgagg ttttgctaaa caactttcac agtctatgcg gcccccttc      60

caagtcggtt catctctatg tctgtataat gtgcggccga attcagatcc tcttctgaga    120

tgagtttttg ttctgcggcc gcgctcgaga cggtgaccag ggttccctga ccccaatacg    180

gcaactggtt ctacatcatc ctcttaggac ccgcgcaata atataccgcg gtgtcctcgg    240

cacgcaggct gttcatttgc agatacagcg tgttcttgga attgtcacgg gagatggtga    300
```

accggccctt cacggagtct gcgtagtatg tgctaccgtt tctggcacta atggttgata 360
cccactctag acccttccct ggagcctggc ggacccagcc catagcctaa gagctaagcc 420
taaatccgga ggctgcacag gagagacgca gggacccccc aggctatacc aagcctcccc 480
cagactccaa cagctgcacc tgggccatgg ccggctgggc cgcatagaaa ggtaccacta 540
aaggaattgc gaataataat tttttcatta tgactgtctc cttgaaatag aatttgcatg 600
caagcttggc gtaatcatgg tcatagctgt ttcctgtgtg aaattgttat ccgctcacaa 660
ttccacacaa catacgagcc gggaagcata aagtgtaaag cctggggtg cctaatgagt 720 gagctaactc accattaatt gcgttgcgct cactgcccgc tttccagtcg ggaaacctgt 780
cgtgccagct gcattaatga atcggcccac gcgcgggaga ggcggtttgc gtattgggcg 840
ctcttccgct 850

<210> SEQ ID NO 44
<211> LENGTH: 407
<212> TYPE: DNA
<213> ORGANISM: Artificial Sequence
<220> FEATURE:
<223> OTHER INFORMATION: Recombinant polynucleotide

<400> SEQUENCE: 44
atggcccagg tgcagctgtt ggagtctggg ggaggcttgg tacagcctgg ggggtccctt 60
cgtctctcct gtgcagcctc cggagttaag attagccatt agaatatggc ctgggtccgc 120
caggctccag ggaagggtct agagtgggta tcaagcattg ggatgcgtag cggtagcaca 180
tactacgcag actccgtgaa gggccggttc accatctccc gtgacaattc caagaacacg 240
ctgtatctgc aaatgaacag cctgcgtgcc gaggacaccg cggtatatta ttgcgcgagt 300
tagaggcggt tgtcgtttcc gaacaagttc aagttttggg gtcagggaac cctggtcacc 360
gtctcgagcg cggccgcaga acaaaaactc atctcagaag aggatct 407

<210> SEQ ID NO 45
<211> LENGTH: 407
<212> TYPE: DNA
<213> ORGANISM: Artificial Sequence
<220> FEATURE:
<223> OTHER INFORMATION: Recombinant polynucleotide

<400> SEQUENCE: 45
atggcccagg tgcagctgtt ggagtctggg ggaggcttgg tacagcctgg ggggtccctg 60
cgtctctcct gtgcagcctc cggagttagg cttacccata agaatatggg ctgggtccgc 120
caggctccag ggaagggtct agagtgggta tcaagcattc gtggccgtga cggtagcaca 180
tactacgcag actccgtgaa gggccggttc accatctccc gtgacaattc caagaacacg 240
ctgtatctgc aaatgaacag cctgcgtgcc gaggacaccg cggtatatca ttgcgcgaga 300
ggtcggtagt atatgcgtcc gacgaccgtc cagttttggg gtcagggaac cctggtcacc 360
gtctcgagcg cggccgcaga acaaaaactc atctcagaag aggatct 407

<210> SEQ ID NO 46
<211> LENGTH: 401
<212> TYPE: DNA
<213> ORGANISM: Artificial Sequence
<220> FEATURE:
<223> OTHER INFORMATION: Recombinant polynucleotide

<400> SEQUENCE: 46
atggcccagg tgcagctgtt ggagtctggg ggaggcttgg tacagcctgg ggggtccctg 60

```
cgtctctcct gtgcagcctc cggagttaac attatctatt aggatatggc ctgggtccgc    120

caggctccag ggaagggtct agagtgggta tcaaccattc gtacgcgaag cggtagcaca    180

taatacgcag actccgtgaa gggccggttc accatctccc gtgacaattc caagaacacg    240

ctgtatctgc aaatgaacag cctgcgtgcc gaggacaccg cggtatatta ttgcgcgggt    300

aggaggaggc gtaccgccaa cttccgctat tggggtcagg gaaccctggt caccgtctcg    360

agcgcggccg cagaacaaaa actcatctca gaagaggatc t                        401
```

<210> SEQ ID NO 47
<211> LENGTH: 404
<212> TYPE: DNA
<213> ORGANISM: Artificial Sequence
<220> FEATURE:
<223> OTHER INFORMATION: Recombinant polynucleotide

<400> SEQUENCE: 47

```
atggcccagg tgcagctgtt ggagtctggg ggaggcttgg tacagcctgg ggggtccctg     60

cgtctctcct gtgcagcctc cggagttaag attagctatt agtctatggc ctgggtccgc    120

caggctccag ggaagggtct agagtgggta tcaagcattc tgatgcaaaa cggtagcaca    180

tactacgcag actccgtgaa gggccggttc accatctccc gtgacaattc caagaacacg    240

ctgtatctgc aaatgaacag cctgcgtgcc gaggacaccg cggtatatta ttgcgcgaca    300

acgagggtta ggcggccggc gaacatgaag tattggggtc agggaaccct ggtcaccgtc    360

tcgagcgcgg ccgcagaaca aaaactcatc tcagaagagg atct                     404
```

<210> SEQ ID NO 48
<211> LENGTH: 422
<212> TYPE: DNA
<213> ORGANISM: Artificial Sequence
<220> FEATURE:
<223> OTHER INFORMATION: Recombinant polynucleotide

<400> SEQUENCE: 48

```
atggcccagg tgcagctgtt ggagtctggg ggaggcttgg tacagcctgg ggggtccctg     60

cgtctctcct gtgcagcctc cggatatagg tttaactctt aggctatggg ctgggtccgc    120

caggctccag ggaagggtct agagtgggta tcaagcatta atatgcgagg cggtagcaca    180

tactacgcag actccgtgaa gggccggttc accatctccc gtgacaattc caagaacacg    240

ctgtatctgc aaatgaacag cctgcgtgcc gaggacaccg cggtatatta ttgcgcgaca    300

gttcctagga gtatgtggtg ggctggtctg actgcgaagc cgatcaggta ttggggtcag    360

ggaaccctgg tcaccgtctc gagcgcggcc gcagaacaaa aactcatctc agaagaggat    420

ct                                                                   422
```

<210> SEQ ID NO 49
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 49

```
atggcccagg tgcagctgtt ggagtctggg ggaggcttgg tacagcctgg ggggtccctg     60

cgtctctcct gtgcagcctc cggagttaag tttaccaatt agtatatggg ctgggtccgc    120

caggctccag ggaagggtct agagtgggta tcaagcatta tgacgcaaag cggtagcaca    180
```

tactacgcag actccgtgaa gggccggttc accatctccc gtgacaattc caagaacacg 240
ctgtatctgc aaatgaacag cctgcgtgcc gaggacaccg cggtatatta ttgcgcgggt 300
aggcgtggta agcggtggct tgtgtcgccg ctccggtatt ggggtcaggg aaccctggtc 360
accgtctcga gcgcggccgc agaacaaaaa ctcatctcag aagaggatct 410

<210> SEQ ID NO 50
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 50
atggcccagg tgcagctgtt ggagtctggg ggaggcttgg tacagcctgg ggggtccctg 60
cgtctctcct gtgcagcctc cggagttagg tttaaccatt agtttatgag ctgggtccgc 120
caggctccag ggaagggtct agagtgggta tcaggcatta atagccgaag cggtagcaca 180
tactacgcag actccgtgaa gggccggttc accatctccc gtgacaattc caagaacacg 240
ctgtatctgc aaatgaacag cctgcgtgcc gaggacaccg cggtatatta ttgcgcgagt 300
gcgcgtcggg cgccttttcg tacgaagtac atcaagtttt ggggtcaggg aaccctggtc 360
accgtctcga gcgcggccgc agaacaaaaa ctcatctcag aagaggatct 410

<210> SEQ ID NO 51
<211> LENGTH: 422
<212> TYPE: DNA
<213> ORGANISM: Artificial Sequence
<220> FEATURE:
<223> OTHER INFORMATION: Recombinant polynucleotide

<400> SEQUENCE: 51
atggcccagg tgcagctgtt ggagtctggg ggaggcttgg tacagcctgg ggggtccctg 60
cgtctctcct gtgcagcctc cggagatagg tttagcaatt aggctatgag ctgggtccgc 120
caggctccag ggaagggtct agagtgggta tcaggcatta ataccacaga cggtagcaca 180
tactacgcag actccgtgaa gggccggttc accatctccc gtgacaattc caagaacacg 240
ctgtatctgc aaatgaacag cctgcgtgcc gaggacaccg cggtatatta ttgcgcggca 300
cctcggcgtt tgaggggtag gccttggtct gtgccccaca agatggggtt ttggggtcag 360
ggaaccctgg tcaccgtctc gagcgcggcc gcagaacaaa aactcatctc agaagaggat 420
ct 422

<210> SEQ ID NO 52
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 52
atggcccagg tgcagctgtt ggagtctggg ggaggcttgg tacagcctgg ggggtccctg 60
cgtctctcct gtgcagcctc cggatttagg tttagccatt agtatatggg ctgggtccgc 120
caggctccag ggaagggtct agagtgggta tcaaccattg ctatgactaa cggtagcaca 180
tactacgcag actccgtgaa gggccggttc accatctccc gtgacaattc caagaacacg 240
ctgtatctgc aaatgaacag cctgcgtgcc gaggacaccg cggtatatta ttgcgcgaga 300
tggcatgggg ggaggaagtg gccgaagccc ttgacgtctt ggggtcaggg aaccctggtc 360
accgtctcga gcgcggccgc agaacaaaaa ctcatctcag aagaggatct 410

<210> SEQ ID NO 53
<211> LENGTH: 407
<212> TYPE: DNA
<213> ORGANISM: Artificial Sequence
<220> FEATURE:
<223> OTHER INFORMATION: Recombinant polynucleotide

<400> SEQUENCE: 53
atggcccagg tgcagctgtt ggagtctggg ggaggcttgg tacagcctgg ggggtccctg 60
cgtctctcct gtgcagcctc cggatatagg tttaacgatt agactatggc ctgggtccgc 120
caggctccag ggaagggtct agagtgggta tcaaccattg gtgccactaa cggtagcaca 180
tactacgcag actccgtgaa gggccggttc accatctccc gtgacaattc caagaacacg 240
ctgtatctgc aaatgaacag cctgcgtgcc gaggacaccg cggtatatta ttgcgcgaga 300
cggcgtaggc ttggtgcttc gcactacatg cggttttggg gtcagggaac cctggtcacc 360
gtctcgagcg cggccgcaga acaaaaactc atctcagaag aggatct 407

<210> SEQ ID NO 54
<211> LENGTH: 404
<212> TYPE: DNA
<213> ORGANISM: Artificial Sequence
<220> FEATURE:
<223> OTHER INFORMATION: Recombinant polynucleotide

<400> SEQUENCE: 54
atggcccagg tgcagctgtt ggagtctggg ggaggcttgg tacagcctgg ggggtccctg 60
cgtctctcct gtgcagcctc cggatataag tttaactctc actatatgag ctgggtccgc 120
caggctccag ggaagggtct agagtgggta tcaaccatta ggaaccgtga cggtagcaca 180
tactacgcag actccgtgaa gggccggttc accatctccc gtgacaattc caagaacacg 240
ctgtatctgc aaatgaacag cctgcgtgcc gaggacaccg cggtatatta ttgcgcgaga 300
taggcgaggc agcggccgac caacttctac tcttggggtc agggaaccct ggtcaccgtc 360
tcgagcgcgg ccgcagaaca aaaactcatc tcagaagagg atct 404

<210> SEQ ID NO 55
<211> LENGTH: 413
<212> TYPE: DNA
<213> ORGANISM: Artificial Sequence
<220> FEATURE:
<223> OTHER INFORMATION: Recombinant polynucleotide

<400> SEQUENCE: 55
atggcccagg tgcagctgtt ggagtctggg ggaggcttgg tacagcctgg ggggtccctg 60
cgtctctcct gtgcagcctc aggatttagg gttatcccta agtatatggg ctgggtccgc 120
caggctccag ggaagggtct agagtgggta tcaaccatta agacccgtga cggtagcaca 180
tactacgcag actccgtgaa gggccggttc accatctccc gtgacaattc caagaacacg 240
ctgtatctgc aaatgaacag cctgcgtgcc gaggacaccg cggtatatta ttgcgcgaga 300
gttaataggt ggaggttggc gactcccaac taggtcgagt cttggggtca gggaaccctg 360
gtcaccgtct cgagcgcggc cgcagaacaa aaactcatct cagaagagga tct 413

<210> SEQ ID NO 56
<211> LENGTH: 425
<212> TYPE: DNA

```
<213> ORGANISM: Artificial Sequence
<220> FEATURE:
<223> OTHER INFORMATION: Recombinant polynucleotide

<400> SEQUENCE: 56

atggcccagg tgcagctgtt ggagtctggg ggaggcttgg tacagcctgg ggggtccctg     60

cgtctctcct gtgcagcctc cggatttatg cttaacaatt aggatatgag ctgggtccgc    120

caggctccag ggaagggtct agagtgggta tcagccattc gtgccccaag cggtagcaca    180

tactacgcag actccgtgaa gggccggttc accatctccc gtgacaattc caagaacacg    240

ctgtatctgc aaatgaacag cctgcgtgcc gaggacaccg cggtatatta ttgcgcgaga    300

aagaagggga tggggaggtt tccgggtatg atgaggaagc cgcacatgcg cttttggggt    360

cagggaaccc tggtcaccgt ctcgagcgcg gccgcagaac aaaaactcat ctcagaagag    420

gatct                                                                425


<210> SEQ ID NO 57
<211> LENGTH: 431
<212> TYPE: DNA
<213> ORGANISM: Artificial Sequence
<220> FEATURE:
<223> OTHER INFORMATION: Recombinant polynucleotide

<400> SEQUENCE: 57

atggcccagg tgcagctgtt ggagtctggg ggaggcttgg tacagcctgg ggggtccctg     60

cgtctctcct gtgcagcctc cggagttacg attaacaatt agtatatggg ctgggtccgc    120

caggctccag ggaagggtct agagtgggta tcaagcattc ggaaccgtaa cggtagcaca    180

tactacgcag actccgtgaa gggccggttc accatctccc gtgacaattc caagaacacg    240

ctgtatctgc aaatgaacag cctgcgtgcc gaggacaccg cggtatatta ttgcgcgagt    300

tgtgggagga ggcgttgtcg gtatcggggg ggggattatc agcacaagtc gatgaggtat    360

tggggtcagg gaaccctggt caccgtctcg agcgcggccg cagaacaaaa actcatctca    420

gaagaggatc t                                                         431


<210> SEQ ID NO 58
<211> LENGTH: 419
<212> TYPE: DNA
<213> ORGANISM: Artificial Sequence
<220> FEATURE:
<223> OTHER INFORMATION: Recombinant polynucleotide

<400> SEQUENCE: 58

atggcccagg tgcagctgtt ggagtctggg ggaggcttgg tacagcctgg ggggtccctg     60

cgtctctcct gtgcagcctc cggatttaag tttagcgctt agtatatgag ctgggtccgc    120

caggctccag ggaagggtct agagtgggta tcaaccatta agatgaataa cggtagcaca    180

tactacgcag actccgtgaa gggccggttc accatctccc gtgacaattc caagcacacg    240

ctgtatctgc aaatgaacag cctgcgtgcc gaggacaccg cggtatatta ttgcgcgaga    300

ccgatggcgt ggcggggtaa tgtggtgcgg gccgagaact tgcggttttg gggtcaggga    360

accctggtca ccgtctcgag cgcggccgca gaacaaaaac tcatctcaga agaggatct     419


<210> SEQ ID NO 59
<211> LENGTH: 407
<212> TYPE: DNA
<213> ORGANISM: Artificial Sequence
<220> FEATURE:
<223> OTHER INFORMATION: Recombinant polynucleotide
```

<400> SEQUENCE: 59

```
atggcccagg tgcagctgtt ggagtctggg gaaggcttgg tacagcctgg ggggtccctg     60
cgtctctcct gtgcagcctc cggagttagg cttacccata agaatatggg ctgggtccgc    120
caggctccag ggaagggtct agagtgggta tcaagcattc gtggccgtga cggtagcaca    180
tactacgcag actccgtgaa gggccggttc accatctccc gtgacaattc caagaacacg    240
ctgtatctgc aaatgaacag cctgcgtgcc gaggacaccg cggtatatca ttgcgcgaga    300
ggtcggtagt atatgcgtcc gacgaccgtc cagttttggg gtcagggaac cctggtcacc    360
gtctcgagcg cggccgcaga acaaaaactc atctcagaag aggatct                  407
```

<210> SEQ ID NO 60
<211> LENGTH: 407
<212> TYPE: DNA
<213> ORGANISM: Artificial Sequence
<220> FEATURE:
<223> OTHER INFORMATION: Recombinant polynucleotide

<400> SEQUENCE: 60

```
atggcccagg tgcagctgtt ggagtctggg ggaggcttgg tacagcctgg ggggtccctg     60
cgtctctcct gtgcagcctc cggagttaag cttagccatt agaatatggg ctgggtccgc    120
caggctccag ggaagggtct agagtgggta tcaagcattg gtatccgtag cggtagcaca    180
tactacgcag actccgtgaa gggccggttc accatctccc gtgacaattc caagaacacg    240
ctgtatctgc aaatgaacag cctgcgtgcc gaggacaccg cggtatatca ttgcgcgaga    300
ggtcggtggt atttgtgtcc gaccacggtc cagttttggg gtcagggaac cctggtcacc    360
gtctcgagcg cggccgcaga acaaaaactc atctcagaag aggatct                  407
```

<210> SEQ ID NO 61
<211> LENGTH: 407
<212> TYPE: DNA
<213> ORGANISM: Artificial Sequence
<220> FEATURE:
<223> OTHER INFORMATION: Recombinant polynucleotide

<400> SEQUENCE: 61

```
atggcccagg tgcagctgtt ggagtctggg ggaggcttgg tacagcctgg ggggtccctt     60
cgtctctcct gtgcagcctc cggagttaag attagccgtt agaatatggc ctgggtccgc    120
caggctccag ggaagggtct agagtgggta tcaagcattg ggatgcgtag cggtagcaca    180
tactacgcag actccgtgaa gggccggttc accatctccc gtgacaattc caagaacacg    240
ctgtatctgc aaatgaacag cctgcgtgcc gaggacaccg cggtatatta ttgcgcgagt    300
tagaggcggt tgtcgtttcc gaacaagttc aagttttggg gtcagggaac cctggtcacc    360
gtctcgagcg cggccgcaga acaaaaactc atctcagaag aggatct                  407
```

<210> SEQ ID NO 62
<211> LENGTH: 404
<212> TYPE: DNA
<213> ORGANISM: Artificial Sequence
<220> FEATURE:
<223> OTHER INFORMATION: Recombinant polynucleotide

<400> SEQUENCE: 62

```
atggcccagg tgcagctgtt ggagtctggg ggaggcttgg tacagcctgg ggggtccctg     60
cgtctctcct gtgcagcctc cggagttagg gttagctata aggctatgag ctgggtccgc    120
```

```
caggctccag ggaagggtct agagtgggta tcaaccattc agaacaaaaa cggtagcaca    180

tactacgcag actccgtgaa gggccggttc accatctccc gtgacaattc caagaacacg    240

ctgtatctgc aaatgaacag cctgcgtgcc gaggacaccg cggtatatta ttgcgcgaca    300

aagcgggctt gggttaacaa cacgttccgg tattggggtc agggaaccct ggtcaccgtc    360

tcgagcgcgg ccgcagaaca aaaactcatc tcagaagagg atct                    404
```

```
<210> SEQ ID NO 63
<211> LENGTH: 422
<212> TYPE: DNA
<213> ORGANISM: Artificial Sequence
<220> FEATURE:
<223> OTHER INFORMATION: Recombinant polynucleotide

<400> SEQUENCE: 63

atggcccagg tgcagctgtt ggagtctggg ggaggcttgg tacagcctgg ggggtccctg     60

cgtctctcct gtgcagcctc cggatatagc tttaactatt agtatatggg ctgggtccgc    120

caggctccag ggaagggtct agagtgggta tcaaccattc gtaagcgtga cggtagcaca    180

tactacgcag actccgtgaa gggccggttc accatctccc gtgacaattc caagaacacg    240

ctgtatctgc aaatgaacag cctgcgtgcc gaggacaccg cggtatatta ttgcgcgaga    300

cggaaggggc ggcggaatag tgaggagggt cagacgtcct ccttgtggtc ttggggtcag    360

ggaaccctgg tcaccgtctc gagcgcggcc gcagaacaaa aactcatctc agaagaggat    420

ct                                                                   422
```

```
<210> SEQ ID NO 64
<211> LENGTH: 407
<212> TYPE: DNA
<213> ORGANISM: Artificial Sequence
<220> FEATURE:
<223> OTHER INFORMATION: Recombinant polynucleotide

<400> SEQUENCE: 64

atggcccagg tgcagctgtt ggagtctggg ggaggcttgg tacagcctgg ggggtccctt     60

cgtctctcct gtgcagcctc cggagttaag attagccatt agaatatggc ctgggtccgc    120

caggctccag ggaagggtct agagtgggta tcaagcattg ggatgcgtag cggtagcaca    180

tactacgcag actccgtgaa gggccggttc accatctccc gtgacaattc caagaacacg    240

ctgtatctgc aaatgaacag cctgcgtgcc gaggacaccg cggtatatta ttgcgcgagt    300

tagaggcggt tgtagtttcc gaacaagttc aagttttggg gtcagggaac cctggtcacc    360

gtctcgagcg cggccgcaga acaaaaactc atctcagaag aggatct                 407
```

```
<210> SEQ ID NO 65
<211> LENGTH: 422
<212> TYPE: DNA
<213> ORGANISM: Artificial Sequence
<220> FEATURE:
<223> OTHER INFORMATION: Recombinant polynucleotide

<400> SEQUENCE: 65

atggcccagg tgcagctgtt ggagtctggg ggaggcttgg tacagcctgg ggggtccctg     60

cgtctctcct gtgcagcctc cggatttaag gttatctctt agaatatggc ctgggtccgc    120

caggctccag ggaagggtct agagtgggta tcaagcattc gtagccatga cggtagcaca    180

tactacgcag actccgtgaa gggccggttc accatctccc gtgacaattc caagaacacg    240

ctgtatctgc aaatgaacag cctgcgtgcc gaggacaccg cggtatatta ttgcgcgagt    300
```

```
agggttcgtc atcggaatga gttgaataat attaagtccg agttgcggtc ttggggtcag    360

ggaaccctgg tcaccgtctc gagcgcggcc gcagaacaaa aactcatctc agaagaggat    420

ct                                                                   422
```

```
<210> SEQ ID NO 66
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 66

atggcccagg tgcagctgtt ggagtctggg ggaggcttgg tacagcctgg ggggtccctg     60

cgtctctcct gtgcagcctc cggagttaag tttaccaatt agtttatggc ctgggtccgc    120

caggctccag ggaagggtct agagtgggta tcaaccattc agacgaaaaa cggtagcaca    180

tactacgcag actccgtgaa gggccggttc accatctccc gtgacaattc caagaacacg    240

ctgtatctgc aaatgaacag cctgcgtgcc gaggacaccg cggtatatta ttgcgcgaga    300

aggcggtggc cgtgggtgaa gaaccccacc atgtactttt ggggtcaggg aaccctggtc    360

accgtctcga gcgcggccgc agaacaaaaa ctcatctcag aagaggatct               410
```

```
<210> SEQ ID NO 67
<211> LENGTH: 401
<212> TYPE: DNA
<213> ORGANISM: Artificial Sequence
<220> FEATURE:
<223> OTHER INFORMATION: Recombinant polynucleotide

<400> SEQUENCE: 67

attgcccagg tgcagctgtt ggagtctggg ggaggcttgg tacagcctgg ggggtccctg     60

cgtctctcct gtgcagcctc cggatttacg tttagctata acaatatggc ctgggtccgc    120

caggctccag ggaagggtct agagtgggta tcagccattt aggggaaaga cggtagcaca    180

tactacgcag actccgtgaa gggccggttc accatctccc gtgacaattc caagaacacg    240

ctgtatctgc aaatgaacag cctgcgtgcc gaggacaccg cggtatatta ttgcgcgaga    300

cgtaaggggc gtacggagaa gctgtcgtat tggggtcagg gaaccctggt caccgtctcg    360

agcgcggccg cagaacaaaa actcatctca gaagaggatc t                        401
```

```
<210> SEQ ID NO 68
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 68

atggcccagg tgcagctgtt ggagtctggg ggaggcttgg tacagcctgg ggggtccctg     60

cgtctctcct gtgcagcctc cggagttaag tttaaccctt aggctatggg ctgggtccgc    120

caggctccag ggaagggtct agagtgggta tcagccattg gtgcgacaga cggtagcaca    180

tactacgcag actccgtgaa gggccggttc accatctccc gtgacaattc caagaacacg    240

ctgtatctgc aaatgaacag cctgcgtgcc gaggacaccg cggtatatta ttgcgcgaga    300

gggcgtttgg gtttgcatgg gaccgccaag atgaggtctt ggggtcaggg aaccctggtc    360

accgtctcga gcgcggccgc agaacaaaaa ctcatctcag aagaggatct               410
```

<210> SEQ ID NO 69
<211> LENGTH: 407
<212> TYPE: DNA
<213> ORGANISM: Artificial Sequence
<220> FEATURE:
<223> OTHER INFORMATION: Recombinant polynucleotide

<400> SEQUENCE: 69

```
atggcccagg tgcagctgtt ggagtctggg ggaggcttgg tacagcctgg ggggtccctg     60

cgtctctcct gtgcagcctc cggagttaac gttaccaatt aggttatgac ctgggtccgc    120

caggctccag ggaagggtct agagtgggta tcaaccattc ttggcagaaa cggtagcaca    180

tactacgcag actccgtgaa gggccggttc accatctccc gtgacaattc caagaacacg    240

ctgtatctgc aaatgaacag cctgcgtgcc gaggacaccg cggtatatta ttgcgcgaca    300

cggttggggc gtaggaagcc cgcctaggtg cggtcttggg gtcagggaac cctggtcacc    360

gtctcgagcg cggccgcaga acaaaaactc atctcagaag aggatct                  407
```

<210> SEQ ID NO 70
<211> LENGTH: 401
<212> TYPE: DNA
<213> ORGANISM: Artificial Sequence
<220> FEATURE:
<223> OTHER INFORMATION: Recombinant polynucleotide

<400> SEQUENCE: 70

```
atggcccagg tgcagctgtt ggagtctggg ggaggcttgg tacagcctgg ggggtccctg     60

cgtctctcct gtgcagcctc cggatatagg tttaacactt aggatatggg ctgggtccgc    120

caggctccag ggaagggtct agagtgggta tcaaccattg ctatcggaag cggtagcaca    180

tactacgcag actccgtgaa gggccggttc accatctccc gtgacaattc caagaacacg    240

ctgtatctgc aaatgaacag cctgcgtgcc gaggacaccg cggtatatta ttgcgcgggt    300

aggaggaggc gtaccgccaa cttccgctat tggggtcagg gaaccccggt caccgtctcg    360

agcgcggccg cagaacaaaa actcatctca gaagaggatc t                        401
```

<210> SEQ ID NO 71
<211> LENGTH: 401
<212> TYPE: DNA
<213> ORGANISM: Artificial Sequence
<220> FEATURE:
<223> OTHER INFORMATION: Recombinant polynucleotide

<400> SEQUENCE: 71

```
atggcccagg tgcagctgtt ggagtctggg ggaggcttgg tacagcctgg ggggtccctg     60

cgtctctcct gtgcagcctc cggagatagc gttaacactt agattatggg ctgggtccgc    120

caggctccag ggaagggtct agagtgggta tcaaccattg ttaagcgaga cggtagcaca    180

tactacgcag actccgtgaa gggccggttc accatctccc gtgacaattc caagaacacg    240

ctgtatctgc aaatgaacag cctgcgtgcc gaggacaccg cggtatatta ttgcgcgaca    300

cgtcgtctta gaacccagca gttgcgctat tggggtcagg gaaccctggt caccgtctcg    360

agcgcggccg cagaacaaaa actcatctca gaagaggatc t                        401
```

<210> SEQ ID NO 72
<211> LENGTH: 401
<212> TYPE: DNA
<213> ORGANISM: Artificial Sequence
<220> FEATURE:
<223> OTHER INFORMATION: Recombinant polynucleotide

<400> SEQUENCE: 72
atggcccagg tgcagctgtt ggagtctggg ggaggcttgg tacagcctgg ggggtccctg 60
cgtctctcct gtgcagcctc cggagttaac gttagcaatt aggttatgag ctgggtccgc 120
caggctccag ggaagggtct agagtgggta tcaaccattg ctaaccatag cggtagcaca 180
tactacgcag actccgtgaa gggccggttc accatctccc gtgacaattc caagaacacg 240
ctgtatctgc aaatgaacag cctgcgtgcc gaggacaccg cggtatatta ttgcgcgagt 300
actgggcgtc gtccctagaa ggtgcagtct tggggtcagg gaaccctggt caccgtctcg 360
agcgcggccg cagaacaaaa actcatctca gaagaggatc t 401

<210> SEQ ID NO 73
<211> LENGTH: 416
<212> TYPE: DNA
<213> ORGANISM: Artificial Sequence
<220> FEATURE:
<223> OTHER INFORMATION: Recombinant polynucleotide

<400> SEQUENCE: 73
atggcccagg tgcagctgtt ggagtctggg ggaggcttgg tacagcctgg ggggtccctg 60
cgtctctcct gtgcagcctc cggagttaac attagcgctt aggttatgac ctgggtccgc 120
caggctccag ggaagggtct agagtgggta tcaaccattt tgaacagaga cggtagcaca 180
tactacgcag actccgtgaa gggccggttc accatctccc gtgacaattc caagaacacg 240
ctgtatctgc aaatgaacag cctgcgtgcc gaggacaccg cggtatatta ttgcgcggga 300
aatcgggagg ggaataagcg ttaggtgacg cagtcgatcc agtcttgggg tcagggaacc 360
ctggtcaccg tctcgagcgc ggccgcagaa caaaaactca tctcagaaga ggatct 416

<210> SEQ ID NO 74
<211> LENGTH: 404
<212> TYPE: DNA
<213> ORGANISM: Artificial Sequence
<220> FEATURE:
<223> OTHER INFORMATION: Recombinant polynucleotide

<400> SEQUENCE: 74
atggcccagg tgcagctgtt ggagtctggg ggaggcttgg tacagcctgg ggggtccctg 60
cgtctctcct gtgcagcctc cggagatagc cttatcccta agtatatgag ctgggtccgc 120
caggctccag ggaagggtct agagtgggta tcaggcattt agaccaatag cggtagcaca 180
tactacgcag actccgtgaa gggccggttc accatctccc gtgacaattc caagaacacg 240
ctgtatctgc aaatgaacag cctgcgtgcc gaggacaccg cggtatatta ttgcgcgaga 300
acgtcgcgga agaggacgac gccggtgcag tcttggggtc agggaaccct ggtcaccgtc 360
tcgagcgcgg ccgcagaaca aaaactcatc tcagaagagg atct 404

<210> SEQ ID NO 75
<211> LENGTH: 407
<212> TYPE: DNA
<213> ORGANISM: Artificial Sequence
<220> FEATURE:
<223> OTHER INFORMATION: Recombinant polynucleotide

<400> SEQUENCE: 75
atggcccagg tgcagctgtt ggagtctggg ggaggcttgg tacagcctgg ggggtccctg 60
cgtctctcct gtgcagcctc cggatttacg tttatccata agtatatgag ctgggtccgc 120

```
caggctccag ggaagggtct agagtgggta tcaaccattt agagcagaag cggtagcaca    180

tactacgcag actccgtgaa gggccggttc accatctccc gtgacaattc caagaacacg    240

ctgtatctgc aaatgaacag cctgcgtgcc gaggacaccg cggtatatta ttgcgcgaga    300

gggaagaagc gtagtacgac caagcccatg cagtcttggg gtcagggaac cctggtcacc    360

gtctcgagcg cggccgcaga acaaaaactc atctcagaag aggatct                  407


<210> SEQ ID NO 76
<211> LENGTH: 404
<212> TYPE: DNA
<213> ORGANISM: Artificial Sequence
<220> FEATURE:
<223> OTHER INFORMATION: Recombinant polynucleotide

<400> SEQUENCE: 76

atggcccagg tgcagctgtt ggagtctggg ggaggcttgg tacagcctgg ggggtccctg     60

cgtctctcct gtgcagcctc cggatatacg gttaactatt agattatgac ctgggtccgc    120

caggctccag ggaagggtct agagtgggta tcaaccatta tgggcaaaga cggtagcaca    180

tactacgcag actccgtgaa gggccggttc accatctccc gtgacaattc caagaacacg    240

ctgtatctgc aaatgaacag cctgcgtgcc gaggacaccg cggtatatta ttgcgcggga    300

aagcggaata gtgattacaa gacggtcccg tattggggtc agggaaccct ggtcaccgtc    360

tcgagcgcgg ccgcagaaca aaaactcatc tcagaagagg atct                     404


<210> SEQ ID NO 77
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 77

atggcccagg tgcagctgtt ggagtctggg ggaggcttgg tacagcctgg ggggtccctg     60

cgtctctcct gtgcagcctc cggatttatg gttaaccatt agaatatgag ctgggtccgc    120

caggctccag ggaagggtct agagtgggta tcaaccattg gtggccatga cggtagcaca    180

tactacgcag actccgtgaa gggccggttc accatctccc gtgacaattc caagaacacg    240

ctgtatctgc aaatgaacag cctgcgtgcc gaggacaccg cggtatatta ttgcgcggga    300

aggaggtcga ggggtgattt gacgcacccc ttgaagtttt ggggtcaggg aaccctggtc    360

accgtctcga gcgcggccgc agaacaaaaa ctcatctcag aagaggatct               410


<210> SEQ ID NO 78
<211> LENGTH: 416
<212> TYPE: DNA
<213> ORGANISM: Artificial Sequence
<220> FEATURE:
<223> OTHER INFORMATION: Recombinant polynucleotide

<400> SEQUENCE: 78

atggcccagg tgcagctgtt ggagtctggg ggaggcttgg tacagcctgg ggggtccctg     60

cgtctctcct gtgcagcctc cggatatagg tttagcaatt agactatggc ctgggtccgc    120

caggctccag ggaagggtct agagtgggta tcaacaatta ggaacccaga cggtagcaca    180

tactacgcag actccgtgaa gggccggttc accatctccc gtgacaattc caagaacacg    240

ctgtatctgc aaatgaacag cctgcgtgcc gaggacaccg cggtatatta ttgcgcgaca    300

cttaggaggt tgttggaggg ggctaggcag acgaaggtga ggtcttgggg tcagggaacc    360
```

```
ctggtcaccg tctcgagcgc ggccgcagaa caaaaactca tctcagaaga ggatct        416


<210> SEQ ID NO 79
<211> LENGTH: 404
<212> TYPE: DNA
<213> ORGANISM: Artificial Sequence
<220> FEATURE:
<223> OTHER INFORMATION: Recombinant polynucleotide

<400> SEQUENCE: 79

atggcccagg tgcagctgtt ggagtctggg ggaggcttgg tacagcctgg ggggtccctg     60

cgtctctcct gtgcagcctc cggagatagg gttagcccta agaatatggg ctgggtccgc    120

caggctccag ggaagggtct agagtgggta tcaagcattc agaccggtaa cggtagcaca    180

tactacgcag actccgtgaa gggccggttc accatctccc gtgacaattc caagaacacg    240

ctgtatctgc aaatgaacag cctgcgtgcc gaggacaccg cggtatatta ttgcgcgaca    300

ggtagggcgc tttggaacca gaaggtgagg tattggggtc agggaaccct ggtcaccgtc    360

tcgagcgcgg ccgcagaaca aaaactcatc tcagaagagg atct                     404


<210> SEQ ID NO 80
<211> LENGTH: 404
<212> TYPE: DNA
<213> ORGANISM: Artificial Sequence
<220> FEATURE:
<223> OTHER INFORMATION: Recombinant polynucleotide

<400> SEQUENCE: 80

atggcccagg tgcagctgtt ggagtctggg ggaggcttgg tatagcctgg ggggtccctg     60

cgtctctcct gtgcagcctc cggatttagg cttagctctt aggctatggg ctgggtccgc    120

caggctccag ggaagggtct agagtgggta tcaaccatta gtgccagaaa cggtagcaca    180

tactacgcag actccgtgaa gggccggttc accatctccc gtgacaattc caagaacacg    240

ctgtatctgc aaatgaacag cctgcgtgcc gaggacaccg cggtatatta ttgcgcgggt    300

cctaagagga tgatgtagaa ccagttgccg tattggggtc agggaaccct ggtcaccgtc    360

tcgagcgcgg ccgcagaaca aaaactcatc tcagaagagg atct                     404


<210> SEQ ID NO 81
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 81

atggcccagg tgcagctgtt ggagtctggg ggaggcttgg tacagcctgg ggggtccctg     60

cgtctctcct gtgcagcctc cggatataag tttagcgatt aggctatgag ctgggtccgc    120

caggctccag ggaagggtct agagtgggta tcagccattt atgtgcatga cggtagcaca    180

tactacgcag actccgtgaa gggccggttc accatctccc gtgacaattc caagaacacg    240

ctgtatctgc aaatgaacag cctgcgtgcc gaggacaccg cggtatatta ttgcgcgaga    300

tggcaggatc tgctgatgta ggaggaggcg ttgccctatt ggggtcaggg aaccctggtc    360

accgtctcga gcgcggccgc agaacaaaaa ctcatctcag aagaggatct               410


<210> SEQ ID NO 82
<211> LENGTH: 401
<212> TYPE: DNA
```

```
<213> ORGANISM: Artificial Sequence
<220> FEATURE:
<223> OTHER INFORMATION: Recombinant polynucleotide

<400> SEQUENCE: 82

atggcccagg tgcagctgtt ggagtctggg ggaggcttgg tacagcctgg ggggtccctg     60

cgtctctcct gtgcagcctc cggatatatc tttagcgatt aggctatggg ctgggtccgc    120

caggctccag ggaagggtct agagtgggta tcaagcattc ataccgcaaa cggtagcaca    180

tactacgcag actccgtgaa gggccggttc accatctccc gtgacaattc caagaacacg    240

ctgtatctgc aaatgaacag cctgcgtgcc gaggacaccg cggtatatta ttgcgcgggt    300

tatagtgagt ggtaggacga gatgcagtat tggggtcagg gaaccctggt caccgtctcg    360

agcgcggccg cagaacaaaa actcatctca gaagaggatc t                        401


<210> SEQ ID NO 83
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 83

atggcccagg tgcagctgtt ggagtctggg ggaggcttgg tacagcctgg ggggtccctg     60

cgtctctcct gtgcagcctc cggatataag tttagcgatt aggctatgag ctgggtccgc    120

caggctccag ggaagggtct agagtgggta tcagccattt atgtgcatga cggtagcaca    180

tactacgcag actccgtgaa gggccggttc accatctccc gtgacaattc caagaacacg    240

ctgtatctgc aaatgaacag catgcgtgcc gaggacaccg cggtatatta ttgcgcgaga    300

tggcaggatc agctgatgta ggaggaggcg ttgccctatt ggggtcaggg aaccctggtc    360

accgtctcga gcgcggccgc agaacaaaaa ctcatctcag aagaggatct               410


<210> SEQ ID NO 84
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 84

atggcccagg tgcagctgtt ggagtctggg ggaggcttgg tacagcctgg ggggtccctg     60

cgtctctcct gtgcagcctc cggatataag tttagcgatt aggctatgag ctgggtccgc    120

caggctccag ggaagggtct agagtgggta tcagccattt atgtgcatga cggtagcaca    180

tactacgcag actccgtgaa gggccggttc accatctccc gtgacaattc caagaacacg    240

ctgtatctgc aaatgaacag catgcgtgcc gaggacaccg cggtatatta ttgcgcgaga    300

tggcaggatc tgctgatgta ggaggaggcg ttgccctatt ggggtcaggg aaccctggtc    360

accgtctcga gcgcggccgc agaacaaaaa ctcatctcag aagaggatct               410


<210> SEQ ID NO 85
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 85

atggcccagg tgcagctgtt ggagtctggg ggaggcttgg tacagcctgg ggggtccctg     60
```

cgtctctcct gtgcagcctc cggatataag tttagcgatt aggctatgag ctgggtccgc 120
caggctccag ggaagggtct agagtgggta tcagccattt atgtgcatga cggtagcaca 180
tactacgcag actccgtgaa gggccggttc accatctccc gtgacaattc caagaacacg 240
ctgtatctgc aaatgaacag catgcgtgcc gaggacaccg cggtatatta ttgcgcgaga 300
tggcaggatc tgatgatgta ggaggaggcg ttgccctatt ggggtcaggg aaccctggtc 360
accgtctcga gcgcggccgc agaacaaaaa ctcatctcag aagaggatct 410

<210> SEQ ID NO 86
<211> LENGTH: 401
<212> TYPE: DNA
<213> ORGANISM: Artificial Sequence
<220> FEATURE:
<223> OTHER INFORMATION: Recombinant polynucleotide

<400> SEQUENCE: 86
atggcccagg tgcagctgtt ggagtctggg ggaggcttgg tacagcctgg ggggtccctg 60
cgtctctcct gtgcagcctc cggagttaca tttaacgatg agtttatgac ctgggtccgc 120
caggctccag ggaagggtct agagtgggta tcaaccatta gtaaccgtaa cggtagcaca 180
tactacgcag actccgtgaa gggccggttc accatctccc gtgacaattc caagaacacg 240
ctgtatctgc aaatgaacag cctgcgtgcc gaggacaccg cggtatatta ttgcgcgggt 300
gatttgttgg gtcccgcgcc ggtgggctct tggggtcagg gaaccctggt caccgtctcg 360
agcgcggccg cagaacaaaa actcatctca gaagaggatc t 401

<210> SEQ ID NO 87
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 87
atggcccagg tgcagctgtt ggagtctggg ggaggcttgg tacagcctgg ggggtccctg 60
cgtctctcct gtgcagcctc cggatataag tttagcgatt aggctatgag ctgggtccgc 120
caggctccag ggaagggtct agagtgggta tcagccattt atgtgcatga cggtagcaca 180
tcctacgcag actccgtgaa gggccggttc accatctccc gtgacaattc caagaacacg 240
ctgtatctgc aaatgaacag cctgcgtgcc gaggacaccg cggtatacta ttgcgcgaga 300
tggcaggatc atctgatgta gtaggaggcg atgccctatt ggggtcaggg aaccctggtc 360
accgtctcga gcgcggccgc agaacaaaaa ctcatctcag aagaggatct 410

<210> SEQ ID NO 88
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 88
atggcccagg tgcagctgtt ggagtctggg ggaggcttgg tacagcctgg ggggtccctg 60
cgtctctcct gtgcagcctc cggatataag tttagcgatt aggctatgag ctgggtccgc 120
caggctccag ggaagggtct agagtgggta tcagccattt atgtgcatga cggtagcaca 180
tactacgcag actccgtgaa gggccggttc accatctccc gtgacaattc caagaacacg 240
ctgtatctgc aaatgaacag cctgcgtgcc gaggacaccg cggtatatta ttgcgcgaga 300
tggcaggatc atctgatgta ggaggaggcg atgccctatt ggggtcaggg aaccctggtc 360
accgtctcga gcgcggccgc agaacaaaaa ctcatctcag aagaggatct 410

<210> SEQ ID NO 89
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 89
atggcccagg tgcagctgtt ggagtctggg ggaggcttgg tacagcctgg ggggtccctg 60
cgtctctcct gtgcagcctc cggatataag tttagcgatt aggctatgag ctgggtccgc 120
caggctccag ggaagggtct agagtgggta tcagccattt atgtgcatga cggtagcaca 180
tactacgcag actccgtgaa gggccggttc accatctccc gtgacaattc caagaacacg 240
ctgtatctgc aaatgaacag catgcgtgcc gaggacaccg cggtatacta ttgcgcgaga 300
tggcaggatc atcttatgta ggaggaggag atgccctatt ggggtcaggg aaccctggtc 360
accgtctcga gcgcggccgc agaacaaaaa ctcatctcag aagaggatct 410

<210> SEQ ID NO 90
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 90
atggcccagg tgcagctgtt ggagtctggg ggaggcttgg tacagcctgg ggggtccctg 60
cgtctctcct gtgcagcctc cggatataag tttagcgatt aggctatgag ctgggtccgc 120
caggctccag ggaagggtct agagtgggta tcagccattt atgtgcatga cggtagcaca 180
tattacgcag actccgtgaa gggccggttc accatgttcc gtgacaattc caagaacacg 240
ctgtatctgc agatgaacag catgcgtgcc gaggacaccg cggtatatta ttgcgcgaga 300
tggcaggatc agatgatgta ggaggaggcg ttgccctatt ggggtcaggg aaccctggtc 360
accgtctcga gcgcggccgc agaacaaaaa ctcatctcag aagaggatct 410

<210> SEQ ID NO 91
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 91
atggcccagg tgcagctgtt ggagtctggg ggaggcttgg tacagcctgg ggggtccctg 60
cgtctctcct gtgcagcctc cggatataag tttagcgatt aggctatgag ctgggtccgc 120
caggctccag ggaagggtct agagtgggta tcagccattt atgtgcatga cggtagcaca 180
tattacgcag actccgtgaa gggccggttc accatcttcc gtgacaattc caagaacacg 240
ctgtatctgc agatgaacag catgcgtgcc gaggacaccg cggtatatta ttgcgcgaga 300
tggcaggatc tgatgatgta ggaggaggcg ttgccctatt ggggtcaggg aaccctggtc 360
accgtctcga gcgcggccgc agaacaaaaa ctcatctcag aagaggatct 410

<210> SEQ ID NO 92
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 92

```
atggcccagg tgcagctgtt ggagtctggg ggaggcttgg tacagcctgg ggggtccctg     60

cgtctctcct gtgcagcctc cggatataag tttagcgatt aggctatgag ctgggtccgc    120

caggctccag ggaagggtct agagtgggta tcagccattt atgtgcatga cggtagcaca    180

tactacgcag actccgtgaa gggccggttc accatctccc gtgacaattc caagaacacg    240

ctgtatctgc aaatgaacag catgcgtgcc gaggacaccg cggtatatta ttgcgcgaga    300

tggcaggatc ttcttatgta ggaggaggcg ttgccctatt ggggtcaggg aaccctggtc    360

accgtctcga gcgcggccgc agaacaaaaa ctcatctcag aagaggatct              410
```

<210> SEQ ID NO 93
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 93

```
atggcccagg tgcagctgtt ggagtctggg ggaggcttgg tacagcctgg ggggtccctg     60

cgtctctcct gtgcagcctc cggatataag tttagcgatt aggctatgag ctgggtccgc    120

caggctccag ggaagggtct agagtgggta tcagccattt atgtgcatga cggtagcaca    180

tactacgcag actccgtgaa gggccggttc accatctccc gtgacaattc caagaacacg    240

ctgtatctgc aaatgaacag catgcgtgcc gaggacaccg cggtatatta ttgcgcgaga    300

tggcaggatc tgattatgta ggaggaggcg ttgccctatt ggggtcaggg aaccctggtc    360

accgtctcga gcgcggccgc agaacaaaaa ctcatctcag aagaggatct              410
```

<210> SEQ ID NO 94
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 94

```
atggcccagg tgcagctgtt ggagtctggg ggaggcttgg tacagcctgg ggggtccctg     60

cgtctctcct gtgcagcctc cggatataag tttagcgatt aggctatgag ctgggtccgc    120

caggctccag ggaagggtct agagtgggta tcagccattt atgtgcatga cggtagcaca    180

tattacgcag actccgtgaa gggccggttc accatctccc gtgacaattc caagaacacg    240

ctgtatctgc aaatgaacag catgcgtgcc gaggacaccg cggtatatta ttgcgcgaga    300

tggcaggatc agatgatgta ggaggaggcg ttgccctatt ggggtcaggg aaccctggtc    360

accgtctcga gcgcggccgc agaacaaaaa ctcatctcag aagaggatct              410
```

<210> SEQ ID NO 95
<211> LENGTH: 401
<212> TYPE: DNA
<213> ORGANISM: Artificial Sequence
<220> FEATURE:
<223> OTHER INFORMATION: Recombinant polynucleotide

<400> SEQUENCE: 95
atggcccagg tgcagctgtt ggagtctggg ggaggcttgg tacagcctgg ggggtccctg 60
cgtctctcct gtgcagcctc cggatttaag attatcgatt acgatatggg ctgggtccgc 120
caggctccag ggaagggtct agagtgggta tcaagcattt agaacagaag cggtagcaca 180
tactacgcag actccgtgaa gggccggttc accatctccc gtgacaattc caagaacacg 240
ctgtatctgc aaatgaacag cctgcgtgcc gaggacaccg cggcatatta ttgcgcgggt 300
tatgggaggt aggacgagac ggtcgactat tggggtcagg gaaccctggt caccgtctcg 360
agcgcggccg cagaacaaaa actcatctca gaagaggatc t 401

<210> SEQ ID NO 96
<211> LENGTH: 401
<212> TYPE: DNA
<213> ORGANISM: Artificial Sequence
<220> FEATURE:
<223> OTHER INFORMATION: Recombinant polynucleotide

<400> SEQUENCE: 96
atggcccagg tgcagctgtt ggagtctggg ggaggcttgg tacagcctgg ggggtccctg 60
cgtctctcct gtgcagcctc cggatatatg attagcgatt agtatatggg ctgggtccgc 120
caggctccag ggaagggtct agagtgggta tcaggcattg ataccagtag cggtagcaca 180
tactacgcag actccgtgaa gggccggttc accatctccc gtgacaattc caagaacacg 240
ctgtatctgc aaatgaacag cctgcgtgcc gaggacaccg cggtatatta ttgcgcgaca 300
ctgctttctt cggaccccaa cgtcaactat tggggtcagg gaaccctggt caccgtctcg 360
agcgcggccg cagaacaaaa actcatctca gaagaggatc t 401

<210> SEQ ID NO 97
<211> LENGTH: 335
<212> TYPE: DNA
<213> ORGANISM: Artificial Sequence
<220> FEATURE:
<223> OTHER INFORMATION: Recombinant polynucleotide

<400> SEQUENCE: 97
tcctgtgcag cctccggata tatctttaga gattaggcta tgggctgggt ccgccaggct 60
ccagggaagg gtctagagtg ggtatcaagc attcataccg caaacggtag cacatactac 120
gcagactccg tgaagggccg gttcaccatc tcccgtgaca attccaagaa cacgctgtat 180
ctgcaaatga acagcctgcg tgccgaggac accgcggtat attattgcgc gggttatagt 240
gagtggtagg acgagatgca gtattggggt cagggaaccc tggtcaccgt ctcgagcgcg 300
gccgcagaac aaaaactcat ctcagaagag gatct 335

<210> SEQ ID NO 98
<211> LENGTH: 377
<212> TYPE: DNA
<213> ORGANISM: Artificial Sequence
<220> FEATURE:
<223> OTHER INFORMATION: Recombinant polynucleotide

<400> SEQUENCE: 98
aggcttggta cagcttgggg ggtccctgcg tctctcctgt gcagcctccg gatataagtt 60
tagcgattag gctatgagct gggtccgcca ggctccaaga agggtctaga gtgggtatca 120
gccatttatg tgcatgacgg tagcacatac tacgcagact ccgtgaaggg ccggttcacc 180
atgttccgtg tcaattccaa gaacacgctg tatctgcaaa tgaacagcat gcgtgccgag 240

```
gacaccgcgg tatattattg cgcgagatgg caggatcata tgatgtagga ggaggcgttg    300

ccctattggg gtcagggaac cctggtcacc gtctcgagcg cggccgcaga acaaaaactc    360

atctcagaag aggatct                                                   377
```

<210> SEQ ID NO 99
<211> LENGTH: 401
<212> TYPE: DNA
<213> ORGANISM: Artificial Sequence
<220> FEATURE:
<223> OTHER INFORMATION: Recombinant polynucleotide

<400> SEQUENCE: 99

```
atggcccagg tgcagctgtt ggagtctggg ggaggcttgg tacagcctgg ggggtccctg     60

cgtctatcct gtgcagcctc cggatatatc tttagcgatt aggctatggg ctgggtccgc    120

caggctccag ggaagggtct agagtgggta tcaagcattc aaaccgcaaa cggtagcacc    180

tcctccgcag actccgtgaa gggccggttc accatctccc gtgacaattc caagaacacg    240

ctgtatctgc aaatgaacag cctgcgtgcc gaggacaccg cggtatatta ttgcgcgggt    300

tatagtgagt ggtaggacga gatgcagtat tggggtcagg gaaccctggt caccgtatcg    360

agcgcggccg cagaacaaaa actcatctct ttagaggatc t                        401
```

<210> SEQ ID NO 100
<211> LENGTH: 359
<212> TYPE: DNA
<213> ORGANISM: Artificial Sequence
<220> FEATURE:
<223> OTHER INFORMATION: Recombinant polynucleotide

<400> SEQUENCE: 100

```
cagcctgggg ggtccctgtg tctctcctgt gcagcctccg gatatatctt tagcgattag     60

gctatgggct gggtccgcca ggctccaggg aagggtctag agtgggtatc aagcattcat    120

accgcaaacg gtagcacata ctacgcagac tccgtgaagg gccggttcac catctcccgt    180

gacaattcca agaacacgct gtatctgcaa atgaacagcc tgcgtgccga ggacacctcg    240

gtatattatt gcgcgggtta tagtgagtgg taggacgaga tgcagtattg gggtcaggga    300

accctggtca ccgtctcgag cgcggccgca gaacaaaaac tcatctcaga agaggatct     359
```

<210> SEQ ID NO 101
<211> LENGTH: 337
<212> TYPE: DNA
<213> ORGANISM: Artificial Sequence
<220> FEATURE:
<223> OTHER INFORMATION: Recombinant polynucleotide

<400> SEQUENCE: 101

```
tatcctgtgc agcctccgga tatatcttta gcgattaggc tatgggcagg gtccgccagg     60

ctccagggaa gggtctagag tgggtatcaa gcattcatac cgcaaacggt agcacatact    120

tcacaaaatc cgtgaagggc cggttcacca tctcccgtga caattccaag aacacgctgt    180

atctgcaaat gaacagcctg cgtgccgagg acaccgcggt atattattgc gcgggttata    240

gtgagtggta ggacgagatg cagtattggg gtcagggaac cctggtcacc gtctcgagcg    300

cggccgcaga acaaaaactc atttctttag aggatct                             337
```

<210> SEQ ID NO 102
<211> LENGTH: 407
<212> TYPE: DNA

<213> ORGANISM: Artificial Sequence
<220> FEATURE:
<223> OTHER INFORMATION: Recombinant polynucleotide

<400> SEQUENCE: 102
atggcccagg tgcagctgtt ggagtctggg ggaggcttgg tacagcctgg ggggtccctg 60
cgtctctcct gtgcagcctc cggatttatc gttagcgctt aggctatgag ctgggtccgc 120
caggctccag ggaagggtct agagtgggta tcaggcattg ggcgggaaaa cggtagcaca 180
tactacgcag actccgtgaa gggccggttc accatctccc gtgacaattc caagaacacg 240
ctgtatctgc aaatgaacag cctgcgtgcc gaggacaccg cggtatatta ttgcgcgagt 300
actaaggagc tgtttgagtc cacgaccgtc ggctcttggg gtcagggaac cctggtcacc 360
gtctcgggcg cggccgcaga acaaaaactc atctcagaag aggatct 407

<210> SEQ ID NO 103
<211> LENGTH: 401
<212> TYPE: DNA
<213> ORGANISM: Artificial Sequence
<220> FEATURE:
<223> OTHER INFORMATION: Recombinant polynucleotide

<400> SEQUENCE: 103
atggcccagg tgcagctgtt ggagtctggg ggaggcttgg tacagcctgg ggggtccctg 60
cgtctctcct gtgcagcctc cggatttaag attatcgatt acgatatggg ctgggtccgc 120
caggctccag ggaagggtct agagtgggta tcaagcattt agaacagaag cggtagcaca 180
tactacgcag actccgtgaa gggccggttc accatctccc gtgacaattc caagaacacg 240
ctgtatctgc aaatgaacag cctgcgtgcc gaggacaccg cggcatatta ttgcgcgggt 300
tatgggaggt aggacgagac ggtcgactct tggggtcagg gaaccctggt caccgtctcg 360
agcgcggccg cagaacaaaa actcatctca gaagaggatc t 401

<210> SEQ ID NO 104
<211> LENGTH: 422
<212> TYPE: DNA
<213> ORGANISM: Artificial Sequence
<220> FEATURE:
<223> OTHER INFORMATION: Recombinant polynucleotide

<400> SEQUENCE: 104
atggcccagg tgcagctgtt ggagtctggg ggaggcttgg tacagcctgg ggggtccctg 60
cgtctctcct gtgcagcctc cggagttaac cttagcgatg acactatggg ctgggtccgc 120
caggctccag ggaagggtct agagtgggta tcaggcattg ataacacaga cggtagcaca 180
tactacgcag actccgtgaa gggccggttc accatctccc gtgacaattc caagaacacg 240
ctgtatctgc aaatgaacag cctgcgtgcc gaggacaccg cggtatatta ttgcgcggga 300
gagggtctgc agttggtggc gctgcttggt gattcggcgg acgtggactt ttggggtcag 360
ggaaccctgg tcaccgtctc gagcgcggcc gcagaacaaa aactcatctc agaagaggat 420
ct 422

<210> SEQ ID NO 105
<211> LENGTH: 395
<212> TYPE: DNA
<213> ORGANISM: Artificial Sequence
<220> FEATURE:
<223> OTHER INFORMATION: Recombinant polynucleotide

<400> SEQUENCE: 105

```
atgcttccgg ctcgtatgtt gtgtggaatt gtgagcggat aacaatttca cacaggaaac     60

agctatgacc atgattacgc caagcttaac tctcagtata tgagctgggt ccgccaggct    120

ccagggaagg gtctagagtg ggtatcagcc attactaccc ctgacggtag cacatactac    180

gcagactccg tgaagggccg gttcaccatc tcccgtgaca attccaagaa cacgctgtat    240

ctgcaaatga acagcctgcg tgccgaggac accgcggtat attattgcgc gggtcaggat    300

ggtaatcagg aggacatccg cttttggggt cagggaaccc tggtcaccgt ctcgagcgcg    360

gccgcagaac aaaaactcat ctcagaagag gatct                               395
```

```
<210> SEQ ID NO 106
<211> LENGTH: 387
<212> TYPE: DNA
<213> ORGANISM: Artificial Sequence
<220> FEATURE:
<223> OTHER INFORMATION: Recombinant polynucleotide

<400> SEQUENCE: 106

ggctcgtatg ttgtgtggaa ttgtgagcgg ataacaattt cacacaggaa acagctatga     60

ccatgattac gccaagctta actctcagta tatgagctgg gtccgccagg ctccagggaa    120

gggtctagag tgggtatcag ccattgctac ccctgacggt agcacatact acgcagactc    180

cgtgaagggc cggttcacca tctcccgtga caattccaag aacacgctgt atctgcaaat    240

gaacagcctg cgtgccgagg acaccgcggt atattattgc gcgggtcagg atggtaatca    300

ggaggacatc cgcttttggg gtcagggaac cctggtcacc gtctcgagcg cggccgcaga    360

acaaaaactc atctcagaag aggatct                                        387
```

```
<210> SEQ ID NO 107
<211> LENGTH: 387
<212> TYPE: DNA
<213> ORGANISM: Artificial Sequence
<220> FEATURE:
<223> OTHER INFORMATION: Recombinant polynucleotide

<400> SEQUENCE: 107

ggctcgtatg ttgtgtggaa ttgtgagcgg ataacaattt cacacaggaa acagctatga     60

ccatgattac gccaagctta actctcagta tatgagctgg ggccgccagg ctccagggaa    120

gggtctagag tgggtatcag ccattgctac ccctgacggt agcacatact acgcagactc    180

cgtgaagggc cggttcacca tctcccgtga caattccaag aacacgctgt atctgcaaat    240

gaacagcctg cgtgccgagg acaccgcggt atattattgc gcgggtcagg atggtaatca    300

ggaggacatc cgcttttggg gtcagggaac cctggtcacc gtctcgagcg cggccgcaga    360

acaaaaactc atctcagaag aggatct                                        387
```

```
<210> SEQ ID NO 108
<211> LENGTH: 387
<212> TYPE: DNA
<213> ORGANISM: Artificial Sequence
<220> FEATURE:
<223> OTHER INFORMATION: Recombinant polynucleotide

<400> SEQUENCE: 108

ggctcgtatg ttgtgtggaa ttgtgagcgg ataacaattt cacacaggaa acagctatga     60

ccatgattac gccaagctta actctcagta tatgagctgg gtccgccagg ctccagggaa    120

gggtctagag tgggtatcag ccattactac ccctgacggt agcacataat acgcagactc    180
```

```
cgtgaagggc cggttcacca tctcccgtga caattccaag aacacgctgt atctgcaaat    240

gaacagcctg cgtgccgagg acgccgcggt atattattgc gcgggtcagg atggtaatca    300

ggaggacatc cgcttttggg gtcagggaac cctggtcacc gtctcgggcg cggccgcaga    360

acaaaaactc atctcagaag aggatct                                        387
```

<210> SEQ ID NO 109
<211> LENGTH: 382
<212> TYPE: DNA
<213> ORGANISM: Artificial Sequence
<220> FEATURE:
<223> OTHER INFORMATION: Recombinant polynucleotide

<400> SEQUENCE: 109

```
gtatggtgtg gggaattgtg agcggataac aatttcacac aggaaacaac tatgaccatg     60

attacgccaa gcttgactct caggatatga gctgggtccg ccaggctcca gggaagggtc    120

tagagtgggt atcagccatt actacccctg acggtagcac atactacgca gactccgtga    180

agggccggtt caccatctcc cgtgacaatt ccaagaacac gctgtatctg caaatgaaca    240

gcctgcgtgc cgaggacacc gcggtatatt attgcgcggg tcaggatggt aatcaggagg    300

acatccgctt ttggggtcag ggaaccctgg tcaccgtctc gagcgcggcc gcagaacaaa    360

aactcatctc agaagaggat ct                                             382
```

<210> SEQ ID NO 110
<211> LENGTH: 429
<212> TYPE: DNA
<213> ORGANISM: Artificial Sequence
<220> FEATURE:
<223> OTHER INFORMATION: Recombinant polynucleotide

<400> SEQUENCE: 110

```
atggcccagg tgcagctgtt ggagtctggg ggaggcttgg tacagcctgg ggggtccct      60

gcgtctctcc tgtgcagcct ccggagataa ccttacccat tagactatga cctgggtccg    120

ccaggctcca gggaagggtc tagagtgggt atcaagcatt tcgaccacaa gcggtagcac    180

atactacgca gactccgtga agggccggtt caccatctcc cgtgacaatt ccaagaacac    240

gctgtatctg caaatgaaca gcctgcgtgc cgaggacacc gcggtatatt attgcgcggg    300

tgggcagaat ccgggtcagg tgctttatgt ttctgctagt ccgcaggcgt tcgatttttg    360

gggtcaggga accctggtca ccgtctcgag cgcggccgca gaacaaaaac tcatctcaga    420

agaggatct                                                            429
```

<210> SEQ ID NO 111
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 111

```
cgactgcaga tgaatatacc ttgctttgtt gtgattc                              37
```

<210> SEQ ID NO 112
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 112

```
cgtggtacct catgtacctg gaagcccttt ataggactc                          39


<210> SEQ ID NO 113
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 113

catctgctag caatggcttc ctactttgcg ttg                                33


<210> SEQ ID NO 114
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 114

ttcaatggta ccttattggg cagtttgtcc ctt                                33


<210> SEQ ID NO 115
<211> LENGTH: 1569
<212> TYPE: DNA
<213> ORGANISM: Mokola virus

<400> SEQUENCE: 115

atgaatatac cttgctttgt tgtgattctt ggattcacaa ctacatattc tcttggggaa     60

tttcctttgt acacaattcc cgagaagata gagaaatgga ccccaataga catgatccat    120

ctaagctgcc ccaacaactt attatccgag gaggaaggtt gcaatacaga gtcgcccctc    180

acctacttcg agctcaagag tggttactta gctcatcaga aagttccggg gtttacctgt    240

acaggggtag tgaatgaggc ggagacatac acaaattttg tcgggtatgt caccacaaac    300

ttcaaaagaa aacactttaa gcctacagtc tccgcctgtc gtgatgccta caactggaaa    360

gcgtccgggg atcccaggta tgaggagtca ctgcacactc cttaccctga cagcagctgg    420

ttgagaactg taactaccac caaagaatcc cttcttataa tatcgcctag catcgtggag    480

atggatgtat atggcaggac tctccattcc cccatgttcc cttcagggat atgttctaag    540

ctctatccct ctgttccatc ctgcaaaacc aaccatgatt acacattatg gctgccagaa    600

gatcctagtt tgagtttaat ctgtgatatt ttcacttctg gcagcggaag gaaggccatg    660

aatgggtccc gcatctgcgg attcaaggat gaaaggggat tttacagatc tttgaaaggc    720

gcttgtaagc tgacattgtg cggaaggcct gggatcagat tatttgacgg aacttgggtc    780

tcttttacaa ggccagaagt tcacgtgtgg tgcacccccta accaattggt caatatacac    840

aatgatagaa tagatgagat cgagcacctg attgttgaag acattgtcaa aagaagggag    900

gagtgtttag acactctaga gacagtattt atgtctcaat caattagttt taggaggttg    960

agccactttc ggaaattggt tcccggatat gggaaagctt acaccatttt gaatggtagc   1020

ctgatggaag caaatgtcta ctataaaaga gttgacaggt gggcggacat tttaccctct   1080

aagggatgtc tgaaagtcgg gcaacaatgt atggaccctg tcaacggagt cctcttcaat   1140

gggattatca aaggtccaga tggccagatc ttgatccctg aaatgcagtc agagcagctc   1200

aagcagcata tggacttatt aaaggcagca gtgttccctc tcagacatcc tttaatcagc   1260

caagacgcca tctttaagaa agacggggag gcagatgatt ttgtggacct ccatatgcca   1320
```

```
gatgtacaca aatctgtatc agatgtcgac ttgggtttgc ctcactgggg gttttggatg   1380

ttgatcgggg caactgtagt ggcatttttg gtcttggtgt gtctgctccg tgtctgctgt   1440

aagagagtga ggaggagagg ttcacgacgt acaactcagg agatccccct caacgtttcc   1500

tctgtccccg tccctcgggc cacagtggtg tcatcatggg agtcctataa agggcttcca   1560

ggtacatga                                                           1569
```

<210> SEQ ID NO 116
<211> LENGTH: 1578
<212> TYPE: DNA
<213> ORGANISM: West caucasian bat virus

<400> SEQUENCE: 116

```
atggcttcct actttgcgtt ggtcttgaac gggatctcta tggttttcag tcaaggtctt     60

ttcccccttt acactatccc tgaccatctg ggaccatgga cccccataga tctaagtcac    120

cttcactgcc cgaacaatct ttatactgat gcctcttatt gtacaactga acaaagcata    180

acctacacag agttgaaggt cggatcatct gtgtcacaaa aaatccccgg atttacatgt    240

acgggggtaa gaactgaatc tgtaacatat accaactttg ttggctatgt gactaccacg    300

ttcaagaaaa aacactttcc tcctaaatcc agggactgta gagaggcgta tgagaggaag    360

aaagcaggag atcctagata tgaagagtct ttagcccacc catatcctga caacagttgg    420

ctgagaacag tgactacaac aaaggattcc tgggtgatca tcgagcccag tgtagtggag    480

ttagatatat acacaagtgc cttgtattca cctcttttca aggatggaac atgttcaaaa    540

tctagaacat attcccccta ctgtccaacc aatcatgact tcaccatttg gatgccagag    600

agtgaaaaca taagatctgc ctgtaatctg ttttccacaa gtagagggaa actagtcagg    660

aaccgcacat ccacctgcgg gattatcgat gagagagggc tgttcagatc agttaaagga    720

gcatgcaaaa tatcaatatg cggtaggcag ggaatccgtt tagtggatgg aacttggatg    780

tcttttagat actcagagta cttacctgtg tgttctccat cacagctgat caacacgcac    840

gacatcaagg tcgatgagct ggagaatgct atagttttag acttgattag gaggagagaa    900

gaatgtcttg acaccctaga aacaattttg atgtcaggat ctgtgagtca caggaggctg    960

agtcatttca gaaagctggt tccaggatct gggaaggctt actcttatat aaacggcacc   1020

ttaatggaat cagatgctca ctacatcaag gtagagaatt ggtcagaggt catcccacac   1080

aaaggatgtc tcatggtcgg gggcaaatgc tatgagccag tcaatgatgt gtatttcaac   1140

gggatcattc gggattcaaa taatcagatc ttgatacctg agatgcagtc cagtcttctc   1200

agagaacatg ttgacctgtt gaaggctaat atagttccgt tcaggcatcc aatgttactt   1260

aggtccttca catctgacac tgaagaagat atcgtcgagt ttgtcaaccc tcatctccaa   1320

gatacccaga agttggtgtc agatatggat ctcgggttat cagactggaa gagatatcta   1380

ctaattggat ctttggccgt aggaggagtg gtagcaatct tattcatcgg aacatgttgt   1440

ctgagatgta gagcagggag aaacagaaga acaatccgat ccaatcatag gtcattgtcc   1500

catgacgtgg tgttccataa agataaggat aaagtgatta cttcttggga atcttacaag   1560

ggacaaactg cccaataa                                                 1578
```

<210> SEQ ID NO 117
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 117
tttttttgat tgtggggagg aaagcgacgt caaaccatgg cagctctttt ttt 53

<210> SEQ ID NO 118
<211> LENGTH: 1569
<212> TYPE: DNA
<213> ORGANISM: Lagos bat virus

<400> SEQUENCE: 118
atgagtcaac taaatttgat acccttttc tgtgtaatta tagtcttgtc tgtagaggac 60
tttcctctat atacaattcc tgaaaagata ggtccttgga ctccgatcga cctgatccat 120
ctgagctgtc ctaataattt gcagtcagag gatgaaggat gtggtacctc atcagtcttc 180
agttatgtag agctcaagac aggttatctc actcatcaga aagtgtctgg gttcacctgt 240
acaggagtgg ttaatgaggc tgtcacatac actaactttg tcggatatgt gacaaccacc 300
tttaagcgga aacatttcaa gccgacggca ttggcttgca gagatgctta tcattggaag 360
atttctgggg atccaaggta tgaggagtct ctccacacac catatcctga caacagctgg 420
ttgaggacag ttaccacaac caaagaatct cttgtgataa tctctccaag cattgtggag 480
atggatgtat atagtagaac acttcattct cccatgtttc ccaccgggac ctgttctagg 540
ttctatccgt catccccttc ttgtgccaca aatcatgatt acactttatg gcttccagat 600
gaccctaatc tgagtttggc atgtgatatc tttgtgacca gcacagggaa aaagtcaatg 660
aatggctcta gaatgtgtgg atttacagac gagagagggt attaccggac aataaaagga 720
gcttgtaaac tgacattatg tgggaaacca ggtttgaggt tatttgatgg cacatggata 780
tccttccccc gcccggaagt cactacccgg tgccttccta atcagttagt caatattcac 840
aacaatagga tagatgaagt tgagcatctg attgtagaag atctcattcg aaaaagagaa 900
gagtgtttgg acactttaga gacagtttta atgtccaaat caatcagttt tagacgacta 960
agtcacttca gaaaattagt gccaggatat gggaaggctt acactatttt aaatgggagc 1020
ttaatggaaa ctaacgttca ttatttaaag gttgacaatt ggagtgaaat actgccttcc 1080
aagggatgtt taaaaataaa caatcagtgt gttgctcatt ataagggggt cttctttaac 1140
gggatcatca agggaccaga tggtcatatt ttaatccccg agatgcagtc aagtttgttg 1200
aaacagcaca tggacctctt gaaggcagcg gtttttccct tgaaacatcc tctgattgaa 1260
ccgggctctt tgttcaataa ggatggtgat gccgatgaat ttgttgatgt ccacatgcct 1320
gatgtacata agttggtatc agatgtcgac ttggggctac ccgattggag cctttatgcg 1380
ttgatagggg caactattat agctttcttt atactgatat gtcttattcg tatctgctgc 1440
aagaaggggg gtcggagaaa ctctcccaca aatagacctg atcttcctat agggttgtct 1500
actacacctc aacccaagtc taaagtgata tcatcatggg aatcttataa gggtacctct 1560
aatgtctga 1569

<210> SEQ ID NO 119
<211> LENGTH: 1602
<212> TYPE: DNA
<213> ORGANISM: Duvenhage virus

<400> SEQUENCE: 119
atgccactca atgcagtcat atttactctt ctcctcagat gttccatctg cctgggaaag 60
tttccatttt atacgatccc tgacaaattg ggcccatgga gccctataga catacatcat 120

-continued

```
ctcagttgcc caaataactt ggttgtggaa gacgaaggat gtacaactct aaccccttttt   180
tcatacatgg agttaaaggt aggttacatt acatcaataa aggtgtccgg ttttacctgc    240
actggggtag tgactgaagc tgagacttat accaatttcg ttgggtatgt gacgacaaca    300
tttagaagaa gacatttccg tccatcagtc aactcttgta gagatgcata caattggaag    360
atcgcaggag accctaggta tgaagaatca ctacacaacc cttatccaga ctctcactgg    420
ctcagaactg tcaagactac aaaagaatct cttttgataa tctcccccag cgtggctgac    480
atggatgcgt atgacaagaa gctttactcc aagattgttt ccaacggaag gtgttcggaa    540
atatctcctg ggtccccttt ctgtcccacc aatcatgaat acactatctg gatgcccgag    600
agctcaaacc ccggaatatc ctgtgacata ttcacaagaa gcatggggaa gaaagccacc    660
aaagatggac agttatgtgg gtttgtagat gagagaggac tgtacaaatc tctgaaggga    720
gcttgtagat taagactctg tgggatcagc ggactgagac tgatggacgg gtcatgggtt    780
tcactcccac aggttaacaa ctcagaatgg tgctccccag accaacttgt taacattcac    840
gacttccatt cagatgagat agagcatctc gtcgcagatg agttggtgaa aaagagagag    900
gattgtctag acgcccttga aactatcctc ttcaccaaat ctataagttt ccggcgttta    960
agccatcttc ggaagctagt tccaggcttt ggtaaggcat atactatcat aaataggacc   1020
cttatggaag cagaggctca ttacaagtca gtgcgggagt ggaaggaaat tattccatcc   1080
aaggggtgtc tgaaggcagg agggaggtgc tatcctcatc acaatggaat tttcttcaac   1140
gggatcattc tgggtccggg aggggagatc ttgatccctg agatgcagtc tgccttgctc   1200
caacagcaca ttgagctgtt agagtcctct gtagttcccc tcaaacaccc cctggcagac   1260
ccttcgactg tcttcaagaa cgatgatgaa gcggagagtt tcgtagatgt tcaccttcct   1320
gatacaaacc aaaaaatatc tggaattgac ttagggttgc cagagtggaa acgttacttc   1380
ctaataggag tctcagcagt tgctttgttg gctttatcta taattatcgc tgtctgttgc   1440
aaaaggttca ggaaaaggaa gaaatccaaa cccggtccag tagaattgac tagaaaagtg   1500
tctgtcatat ccaaaggaaa tggaccggtc ccttcctggg aatcttataa agaaggaacc   1560
acaggagatg ttcgtaatac gactccatca acaagggagt ga                       1602
```